United States Patent
Caligiuri et al.

(10) Patent No.: US 9,603,873 B2
(45) Date of Patent: Mar. 28, 2017

(54) ACTIVATION OF INNATE IMMUNITY BY MIRNA FOR CANCER AND INFECTION TREATMENT

(71) Applicant: Ohio State Innovation Foundation, Columbus, OH (US)

(72) Inventors: Michael A. Caligiuri, Columbus, OH (US); Jianhua Yu, Columbus, OH (US); Shun He, Columbus, OH (US); Rossana Trott, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 14/649,054

(22) PCT Filed: Dec. 3, 2013

(86) PCT No.: PCT/US2013/072792
§ 371 (c)(1),
(2) Date: Jun. 2, 2015

(87) PCT Pub. No.: WO2014/089029
PCT Pub. Date: Jun. 12, 2014

(65) Prior Publication Data
US 2016/0015748 A1 Jan. 21, 2016

Related U.S. Application Data

(60) Provisional application No. 61/732,481, filed on Dec. 3, 2012, provisional application No. 61/768,245, filed on Feb. 22, 2013.

(51) Int. Cl.
| | | |
|---|---|---|
| C12N 15/113 | (2010.01) |
| A61K 35/17 | (2015.01) |
| A61K 31/7105 | (2006.01) |
| A61K 45/06 | (2006.01) |
| A61K 9/127 | (2006.01) |
| A61K 38/20 | (2006.01) |
| A01K 67/027 | (2006.01) |
| A61K 38/21 | (2006.01) |
| A61K 9/51 | (2006.01) |

(52) U.S. Cl.
CPC .......... *A61K 35/17* (2013.01); *A01K 67/0275* (2013.01); *A61K 9/127* (2013.01); *A61K 31/7105* (2013.01); *A61K 38/20* (2013.01); *A61K 38/208* (2013.01); *A61K 38/2013* (2013.01); *A61K 38/2086* (2013.01); *A61K 38/21* (2013.01); *A61K 45/06* (2013.01); *C12N 15/113* (2013.01); *A01K 2217/052* (2013.01); *A01K 2217/075* (2013.01); *A01K 2217/15* (2013.01); *A01K 2227/00* (2013.01); *A01K 2227/105* (2013.01); *A01K 2267/0331* (2013.01); *A01K 2267/0337* (2013.01); *A61K 9/5161* (2013.01)

(58) Field of Classification Search
CPC combination set(s) only.
See application file for complete search history.

(56) References Cited

U.S. PATENT DOCUMENTS

2010/0267139 A1* 10/2010 Kjems .................. A61K 9/5161
435/375

OTHER PUBLICATIONS

Trotta et al. (Blood, vol. 119, pp. 3478-3485, published online Feb. 29, 2012).*

* cited by examiner

*Primary Examiner* — J. E. Angell
(74) *Attorney, Agent, or Firm* — MacMillan, Sobanski & Todd, LLC

(57) ABSTRACT

Methods and compositions involving miR-122, miR-15b, miR-21, and miR-155, which are useful for the treatment of various diseases, such as cancers, are described. Further described are methods and compositions useful for increasing, activating, or regulating NK cells and surface antigens.

10 Claims, 43 Drawing Sheets
(6 of 43 Drawing Sheet(s) Filed in Color)

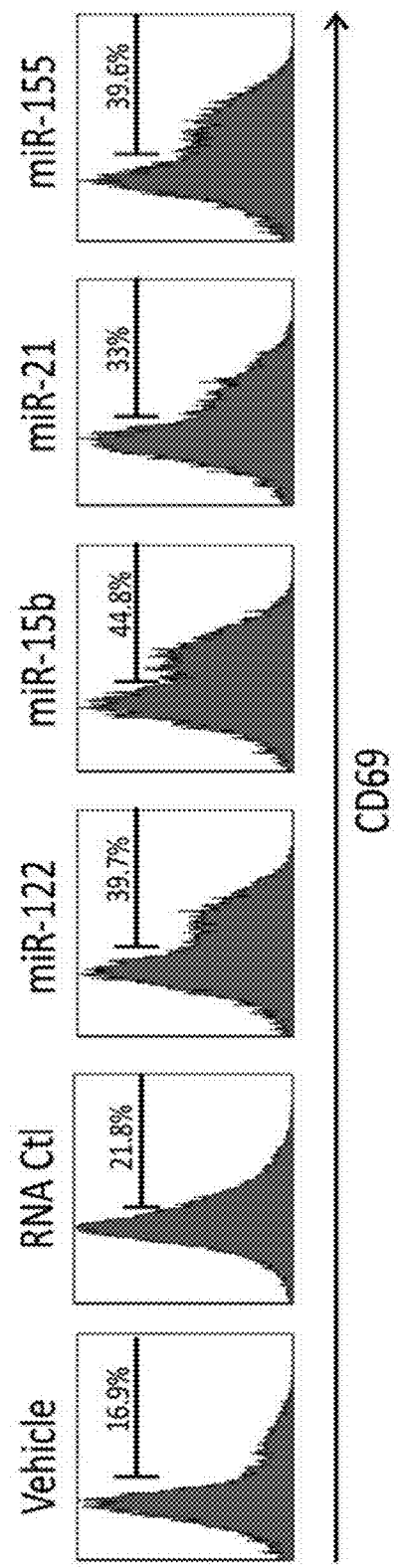

ACTIVATION OF INNATE IMMUNITY BY MIRNA FOR CANCER AND INFECTION TREATMENT

CROSS-REFERENCE TO RELATED APPLICATIONS

This application the benefit of the PCT/US2013/072792 filed Dec. 3, 2013 which claims priority to U.S. Provisional Application No. 61/732,481, filed under 35 U.S.C. §111(b) on Dec. 3, 2012, and U.S. Provisional Application No. 61/768,245, filed under 35 U.S.C. §111(b) on Feb. 22, 2013, the entire disclosures of which are expressly incorporated herein by reference.

STATEMENT REGARDING FEDERALLY SPONSORED RESEARCH

This invention was made with government support under Grant No. CA16058, CA95426, CA68458 and T32-CA009338 by the National Cancer Institute. The government has certain rights in the invention.

BACKGROUND OF THE INVENTION

Natural killer (NK) cells are important components of the immune system because of their ability to directly kill pathogen-infected and tumor cells, as well as their immunoregulatory functions via production of pro-inflammatory cytokines and chemokines. During maturation, NK cells acquire cytokine receptors, activating and inhibitory receptors, adhesion molecules and NK cell effectors functions. In mouse, the committed NK cell precursors (NKP) express the common gamma chain receptor (R) for IL-2 and IL-15 (CD122), IL-7Rα (CD127), and c-kit (CD117). NK cell precursors then acquire an immature phenotype in C57BL/6 mice with the acquisition of NK1.1, CD94, the TNFR superfamily member CD27, the integrin CD11b and Ly49 receptors. Additionally, during terminal maturation, NK cells down modulate CD27 and acquire high surface density expression of CD11b.

Acquisition of lytic functions and interferon-gamma (IFN-γ) production in NK cells depends on complex interactions that involve signaling molecules, transcription factors, and microRNAs (MiRs). MiRs are small non-coding RNA that modulate post-transcriptional gene expression of multiple targets, and are implicated in regulating several cellular and developmental processes. MiRs regulate gene expression by binding to the 3' UTR and inducing either suppression of mRNA translation or mRNA degradation.

In spite of considerable research into therapies to treat these diseases, they remain difficult to treat effectively, and the mortality observed in patients indicates that improvements are needed in the diagnosis, treatment, and prevention of these diseases.

There is no admission that the background art disclosed in this section legally constitutes prior art.

SUMMARY OF THE INVENTION

Among miRs, miR-155 plays a protective role in immunity when its expression is tightly regulated, and contributes to the development of malignancies when its expression is deregulated. Without wishing to be bound by theory, it is believed that miR-155 controls the development and functions of different immune cells including T, B, and dendritic cells. MiR-155 overexpression has been observed not only during cell activation but also in different types of cancer. In human NK cells, the constitutive expression of miR-155 is different in $CD56^{bright}$ and $CD56^{dim}$ subsets which represent stages 4 and 5 of NK cell development. MiR-155 expression is also up-regulated during human NK cell activation. In particular, the induction of miR-155 and its precursor non-protein-coding transcript BIC depends on signaling events induced by triggering IL-18R alone or CD16 alone, but not via triggering IL-12R alone. However, the combination of IL-12 with either IL-18 or CD16 activation synergistically induces miR-155 expression following kinetics very similar to IFN-γ production. The synergistic induction of miR-155 after IL-12 and IL-18 co-stimulation depends on IL-12-mediated induction of IL-18α. Further, miR-155 plays a role in regulating IFN-γ production. In both resting and activated human NK cells, miR-155 inhibits the expression of SHIP1 inositol phosphatase, which is responsible at least in part for the regulation of IFN-γ production. MiR-155 is also over-expressed in NK cell lymphoma/leukemia where it inversely correlates with SHIP1 expression and directly correlates with AKT activation.

Provided herein is a method of activating NK cells in a mammal comprising administering an effective amount of a miRNA to a mammal to activate NK cells in the mammal, wherein the miRNA is selected from the group consisting of miR-122, miR-15b, miR-21, and miR-155. In certain embodiments, the miRNA is administered in a liposomal formulation. In certain embodiments, the miRNA is administered in chitosan nanoparticles. In certain embodiments, the miRNA is administered to the mammal for at least four consecutive weeks. In certain embodiments, the miRNA is administered to the mammal at least three times per week. In certain embodiments, the activated NK cells produce an anti-tumor effect in the mammal. In certain embodiments, the NK cells produce an antiviral effect in the mammal. In certain embodiments, the activated NK cells produce an anti-inflammatory effect in the mammal.

Provided herein is a method of activating NK cells, comprising administering an effective amount of a miRNA to NK cells, wherein the miRNA is selected from the group consisting of miR-122, miR-15b, miR-21, and miR-155; and stimulating the NK cells with a cytokine to activate the NK cells. In certain embodiments, the miRNA is administered to the NK cells in a nanoparticle. In particular embodiments, the nanoparticle comprises chitosan.

In certain embodiments, the miRNA consists essentially of miR-122. In certain embodiments, the miRNA consists essentially of miR-15b. In certain embodiments, the miRNA consists essentially of miR-21. In certain embodiments, the miRNA consists essentially of miR-155.

In certain embodiments, the miRNA is administered to the NK cells in a liposomal formulation. In certain embodiments, the miRNA is in a complex with DOTAP. In certain embodiments, the concentration of the miRNA in the complex is about 10 μg/mL. In certain embodiments, the concentration of the DOTAP in the complex is about 50 μg/mL.

In certain embodiments, the cytokine comprises an interleukin selected from the group consisting of: IL-2, IL-12, IL-15, IL-18, and a combination thereof. In certain embodiments, the interleukin comprises IL-12 and is present at a concentration of less than about 10 ng/mL. In certain embodiments, the interleukin comprises IL-12 and is present at a concentration of about 2.5 ng/mL.

Further provided herein is a method of treating a disease comprising delivering miR-155 into NK cells to create miR-155 tg NK cells, wherein the miR-155 tg NK cells overexpress miR-155; stimulating the miR-155 tg NK cells with an interleukin; and transferring the stimulated miR-155 tg NK cells into a host having a disease to treat the disease. In certain embodiments, the interleukin is selected from the group consisting of IL-12, IL-15, IL-18, IL-20, and a combination thereof. In certain embodiments, the disease is a cancer. In certain embodiments, the disease is acute myeloid leukemia. In certain embodiments, the disease is lymphoma. In certain embodiments, the disease is an infection. In certain embodiments, the disease comprises inflammation.

In certain embodiments, the miR-155 is delivered into the NK cells through a nanoparticle. In certain embodiments, the nanoparticle comprises chitosan. In certain embodiments, the miR-155 is delivered into the NK cells through a liposomal formulation. In certain embodiments, the interleukin comprises IL-20 and is present at a concentration of about 20 ng/mL. In certain embodiments, the interleukin comprises IL-18 and is present at a concentration of about 10 ng/mL.

Further provided herein is a method of treating or preventing lymphoma comprising administering an effective amount of miR-122 to a patient in need thereof to treat or prevent lymphoma. In certain embodiments, the miR-122 is administered through a nanoparticle. In certain embodiments, the nanoparticle comprises chitosan. In certain embodiments, the miR-122 is administered through a liposomal formulation. In certain embodiments, the method further comprises administering an additional anti-cancer agent. In certain embodiments, the method further comprises administering a cytokine to the patient. In certain embodiments, the cytokine comprises an interleukin selected from the group consisting of IL-2, IL-12, IL-15, IL-18, and IL-20. In certain embodiments, the cytokine is administered simultaneously with the miR-122. In certain embodiments, the miR-122 is administered for at least four consecutive weeks. In certain embodiments, the miR-122 is administered three times per week.

Further provided herein is a method of activating innate immunity to control complications, the method comprising administering an effective amount of a miRNA to a patient in need thereof, wherein the miRNA is selected from the group consisting of miR-122, miR-15b, miR-21, and miR-155; and administering an effective amount of an interleukin to the patient, to control complications. In certain embodiments, the complications comprise one or more of: graft-versus-host diseases (GVHD), infections, and relapses. In certain embodiments, the interleukin is selected from the group consisting of IL-2, IL-12, IL-15, IL-18, and IL-20.

Further provided herein is a method of increasing CD69 expression in NK cells, the method comprising treating NK cells with an effective amount of a miRNA in the presence of an effective amount of IL-12 to increase CD69 expression in the cells, wherein the miRNA is one of miR-155, miR-15b, or miR-122. In certain embodiments, the NK cells are treated for at least 36 hours. In certain embodiments, the effective amount of IL-12 is at least about 2.5 ng/mL.

Further provided is a method to increase CD107a expression in tumor cells, the method comprising contacting tumors cells with an effective amount of a miRNA in the presence of IL-12, wherein the miRNA comprises miR-122 or miR-15b, to increase CD107a expression in the tumor cells.

Further provided herein is a method for improving survival comprising engineering miR-155 tg NK cells that overexpress miR-155; and adoptively transferring the miR-155 tg NK cells into an immune-deficient host to improve survival.

Further provided herein is a method of inducing NK cell activation, the method comprising isolating exosomes from a serum sample, wherein the exosomes contain miR-122 and miR-21, and adding the exosomes to NK cells to induce activation of the NK cell.

Further provided herein is a method of enhancing phospho-Akt and phospho-Erk expression in NK cells, the method comprising delivering miR-155 to NK cells, and activating the NK cells with IL-15 to enhance phospho-Akt and phospho-Erk expression in the NK cells. In certain embodiments, the miR-155 is delivered to the NK cells through a nanoparticle. In certain embodiments, the nanoparticle comprises chitosan. In certain embodiments, the miR-155 is delivered to the NK cells through a liposomal formulation.

Further provided is a method to inhibit tumor growth comprising engineering miR-155 tg NK cells, wherein the miR-155 tg NK cells overexpress miR-155, and administering the miR-155 NK cells to a patient in need thereof to inhibit tumor growth. In certain embodiments, the miR-155 tg NK cells are administered through an injection. In certain embodiments, the miR-155 tg NK cells are in the form of a liposomal formulation.

Further provided is a method of impairing activation of NK cells, the method comprising mutating a miRNA by substituting uridines (Us) with guanosines (Gs) to create a mutated miRNA, and administering an effective amount of the mutated miRNA to NK cells to impair activation of the NK cells. In certain embodiments, the method further comprises the step of administering an effective amount of an interleukin to the NK cells. In certain embodiments, the interleukin consists essentially of IL-12. In certain embodiments, the miRNA is selected from the group consisting of: miR-122, miR-15b, miR-21, and miR-155.

Further provided is a method of increasing surface expression of CD69, the method comprising administering an effective amount of miR-122 or miR-15b to a patient in need thereof, and increasing surface expression of CD69.

Further provided is a method of increasing phosphorylation of p65 in NK cells comprising priming NK cells with an interleukin, and treating the primed NK cells with a miRNA to increase phosphorylation of p65 in the NK cells, wherein the miRNA is selected from the group consisting of: miR-122, miR-15b, miR-21, and miR-155. In certain embodiments, the interleukin comprises IL-12.

Further provided herein is a method of reducing SHIP1 expression in a cell, comprising delivering an effective amount of miR-155 to a cell and reducing SHIP1 expression in the cell, wherein the miR-155 is delivered to the cell in a chitosan nanoparticle or a liposomal formulation.

Further provided herein is a method of enhancing IFN-γ production by NK cells comprising treating NK cells with a combination of a miRNA and IL-12, and enhancing IFN-γ production by the NK cells, wherein the miRNA is selected from the group consisting of miR-122, miR-15b, miR-21, and miR-155. In certain embodiments, the miRNA is in a liposomal formulation. In certain embodiments, the miRNA is in a chitosan nanoparticle.

Further provided herein is a method to enhance NK cells' ability to participate in surveillance against malignant transformation or infectious insult, comprising administering an effective amount of a miRNA to NK cells, and enhancing the NK cells' ability to participate in surveillance against malignant transformation or infectious insult, wherein the miRNA is selected from the group consisting of: miR-122, miR-15b, miR-21, and miR-155.

Further provided herein is a method of treating an infection comprising administering an effective amount of a miRNA to a patient in need thereof, wherein the miRNA is selected from the group consisting of miR-122, miR-15b, miR-21, and miR-155, and administering an effective amount of an interleukin to the patient, to treat an infection. In certain embodiments, the interleukin is selected from the group consisting of IL-2, IL-12, IL-15, IL-18, and IL-20.

Further provided herein is a method of inhibiting tumor growth, the method comprising administering an effective amount of miR-122 to a patient in need thereof, and inhibiting tumor growth. In certain embodiments, the miR-122 is in a liposomal formulation. In certain embodiments, the miR-122 is in a chitosan nanoparticle.

Further provided herein is a method of increasing Granzyme B levels in NK cells, the method comprising activating NK cells with an effective amount of IL-2 to increase Granzyme B levels in the NK cells, wherein the NK cells overexpress miR-155.

Further provided herein is a method of improving survival of NK cells comprising delivering miR-155 to NK cells in the absence of cytokines to improve survival of the NK cells.

Further provided herein is a method of improving expansion of NK cells comprising delivering miR-155 to NK cells in the presence of IL-15 to improve expansion of the NK cells.

Further provided herein is a pharmaceutical composition comprising a miRNA selected from the group consisting of: miR-122, miR-15b, miR-21, and miR-155; an interleukin selected from the group consisting of: IL-2, IL-12, IL-15, IL-18, and IL-20; and a pharmaceutically acceptable carrier. In certain embodiments, the pharmaceutically acceptable carrier comprises nanoparticles. In certain embodiments, the nanoparticles comprise chitosan.

Further provided herein is a pharmaceutical composition comprising an active ingredient; and an adjuvant comprising a miRNA selected from the group consisting of miR-122, miR-15b, miR-21, and miR-155; wherein the active ingredient is an anti-cancer agent, an anti-inflammatory agent, or an anti-infective agent. In certain embodiments, the anti-cancer agent is selected from the group consisting of: chemotherapeutic agents; cytotoxins; antimetabolites; alkylating agents; protein kinase inhibitors; anthracyclines; antibiotics; antimitotic agents; corticosteroids; radiopharmaceuticals; cytokines; enzymes; interferons; krestin; lentinan; sizofiran; picibanil; ubenimex; acitretin; fenretinide; thalidomide; zoledronic acid; angiostatin; aplidine; cilengtide; combretastatin A-4; endostatin; halofuginone; rebimastat; removab; Revlimid; squalamine; ukrain; Vitaxin; cisplatin; carboplatin; nedaplatin; oxaliplatin; camptothecin; 10-hydroxycamptothecin; 9-aminocamptothecin; irinotecan; SN-38; edotecarin; topotecan; compounds or chelates that include radionuclides; filgrastim; lentinan; sizofilan; TheraCys; ubenimex; WF-10; aldesleukin; alemtuzumab; BAM-002; dacarbazine; daclizumab; denileukin; gemtuzumab ozogamicin; ibritumomab; imiquimod; lenograstim; lentinan; Corixa; molgramostim; OncoVAX-CL; sargramostim; tasonermin; tecleukin; thymalasin; tositumomab; Virtilizin; Z-100; epratuzumab; mitumomab; oregovomab; pemtumomab; Provenge; alitretinoin; ampligen; atrasentan bexarotene; bortezomib; Bosentan; calcitriol; exisulind; finasteride; fotemustine; ibandronic acid; miltefosine; mitoxantrone; 1-asparaginase; procarbazine; dacarbazine; hydroxycarbamicle; pegaspargase; pentostatin; tazarotne; Telcyta; Velcade; Millenium; tretinoinor; and combinations thereof. In certain embodiments, the anti-infective agent is selected from the group consisting of penicillins, cephalosporins, macrolides, sulfonamides, quinolones, aminoglycosides, beta lactams antibiotics, linezolid, vancomycin, ketolides, macrolides, amphotericin B, azole antifungals, amylmetacresol, benzalkonium, cetylpyridinium, chlorhexidine, dequilinium, domiphen, dichlorobenzyl alcohol, phenol, tyrothicin, antiseptics, and combinations thereof. In certain embodiments, the anti-inflammatory agent is selected from the group consisting of: glucocorticoids, disodium cromoglycate, nedcromil sodium, acetyl salicylic acid, methyl salicylate, sodium salicylate, phenylbutazone, oxyphenbutazone, apazone, indomethacin, sulindac, tolmetin, mefenamic acid, ibuprofen, naproxen, fenoprofen, flurbiprofen, ketoprofen, and combinations thereof.

Further provided herein is a composition of matter comprising a miRNA selected from the group consisting of miR-155, miR-122, miR-15b, miR-21, and miR-155; and a chitosan nanoparticle, wherein the miRNA is encapsulated within the chitosan nanoparticle.

Further provided herein is a kit for preparing a pharmaceutical composition comprising a first container housing a miRNA selected from the group consisting of miR-122, miR-15b, miR-21, and miR-155; and a second container housing a pharmaceutically acceptable carrier, diluent, or excipient. In certain embodiments, the pharmaceutically acceptable carrier, diluent, or excipient comprises nanoparticles or a liposomal formulation. In certain embodiments, the kit further comprises a third container housing a cytokine.

Further provided herein is a transgenic non-human animal comprising a disruption in endogenous miR-155. In certain embodiments, the transgenic non-human animal further comprises a disruption in endogenous IL-15.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIGS. 1A-1B: MiRNAs increase CD69 surface expression on NK cells.

FIG. 1A: Highly purified (≥99%) human NK cells were treated with miRNAs, DOTAP vehicle control, or nonspecific, single-stranded RNA, RNA41(RNA-Ctl), for 36 hours in the presence of a low concentration of IL-12 (2.5 ng/mL). The treated cells were then subjected to flow cytometric analysis to determine the percentage of $CD69^+$ cells. Representative data from 1 of 6 donors with similar results are shown.

FIG. 1B: Summary of data from 4 donors obtained in 1 experiment. *$P<0.05$ and error bars represent standard deviation.

FIG. 2A: Highly purified (≥99%) human NK cells were treated with miRNAs, DOTAP vehicle control, or nonspecific, single-stranded RNA, RNA41 (RNA-Ctl), for 36 hours in the presence of a low concentration of IL-12 (2.5 ng/mL). Supernatants were harvested for enzyme-linked immunoassay (ELISA) and cells were harvested for real-time RT-PCR analysis to determine the levels of IFN-γ secretion (upper panel) and gene expression (lower panel), respectively. Gene expression of the vehicle was normalized to 1. Experimental values are each presented as fold change compared with that of the vehicle. Data shown represent 1 of 3 donors with similar results.

FIGS. 2B-2C: Highly purified human NK cells were treated with miRNAs or DOTAP vehicle control for 36 hours in the presence of a low concentration of IL-12 (2.5 ng/mL). The cells were then incubated with K562 tumor cells at a ratio of 1:1 (effector:target). After 4 hours, CD107a expression was assessed by flow cytometric analysis. Shown in FIG. 2C are representative data from 1 of 5 donors with similar results. Summary data of 5 donors. In all panels, error bars represent standard deviation. *$P<0.05$ and **$P<0.01$.

FIG. 2D: Cells were treated and data were collected as described in FIG. 2A, with the exception that concentrations of miR-122 were varied, as indicated on the X-axis. The data demonstrate that miR-122 activates NK cells in a dose-dependent fashion.

FIG. 3A: Mice were treated in vivo with vehicles or 20 µg RNA-Ctl, miR-122, or miR-15b for 4 days. The treated mice were then sacrificed, and total splenocytes were isolated for flow cytometric analysis to measure CD69 surface expression after gating on CD3$^-$NK1.1$^+$ NK cells. Representative data from 1 of 6 mice with similar results (left) as well as summary data from 3 mice (right) in 1 experiment are shown.

FIG. 3B: The prepared splenocytes from A were cocultured with YAC-1 tumor cells for 3 hours without any exogenous IL-12 and subjected to flow cytometric analysis of CD107a expression after gating on CD3$^-$NK1.1$^+$ NK cells. *$P<0.05$ and **$P<0.01$, respectively, and error bars represent standard deviation.

FIG. 4A: Human PBMCs were stimulated with miRNAs as described in FIG. 1A and subjected to flow cytometric analysis of CD69 surface expression within CD3$^+$ T cells. Depicted are representative data from 1 of 6 donors (top), as well as summary data from 3 donors in 1 experiment (bottom). The data demonstrates that miRNAs do not significantly change human T-cell surface expression of CD69.

FIG. 4B: Mice were treated in vivo, and cells were prepared for flow cytometric analysis as described in FIG. 3A. Depicted are representative data from 1 of 6 mice with similar data (left), as well as summary data from 3 mice in 1 experiment (right), indicating that miRNAs do not significantly change murine T-cell surface expression of CD69 in vivo. Error bars represent standard deviation.

FIG. 5A: Real-time RT-PCR was used to determine the level of TLR mRNA expressed in highly purified human NK cells. The mRNA level of TLR5 was found to be lowest and was normalized to 1. The mRNA level of other TLRs was presented as relative to that of TLR5. Data are shown as the average of 3 donors.

FIG. 5B: Purified human NK cells were preincubated for 1.5 hours with a nonspecific IgG or anti-TLR1, anti-TLR3, or anti-TLR6-blocking antibody (α). Cells were then stimulated with miR-122 as described in FIG. 1A in the presence of the blocking antibody, and supernatants were harvested to measure IFN-γ protein via ELISA. The concentration of IFN-γ in the purified NK cells incubated with IgG and miR-122 was arbitrarily set at 1. Data were averaged from 3 donors. *$P<0.05$ and error bars represent standard deviation (SD).

FIG. 5C: NK-92 cells were infected with pSUPER-TLR1-GFP retroviruses, and stably transfected cells were sorted based on GFP expression. Both the vector-transduced cells (pSUPER) and the TLR1 knockdown cells (pSUPER-TLR1, confirmed by immunoblotting; upper panel) were stimulated with miR-122 or miR-15b as described in FIG. 1A, and cell-free supernatants were collected to assess IFN-γ secretion via ELISA (lower panel). **$P<0.01$ and error bars represent SD.

FIG. 5D: Purified human NK cells were stimulated with miR-122 or miR-15b as described in FIG. 1A and subsequently subjected to immunoblotting using p65 and phospho-p65 (p-p65) Abs. β-actin immunoblotting was included to demonstrate equal loading of total protein. Data shown represent 2 of 4 donors with similar results. Numbers beneath each lane represent quantification of p-p65 by densitometry, normalized by p65.

FIG. 5E: The experiment was performed as in (D) except that anti-TLR1 blocking mAb or its control IgG was included in the culture in the presence of miR-122. Data shown represent 1 of 3 donors with similar results. Numbers beneath each lane represent quantification of p-p65 by densitometry, normalized by p65.

FIG. 6A: Ventral bioluminescence imaging of mice bearing A20 lymphoma. Athymic nude mice were injected with $1\times10^5$ luc-expressing A20 cells via tail veins and subjected to miRNA stimulation alone or combined with TM-β1, according to the schedule described in Example I. The pseudo color indicates the relative signal strength for tumor growth, with strongest in red and weakest in purple.

FIG. 6B: Quantification summary of units of photons per second per mouse from FIG. 6A. Data are shown as mean±standard deviation from each group of mice. *$P<0.05$; **$P<0.01$.

FIG. 10A: Exosomes were isolated from serum of healthy donors with ExoQuick Exosome (System Biosciences). Exosomes were verified by CD9 expression determined by Western blotting.

FIG. 10B: Purified exosomes were further subjected to RNA extraction, and miR-122 and miR-21 expression levels were detected with Real-time RT-PCR using TaqMan miRNA assays. Small nuclear RNA RNU44 was also included as a control. Results indicate that exosomes contain high levels of miRNAs including miR-122 and miR-21, which were included in this evaluation assessing NK cell activation.

FIG. 10C: Extracted exosomes were added to NK cells purified from the corresponding (autologous) donors and incubated for 36 hr. The NK cells were then harvested and subjected to flow cytometric analysis to detect CD69 surface expression.

FIG. 10D: Summary data of NK cell activation by exosomes for 5 normal human donors. * indicates P<0.05 and **P<0.01.

FIG. 20A: $NK1.1^+CD3^-$ FACS sorted NK cells from spleen of wt and miR-155 tg mice were analyzed for miR-155 expression by Real time RT-PCR.

FIG. 20B: Freshly isolated splenocytes of wt and miR-155 tg were stained with anti-NK1.1 and anti-CD3 Abs and analyzed by flow cytometry for percentage of $NK1.1^+CD3^-$ NK cells.

FIG. 20C: The absolute number of NK cells was calculated in spleens of wt versus miR-155 tg mice. The graph summarizes data from 4 wt and 2 miR-155 tg littermate mice. *Statistically significant.

FIG. 21A: BrdU drinking water was administrated daily for 10 days to wt and miR-155 tg mice. BrdU incorporation in splenic NK cells was determined by surface staining of NK1.1 and CD3, followed by intracellular staining of BrdU. The histogram represents BrdU incorporation within a gated population of $NK1.1^+CD3^-$ wt and miR155 tg NK cells. Mean of percentage of BrdU incorporation of wt and miR-155 NK cells from 10 mice is shown on graph (right panel).

FIG. 21B: $2\times10^5$ FACS sorted $NK1.1^+CD3^-$ splenic NK cells were cultured in IL-15 (100 ng/ml) for seven days. Viable cells were enumerated after culturing for 3, 5, and 7 days by tripan blue dye exclusion.

FIG. 21C: Splenocytes of wt, miR-155 tg, IL-15 tg, or double miR-155/IL-15 tg mice were stained with anti-NK1.1 and anti-CD3 Abs, and analyzed by flow cytometry for percentage of $NK1.1^+CD3^-$ NK cells (left) and for absolute number of NK cells (right).

FIG. 21D: Freshly isolated splenocytes were cultured in medium without cytokines for 24 h, followed by surface staining of NK1.1 and CD3 and labeling with 7-AAD and Annexin V. Representative dot plots from five experiments show staining for 7-AAD and Annexin V in $NK1.1^+CD3^-$ NK cells. *Statistically significant.

FIG. 22A: Antigens with significantly higher expression on miR-155 tg NK cells compared to wt NK cells.

FIG. 22B: Antigens with no difference in expression.

FIG. 22C: Antigens with significantly lower expression on miR-155 tg NK cells compared to wt NK cells. The Y axis indicates the mean±SEM percent of surface antigen expression on gated NK1.1$^+$CD3$^-$ cells from at least 5 mice/group for each antigen. *Statistically significant.

FIG. 23A: Splenocytes from wt and miR-155 tg mice were stained with anti-NK1.1, anti-CD3, anti-CD27 and anti-CD11b Abs. Contour maps represent surface density expression of CD27 and CD11b on gated NK1.1$^+$CD3$^-$ NK cells.

FIG. 23B: The graph summarizes mean percentage of CD11b$^{low}$CD27$^{high}$, CD11b$^{high}$CD27$^{high}$ and CD11b$^{high}$CD27$^{low}$ NK subsets from 10 miR-155 tg and 4 wt mice.

FIG. 23C: $1\times10^5$ to $2\times10^5$ CD11b$^{low}$CD27$^{high}$ NK cells collected from 2 CD45.2$^+$ and from 3 CE45.2$^+$ miR-155 tg mice were each intravenously injected into sublethally irradiated CD45.1+ recipient mice. After 16 days splenic NK cells were harvested and the progeny of adoptively transferred CD11b$^{low}$CD27$^{high}$ NK cells from wt and miR-155 tg mice were analyzed via FACS with a gate on CD45.2 expression and assessment for co-expression of CD27 and CD11b. With this, the frequency of CD11b$^{low}$CD27$^{high}$, CD11b$^{high}$CD27$^{high}$ and CD11b$^{high}$CD27$^{low}$ NK subsets was quantified and graphed. Data shown is from one experiment, representative of four such experiments.

FIG. 23D: Total wt and miR-155 tg NK.1$^+$CD$^{3-}$ NK cells were each co-stimulated in vitro for 18 h using IL-12 (20 ng/ml) and IL-18 (10 ng/ml) and analyzed for IFN-γ secretion by ELISA.

FIG. 23E: FACS sorted CD11b$^{low}$CD27$^{high}$, DC11b$^{high}$CD27$^{high}$ and CD11b$^{high}$CD27$^{low}$ NK subsets were stimulated for 18 h in vitro with IL-12 (20 ng/ml) and IL-18 (10 ng/ml). Supernatants were then collected and analyzed for IFN-γ by ELISA. *Statistically significant.

FIG. 24A: FACS sorted NK1.1$^+$CD3$^-$ NK cells from wt and miR-155 tg mice were used as effector cells in a 4-h $^{51}$Cr release assay using YAC-1 and RMA-Rae1β tumor cells as targets.

FIG. 24B: Eight days after expansion in IL-2, sorted wt and miR-155 tg NK cells were assayed for ADCC against $^{51}$Cr labeled P815 Ab coated targets cells.

FIG. 24C: Left: Wt and miR-155 tg NK cells were mixed with RMA-Rae1β tumor cells at ratio 2:1 and injected subcutaneously into the flank of Rag$^{2-/-}$xII2rg$^{-/31}$ recipient mice. RMA-Rae1β tumor cells alone were injected as control. Tumor volumes were calculated every two days. The errors bars represent SEM. The graph summarizes mean data from 2 experiments with a total of 7 mice for the wt and for the miR-155 tg group.

FIG. 24C: Right: the percent survival of mice that had been inoculated with either wt or miR-155 tg NK cells in combination with RMA-Rae1β tumor cells at ratio 2:1 or RMA-1β tumor cells alone as control is shown. Data from 3 independent experiments using a total of 11 mice for each group are summarized in the in the Kaplan-Meier survival plots. Data are representative of four experiments.

FIG. 24D: Resting (left) and 8 days IL-2 activated (right) NK1.1$^+$CD3$^-$ wt and miR-155 tg NK cells were analyzed for Granzyme B, Granzyme M, Perforin and Actin protein levels by immunoblot.

FIG. 24E: Left: wt and miR-155 tg NK cells labeled with PE-conjugated anti-NK1.1 Ab were incubated with GFP$^+$ YAC-1 tumor cells. Conjugate formation was analyzed at time 0 and after 10 min of incubation by flow cytometry. NK cell-target cell conjugates are gated and identified as NK1.1$^+$ GFP$^+$ cells. The percentage of conjugates is shown on top of the representative dot plots. Right: the graph summarizes the data of conjugate formation obtained from three wt and three miR-155 tg NK cell samples co-incubated with YAC-1 tumor cells. *Statistically significant.

FIG. 25A: NK1.1$^+$CD3$^-$ NK cells from wt and miR-155 tg mice were analyzed for Ship1 protein levels by immunoblot. Grb2 was assessed to ensure equal loading.

FIG. 25B: NK1.1$^+$CD3$^-$ NK cells from wt and miR-155 tg mice were left untreated or stimulated with IL-2 (90 ng/ml) or IL-15 (100 ng/ml) for 10 minutes. Immunoblot analysis was performed on total lysates using anti-phospho-Erk$^{Thr202/Tyr204}$, anti-phospho-Akt$^{Ser473}$ and Grb2 Abs.

FIG. 25C: NK.1$^+$CE3$^-$ NK cells from wt and miR-155 tg mice and paraformaldehyde-treated YAC-1 cells were mixed and incubated at ratio 5:1 for the indicated times. Lysates from NK and YAC-1 samples were analyzed by immunoblot using anti-phospho-Erk$^{Thr202/Tyr204}$ and Actin Abs. These blots are representative of at least two independent experiments.

DETAILED DESCRIPTION OF THE PREFERRED EMBODIMENT(S)

Figure 1B:
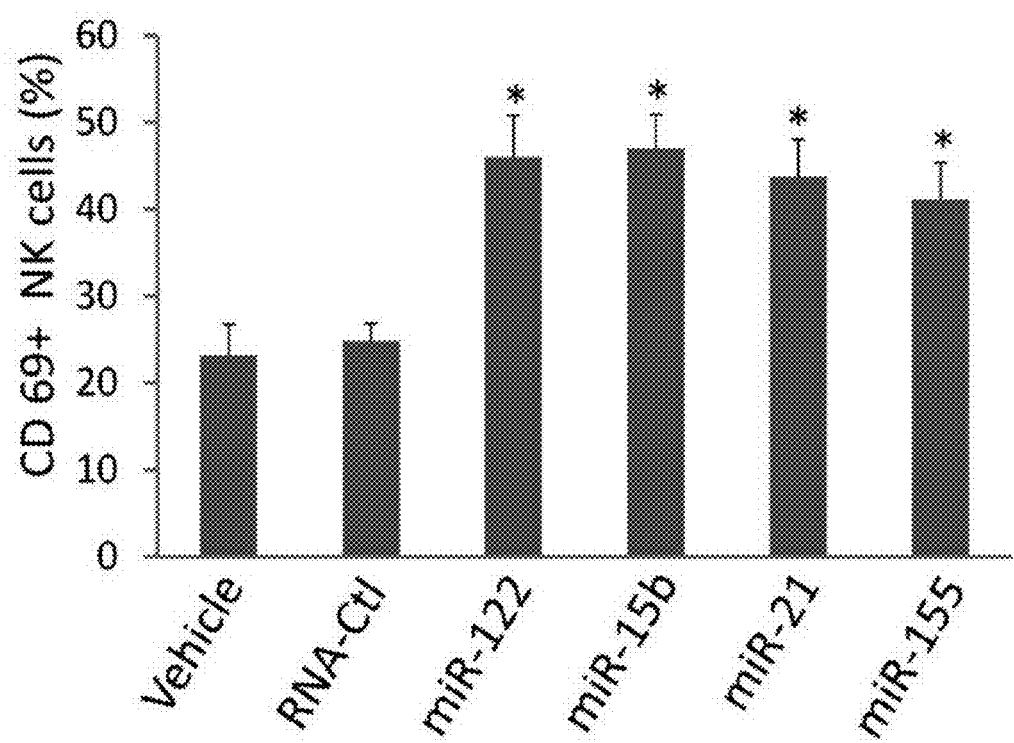

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

For convenience, certain terms employed in the specification, examples, and appended claims are collected here, before further description of the invention. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "plurality" means more than one.

The terms "comprise" and "comprising" are used in the inclusive, open sense, meaning that additional elements may be included.

The term "including" is used to mean "including but not limited to." "Including" and "including but not limited to" are used interchangeably.

The term "wt" means "wild type."

MicroRNAs Activate Natural Killer Cells through Toll-Like Receptor Signaling

MicroRNAs (miRNAs) bind to complementary sequences of target mRNAs, resulting in translational repression or target degradation and thus gene silencing. MiRNAs are abundant in circulating blood, yet it has not been clear whether, as a class of regulatory molecules, they interact with human natural killer (NK) cells.

As shown in the examples herein, the treatment of human NK cells with several mature miRNAs, in the presence of a low concentration of interleukin-12, induces CD69 expression, interferon-γ production, and degranulation marker CD107a expression. In vivo, infusion of several miRNAs alone in murine peripheral blood also results in comparable NK-cell activation, but not T-cell activation. Furthermore, miRNA administration significantly protects mice from tumor development in an NK cell-dependent manner. Mechanistically, miRNA stimulation leads to downstream activation of nuclear factor κB (NF-κB), an effect that is blunted by a block in Toll-like receptor 1 (TLR1) signaling and attenuated in lymphoma patients. Knockdown of TLR1 results in less activation by miRNAs. In accordance with the present disclosure, miRNAs have a capacity to selectively activate innate immune effector cells, at least in part, via the TLR1NF-κB signaling pathway. This is important in the normal host defense against infection and/or malignant transformation.

Natural killer (NK) cells are an important component of innate immunity in that they often provide the first line of defense against malignant transformation and viral infection. Certain miRNAs are expressed by NK cells and intrinsically regulate their function and development. However, there remained a need to determine whether extrinsic or circulating miRNAs are able to activate NK cells. Provided herein are examples, using both in vitro and in vivo approaches, in which synthetic circulating miRNAs and miRNA-containing exosomes freshly isolated from healthy donors are shown to have a capacity to activate NK cells. Without wishing to be bound by theory, it is believed this occurs via a Toll-like receptor (TLR) signaling pathway. The results demonstrate a role for miRNAs in the innate immune response.

As shown herein, the activation induced by miRNAs is relatively specific for innate immune effector cells (i.e., NK cells) and absent in T cells, both in vitro and in vivo. This finding is useful when selective activation of these relatively distinct arms of the immune response is desired. For example, in the setting of blood and marrow transplantation, the NK-cell innate immune response can function to kill activated T cells, thereby contributing to the suppression of donor T-cell-mediated graft-versus-host disease.

In the examples herein, NK-cell activation noted in the presence of miRNAs was confirmed as not due to nonspecific binding and activation by contaminants. High-performance liquid chromatography purified RNA negative control was prepared and handled in an identical fashion to the miRNAs, making it unlikely that NK-cell activation in response to the miRNAs was the result of endotoxin or other contaminants. With regard to the RNA control, a nonspecific, single-stranded RNA called RNA41, which is similar in size to miRNAs, was used in the majority of in vitro experiments, and no induction of IFN-γ or CD107a degranulation was seen. Further, to rule out the potential bias due to the use of a single RNA (RNA41) as a control, several nt of miR-122 and miR-15b were mutated, and all NK-cell activation was subsequently lost.

In addition to uses of miRNAs for cancer diagnosis and prognosis, miRNAs are useful for therapeutic applications. The findings described herein demonstrate that those miRNAs that function as tumor suppressors, such as miR-122, are useful agents for the treatment of cancer. These miRNAs directly and specifically target oncogene expression, yet are also able to activate innate immune effector cells against tumor cells. This discovery also explains the manner in which the host mounts an immune response against infectious pathogens and/or malignant transformation, as well as the manner by which tumors or pathogens edit the immune response to escape immune activation by circulating miRNAs.

The examples herein demonstrate that miRNAs, as a class of regulatory molecules, directly activate both human and mouse NK cells, and this NK-cell activation occurs, at least in part, via the TLR1 signaling pathway. This identifies a function of miRNAs with physiological relevance, and shows their usefulness for applications in preventing or treating cancer and infections either alone or as an adjuvant. Thus, described herein are various methods and compositions useful for treating diseases or disorders including, but not limited to: cancers such as lymphoma or leukemia, infections, and inflammation.

Combination Therapies

In certain embodiments, the miRNAs described herein can be administered in combination with other anti-cancer agents, anti-inflammatory agents, or anti-infective agents. Suitable other anti-cancer agents, include, but are not limited to: chemotherapeutic agents; cytotoxins; antimetabolites; alkylating agents; protein kinase inhibitors; anthracyclines; antibiotics; antimitotic agents (e.g. antitubulin agents); corticosteroids; radiopharmaceuticals; proteins such as cytokines, enzymes, or interferons; biological response modifiers such as krestin, lentinan, sizofiran, picibanil, ubenimex; anti-angiogenic compounds such as acitretin, fenretinide, thalidomide, zoledronic acid, angiostatin, aplidine, cilengtide, combretastin A-4, endostatin, halofuginone, rebimastat, removab, Revlimid, squalamine, ukrain, or Vitaxin; platinum-coordinated compounds such as cisplatin, carboplatin, nedaplatin, or oxaliplatin; camptothecin derivatives such as camptothecin, 10-hydroxycamptothecin, 9-aminocamptothecin, irinotecan, SN-38, edotecarin, or topotecan; compounds or chelates that include radionuclides; or combinations thereof. Examples of suitable interferons include, but are not limited to interferon alpha, interferon alpha-2a, interferon, alpha-2b, interferon beta, interferon gamma-1a, interferon gamma-1b (Actimmune), interferon gamma-n1, or combinations thereof.

In certain embodiments, the anticancer agent is one or more of filgrastim, lentinan, sizofilan, TheraCys, tibenimex, WF-10, aldesleukin, alemtuzumab, BAM-002, dacarbazine, daclizumab, denileukin, gemtuzumab ozogamicin, ibritumomab, imiquimod, lenograstim, lentinan, Corixa, molgramostim, OncoVAX-CL, sargramostim, tasonermin, tecleukin, thymalasin, tositumomab, Virulizin, Z-100, epratuzumab, mitumomab, oregovomab, pemtumomab (Y-muHMFG1), Provenge (Dendreon), alitretinoin, ampligen, atrasentan bexarotime, bortezomib. Bosentan, calcitriol, exisulind, finasteride.fotemustine, ibandronic acid, miltefosine, mitoxantrone, 1-asparaginase, procarbazine, dacarbazine, hydroxycarbamide, pegaspargase, pentostatin, tazarotne, Telcyta (TLK-286, Telik Inc.), Velcade (bortemazib, Millenium), tretinoinor, or combinations thereof.

Suitable anti-inflammatory agents include, but are not limited to: glucocorticoids, disodium cromoglycate, nedcromil sodium, acetyl salicylic acid, methyl salicylate, sodium salicylate, phenylbutazone, oxyphenbutazone, apazone, indomethacin, sulindac, tolmetin, mefenamic acid, ibuprofen, naproxen, fenoprofen, flurbiprofen, and ketoprofen. Suitable anti-infective agents include, but are not limited to: penicillins, cephalosporins, macrolides, sulfonamides, quinlones, aminoglycosides, beta lactam antibiotics, linezolid, vancomycin, ketolides, macrolides, amphotericin B, azole antifungals, amylmetacresol, benzalkonium, cetylpyridinium, chlorhexidine, dequilinium, domiphen, dichlorobenzyl alcohol, phenol, tyrothicin, and antiseptics such as iodine.

When administered in combination with another anti-cancer agent, anti-inflammatory agent, or anti-infective agent, the microRNA and other agent can be administered sequentially or simultaneously. In embodiments wherein the administration is sequential, there can be a waiting period between administrations. Additionally, the microRNA and other agent can be administered in cycles in which the order of administration may vary or remain constant.

Pharmaceutical Compositions

The miRNAs of the present disclosure can be incorporated into pharmaceutical compositions for use in the treatment of various diseases. In certain embodiments, miR-122, miR-15b, miR-21, and miR-155 are especially useful in pharmaceutical compositions to treat or prevent certain cancers.

A pharmaceutical composition as described herein may be formulated with any of the miRNAs described herein, plus any common excipients, diluents, or carriers. In certain embodiments, the compositions further comprise an interleukin such as IL-2, IL-12, IL-15, IL-18, IL-20, or a combination thereof. The compositions can be compressed into tablets, or formulated as elixirs or solutions for convenient oral administration or administration by intramuscular or intravenous routes. The compounds can be administered transdermally and may be formulated as sustained release dosage forms and the like.

Figure 18:
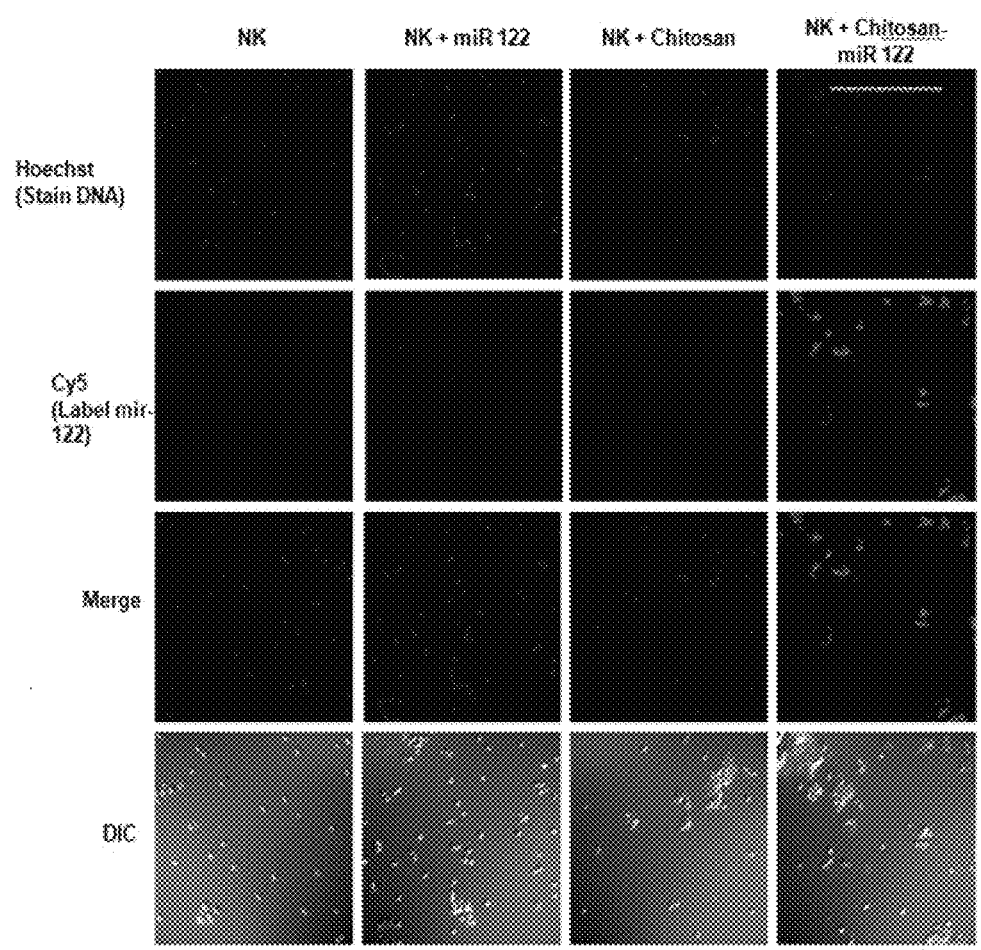
FIG. 18: NK cell uptake experiment of chitosan-miR-122 nanoparticle.

In certain embodiments, the compositions are formulated for delivery via nanoparticles. By way of a non-limiting example, such nanoparticles include, but are not limited to, chitosan nanoparticles. Chitosan is a linear polysaccharide usually produced from shrimp and other crustacean shells. In certain embodiments, as shown in FIG. 18, chitosan nanoparticles effectively deliver miRNAs into NK cells.

The miRNAs, compositions, and formulations provided herein are useful for treating animals, such as humans, for various diseases. A method of treating a human patient according to the present disclosure includes the administration of an effective amount of a miRNA or pharmaceutical composition comprising a miRNA. The miRNA(s) can be formulated into compositions which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to about 50 mg in the case of parenteral or inhalation administration, and from about 25 to about 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in light of all the relevant circumstances including the condition to be treated, the choice of compound to be administered, and the choice of route of administration. Therefore, the dosage ranges discussed herein are not intended to limit the scope of the present invention in any way.

The formulations useful for separate administration of the miRNAs normally contain at least one miRNA (which may be referred to herein as the active ingredient or active substance) mixed with a carrier, or diluted by a carrier, or enclosed or encapsulated by an ingestible carrier in the form of a capsule, sachet, cachet, paper, or other container, or by a disposable container such as an ampoule. A carrier or diluent may be a solid, semi-solid or liquid material which serves as a vehicle, excipient, or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium, or calcium stearates, talc, or mineral oil.

In certain embodiments, pharmaceutical compositions of the present disclosure comprise an effective amount of a miRNA selected from the group consisting of miR-122, miR-15b, miR-21, and miR-155, and/or additional agents, dissolved or dispersed in a pharmaceutically acceptable carrier. The phrases "pharmaceutical" or "pharmacologically acceptable" refers to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, and general safety and purity standards as required by FDA Office of Biological Standards.

A composition disclosed herein may comprise different types of carriers depending on whether it is to be administered in solid, liquid or aerosol form, and whether it needs to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The miRNAs of the present disclosure are generally effective over a wide dosage range. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active ingredient. In other embodiments, an active compound may comprise between about 2% to about 75% of the weight of the unit, or between about 25% to about 60%, for example, and any range derivable therein. Naturally, the amount of active ingredient(s) in each therapeutically useful composition may be prepared in such a way that a suitable dosage will be obtained in any given unit dose of the ingredient. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, or they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). The form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, such as, but not limited to, sugars or sodium chloride. Prolonged absorption of the injectable compositions can be brought about by the use in the compositions of agents delaying absorption such as, for example, aluminum monostearate, or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. Sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays have been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

Preferred pharmaceutical forms of the present invention are capsules, tablets, suppositories, injectable solutions, creams, and ointments. Especially preferred forms are formulations for injection, or ingestion, or delivery via nanoparticles or liposomes. Oligonucleotides, such as the microRNAs of the present disclosure, can be formulated in microparticles or nanoparticles. Liposomes can also be used as a delivery vehicle, and a wide variety of suitable liposome delivery systems exist. By way of a non-limiting example, suitable liposome delivery systems may comprise cationic lipids or neutral lipids. The size of suitable liposomes may be varied for various purposes, and other components may be included in the liposomes or on the surface of the liposomes.

Chitosan nanoparticles can be used for delivery of the miRNAs presently described. Other suitable polymers for delivery include, but are not limited to, polyethyleneimine (PEI), cyclodextrin, atelocollagen, polyamidoamine (PA-MAM), and poly(lactic-co-glycolic acid) (PLGA). Furthermore, the miRNAs of the present disclosure can be conjugated to cationic peptides that have been shown to facilitate transport into cells. The miRNAs can also be conjugated to lipids to facilitate delivery. In particular, cholesterol conjugation can be used to improve delivery.

In certain embodiments, one or more of the miRNAs described herein can be formulated in a pharmaceutical composition as an adjuvant. By way of a non-limiting example, the miRNAs are useful as adjuvants in compositions for the treatment or prevention of cancer or infection. The miRNAs can be adjuvants in a composition with any of the anti-cancer agents, anti-inflammatory agents, or anti-infective agents described above.

Kits

It is further intended the compositions disclosed herein could be packaged in the form of a kit containing multiple containers. Many embodiments of such kits are possible. By way of non-limiting example, a kit could include multiple components for preparing a pharmaceutically composition. In certain embodiments, a kit comprises a first container housing a miRNA selected from the group consisting of miR-122, miR-15b, miR-21, and miR-155, and a second container housing a pharmaceutically acceptable carrier, diluent, or excipient. In certain embodiments, the pharmaceutically acceptable carrier, diluent, or excipient comprises nanoparticles or a liposomal formulation. In certain embodiments, the kits further comprise a third container housing a cytokine. Many other variations and embodiments of kits are envisioned.

The kits typically further include instructions for using the components of the kit to practice the subject methods, but do not need to include such instructions. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a CD-ROM, diskette, or flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Certain embodiments of the present invention are defined in the examples herein. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example I miRNAs Activate NK Cells through a TLR-NF-κB Signaling Pathway and Have Therapeutic Applications in Cancer In this example, several miRNAs previously demonstrated to be present in the circulation, including miR-122, miR-15a, miR-21, and miR-155, were synthesized. The synthesized miRNAs were placed in culture with highly purified human NK cells. Alone, each of these miRNAs was unable to activate NK cells. However, when placed in culture for 36 hours in the presence of a low concentration of IL-12 (2.5 ng/ml), a two- to three-fold increase in the surface expression of CD69 for each miRNA was observed. In contrast, a non-specific, single-stranded control RNA similar in size to the miRNAs, RNA41, did not significantly induce CD69 surface expression. Similarly results were also obtained with either a longer (72 hours) or shorter (24 hours) exposure.

Materials and Methods

Cell Culture

Primary human NK cells, human peripheral blood mononuclear cells (PBMCs), and mouse spleen cells were cultured in complete RPMI 1640 media (Invitrogen) containing 10% fetal bovine serum (FBS), penicillin (100 U/mL), and streptomycin (100 μg/mL). Cells were cultured at 37 °C. and supplemented with 5% carbon dioxide. The human interleukin (IL)-2-dependent NK cell line NK-92, a generous gift of Dr. Hans G. Klingemann (Rush University Medical Center, Chicago, Ill.), was cultured similarly, except that 20% FBS was used.

Mice

Eight-week-old C57BL/6 and athymic nude mice were obtained from the Jackson Laboratory. The Ohio State University Animal Care and Use Committee approved all animal work.

Human NK-Cell Isolation

Figure 8:
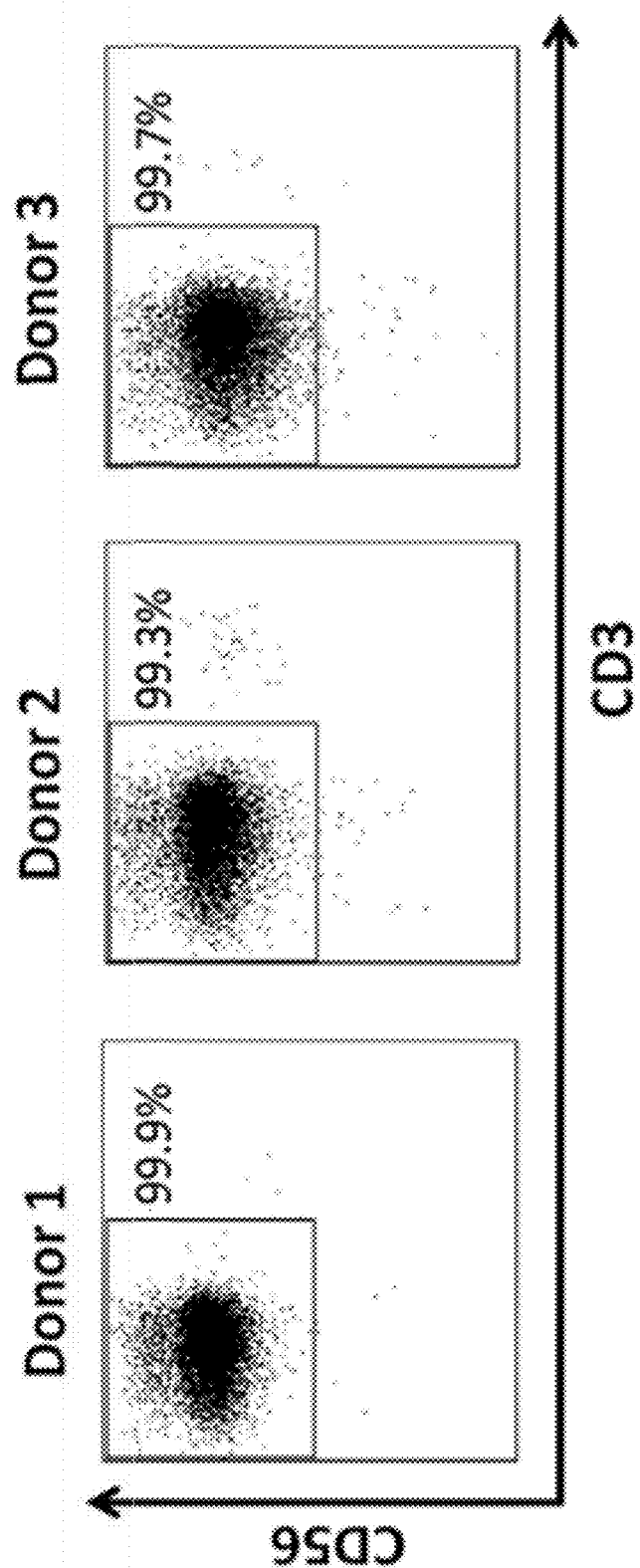
FIG. 8: Purification of human NK cells. Flow data from 3 representative donors indicate that NK purity is ≥99% following negative enrichment with RosetteSep and positive selection with anti-CD56 MACS beads.

Human NK cells were first enriched from the peripheral blood of healthy donors (American Red Cross) with the RosetteSep NK-cell enrichment mixture (StemCell Technologies) and Ficoll-Paque Plus (Amersham) centrifugation. The enriched NK cells were further purified by positive selection using anti-CD56 magnetic-activated cell sorting beads (Miltenyi Biotec). NK cells with purity greater than 99%, which was confirmed by flow cytometry, were used (FIG. 8). PBMCs from lymphoma patients were first stained with CD3-PE and CD19-PE and subjected to negative selection for NK cells using magnetic-activated cell sorting LS columns (Miltenyi Biotec). The enriched NK cells were then further purified by fluorescence-activated cell sorting (FACS) after being stained with CD3-fluorescein isothiocyanate (FITC) and CD56-allophycocyanin (APC) antibodies (Abs). For healthy donors, PBMCs were directly stained with CD3-FITC and CD56-APC Abs and subjected to sorting for NK cells. The purity of sorted NK cells immediately lysed for real-time reverse transcriptase polymerase chain reaction (RT-PCR) analysis was greater than 97%. All human work was approved by The Ohio State University Institutional Review Board.

Cell Stimulation by miRNAs

Purified human primary NK cells, PBMCs, or freshly isolated mouse splenocytes were resuspended at $1 \times 10^6$ cells/100 μL in complete RPMI 1640 media, then plated on a 96-well plate in the presence of recombinant human (rh) IL-12 (Genetics Institute Inc). MiRNAs were placed in complex with DOTAP, a cationic liposomal formulation (Roche), according to the manufacturer's instruction. Briefly, 2 μg miRNAs were dissolved in 25 μL hepes-buffered saline, combined with 10 μg DOTAP solution in 25 μL hepes-buffered saline, and incubated for 15 minutes. Next, 50 μL of complete RPMI 1640 media were added to the miRNAsDOTAP mixture and mixed well before being added to each well preseeded with cells. The final concentration of DOTAP was 50 μg/mL, and the final concentration of miRNA was 10 μg/mL. Vehicle control for all experiments consisted of 50 μg/mL of DOTAP. RNA control for all experiments consisted of 50 μg/mL of DOTAP complexed with 10 μg/mL of a nonspecific, single-stranded control RNA called RNA41, which is similar in size to miRNA. The cells were stimulated for 36 hours (unless specified) with miRNAs and 2.5 ng/mL rhIL-12. The dose of 2.5 ng/mL rhIL-12 is less than what is typically used for stimulation of NK cells (10 ng/mL). For the TLR blocking assay, the aforementioned cells were preincubated with TLR1 (InvivoGen), TLR3 (Hycult Biotech), or TLR6 (InvivoGen) blocking Abs or control immunoglobulin G (IgG; Equitech Bio) at a concentration of 10 μg/mL for 1.5 hours prior to stimulation with miRNAs. The blocking Abs were also kept in the culture during the stimulation with miRNAs.

Flow Cytometric Analysis

The stimulated cells were stained with monoclonal antibodies (mAbs) at 4° C. for 20 minutes, washed with phosphate-buffered saline (PBS), and fixed with 1% formalin, followed by FACS analysis using an LSRII (BD Bioscience) to detect surface expression of each antigen. Human NK cells were gated as CD56$^+$CD3$^-$ and mouse NK cells were gated as NK1.1$^+$CD3$^-$ cells within the lymphocyte gate. The following anti-human mAbs used were: CD3-FITC, CD56-APC, CD107a-PE, and CD69-PE. The following anti-mouse mAbs used were: CD3-FITC, NK1.1-APC, CD69-PE, and CD107a-PE. All mAbs were purchased from BD Bioscience.

Real-time Reverse-Transcriptase and Enzyme-linked Immunosorbent Assay

Total RNA was extracted and reverse transcribed into cDNA. The interferon (IFN)-γ mRNA expression level was determined by real-time RT-PCR using Taqman PCR Master Mix (Applied Biosystems), while TLRs, p65, and IRAK1 mRNA expression levels were assessed using SYBR Green Master Mix (Applied Biosystems). Expression levels were normalized to an 18S or β-actin internal control and then analyzed by the ΔΔCt method. To detect secreted IFN-γ protein, cells were stimulated with miRNAs and IL-12 as described above, and cell-free supernatants were analyzed by enzyme-linked immunosorbent assay (ELISA) as previously described.

CD107a Degranulation Assay

To detect the capacity of NK cells for cytotoxic activity, human NK cells and murine splenocytes were stimulated in vitro and treated in vivo with miRNAs, respectively. A total of 0.5 million miRNA-stimulated human and murine NK cells were then incubated at the ratio of 1:1 with K562 and YAC-1 target cells, respectively. However, only human NK cells were cocultured with a low concentration (2.5 ng/mL) of IL-12. Subsequently, 2.5 μL anti-human or 1 μL anti-mouse CD107a antibody was added to this coculture for 1 hour. Then, 1 μL/mL of the secretion inhibitor, monensin (eBioscience), was added for an additional incubation of 3 hours. The cells were washed with PBS and stained with CD3 (human and mouse) and CD56 (human) or NK1.1 mAbs (mouse), and then analyzed via flow cytometry using an LSRII.

In Vivo miRNA Stimulation

The complexes of miRNAs and vehicle, Lipofectamine 2000 (Invitrogen), were prepared according to the manufacturer's instruction. Briefly, 30 µL of Lipofectamine 2000 was mixed with 20 µg RNA-Control, miR-122, or miR-15b dissolved in 170 µL PBS. The liposome complexes were administered intravenously (200 µL/mouse) into mice through tail veins. Four days later, the injected mice were sacrificed, and total splenocytes were isolated for degranulation assay or stained with aforementioned mAbs for flow cytometric analysis.

Immunoblotting

Total protein lysates were prepared with T-Per (tissue protein extraction reagent; ThermoScientific) supplemented with proteinase and phosphatase inhibitors. Proteins were resolved on a 4% to 20% SDS-PAGE gel and transferred onto PVDF membranes (Amersham). The Abs used for blotting were TLR1 (Cell Signaling), phospho (p)-p65 (Cell Signaling), p65 (Cell Signaling), and β-actin (Santa Cruz).

TLR1 shRNA Knockdown

A TLR1 short hairpin RNA (shRNA) plasmid was constructed by inserting RNA interference sequences into pSUPER-retrovirus vector expressing green fluorescent protein (GFP). Viruses were prepared by transfecting the shRNA plasmid and packaging plasmids into phoenix cells. Infection was performed. Briefly, NK-92 cells were cocultured with virus-containing media and centrifuged at 1800 rpm at 32° C. for 45 minutes, then incubated for 2 to 4 hours at 32° C. This infection cycle was repeated twice. Upon completion of this infection, GFP-positive cells were sorted on a FACSAria II cell sorter (BD Bioscience). Knockdown of TLR1 in the sorted NK-92 cells was confirmed by immunoblotting.

Bioluminescent Imaging

Balb/C mice-derived A20 B-cell lymphoma cells were retrovirally transduced with a Pinco-pGL3-luciferase (luc)/GFP plasmid, and the GFP-positive cells were sorted by a FACSAria II cell sorter (BD Biosciences). Then, $1 \times 10^5$ luc-expressing A20 cells were injected into each athymic nude mice via tail veins. MiRNAs were administered via a tail-vein injection at the following 3 time points: 3 days prior to, 4 days after, and 18 days after A20 implantation. For NK depletion, each mouse was administered 200 µg TM-β1 (IL-2/15Rβ) mAb intraperitoneally on day 6 prior to and day 3 after A20 cells implantation, 200 µm per time. Three weeks after A20 implantation, mice were injected with luciferin (150 mg/kg body weight; Gold Biotechnology), anesthetized with isoflurane, and imaged using an IVIS-100 imaging system (Xenogen).

Statistics

Data were compared by Student 2-tailed t test. $P<0.05$ was considered statistically significant.

Results

Figure 9:
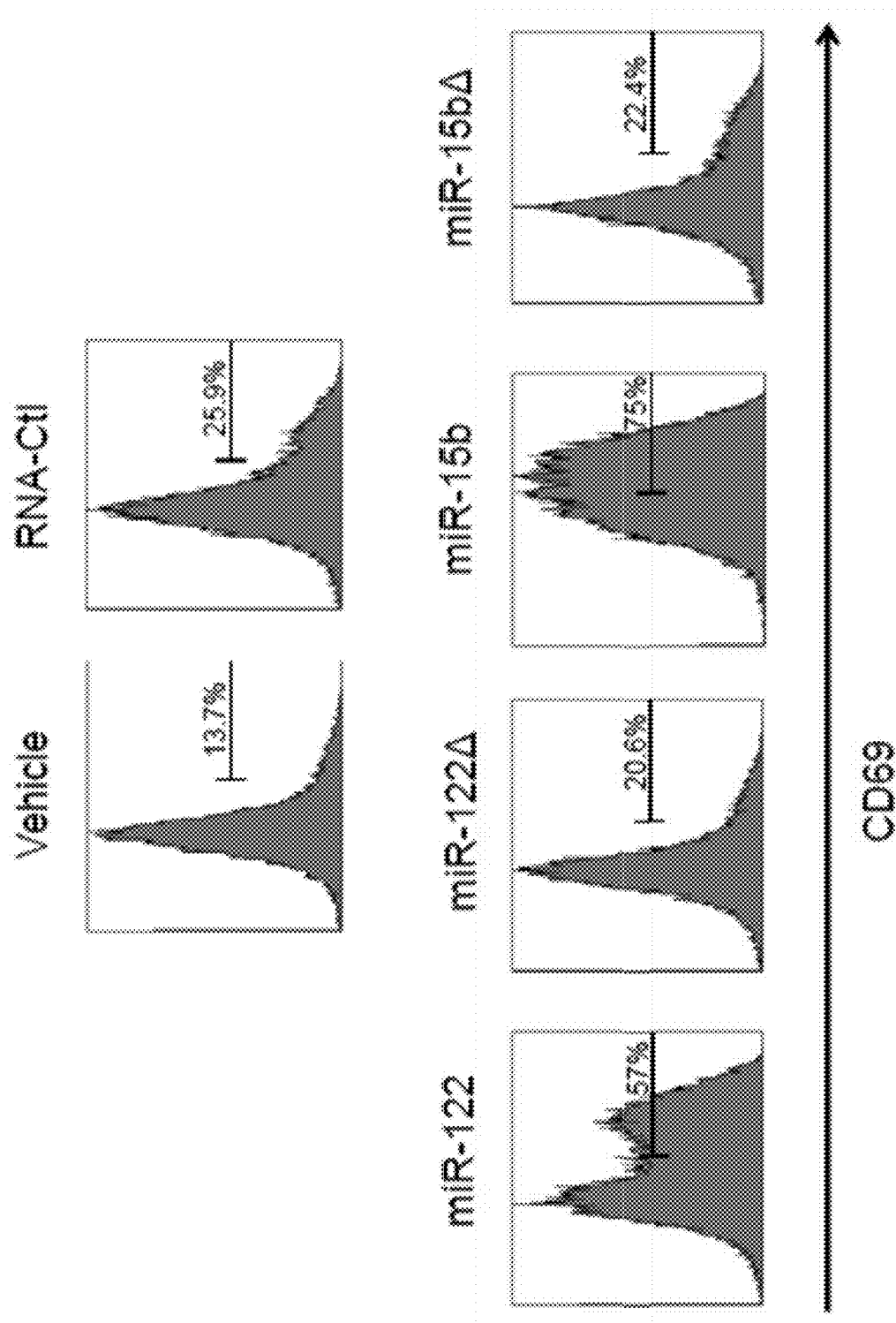
FIG. 9: Mutation of miRNAs significantly impairs NK cell activation induced by miRNAs. MiR-122 and miR-15b mutants were created by substituting uridines (Us) with guanosine (Gs). Purified human NK cells were stimulated with RNA-Ctl (RNU44), WT miR-122, WT miR-15b, mutated miR-122 (miR-122Δ), or mutated miR-15b (miR-15bΔ) for 36 hr in the presence of low-dose IL-12. The stimulated NK cells were then harvested, stained and subjected to flow cytometric analysis to detect CD69 expression.
Figure 10A:
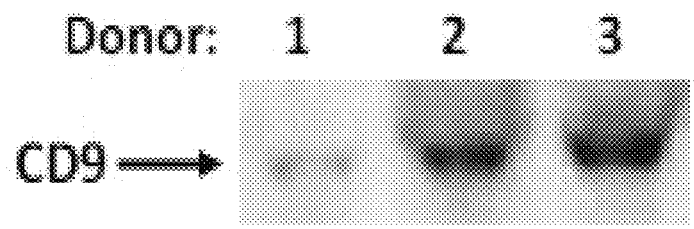
FIGS. 10A-10D: MiRNA-containing exosomes induce NK cell activation ex vivo.
Figure 10B:
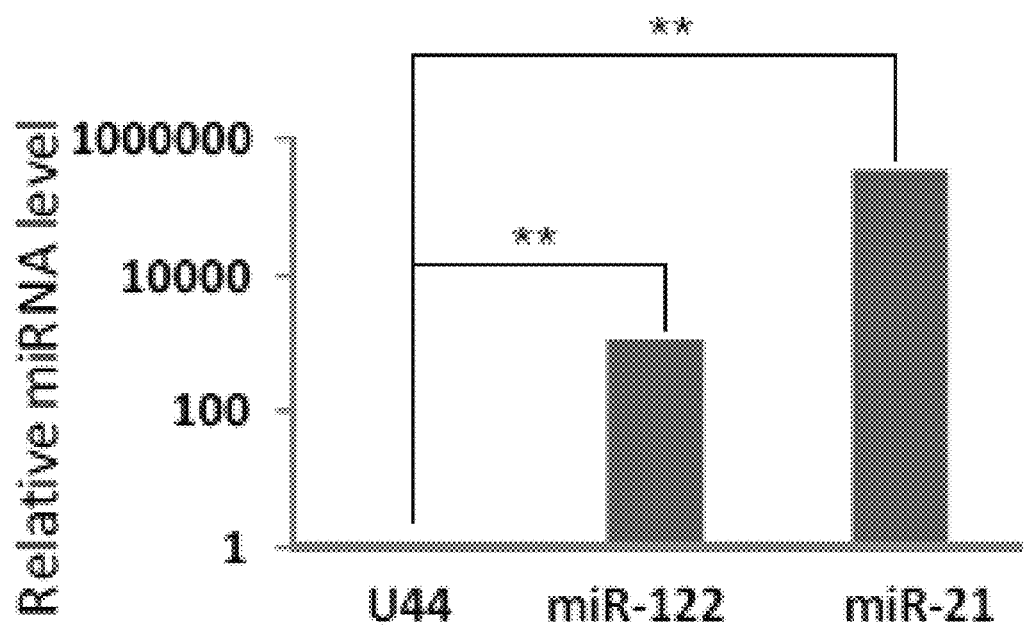
Figure 10C:
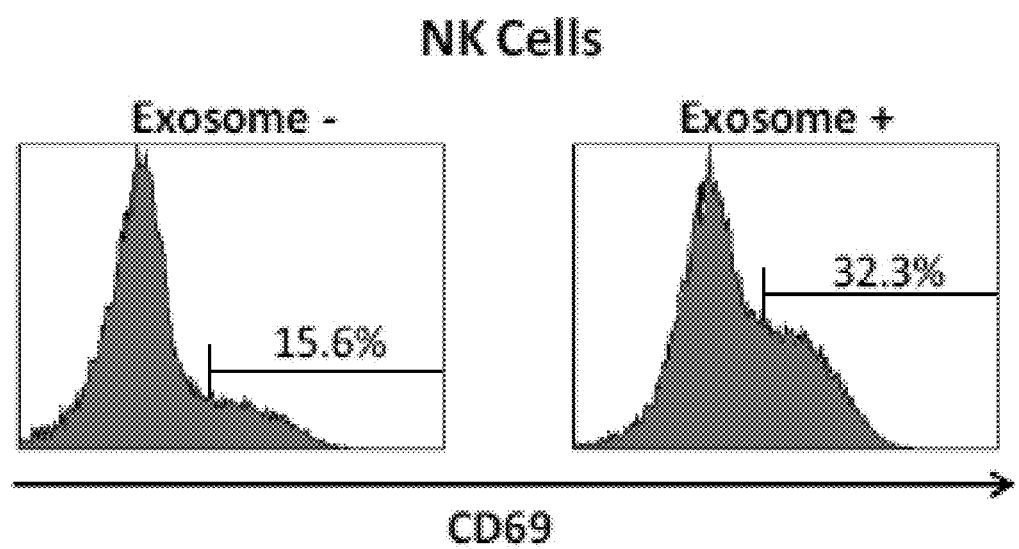
Figure 10D:
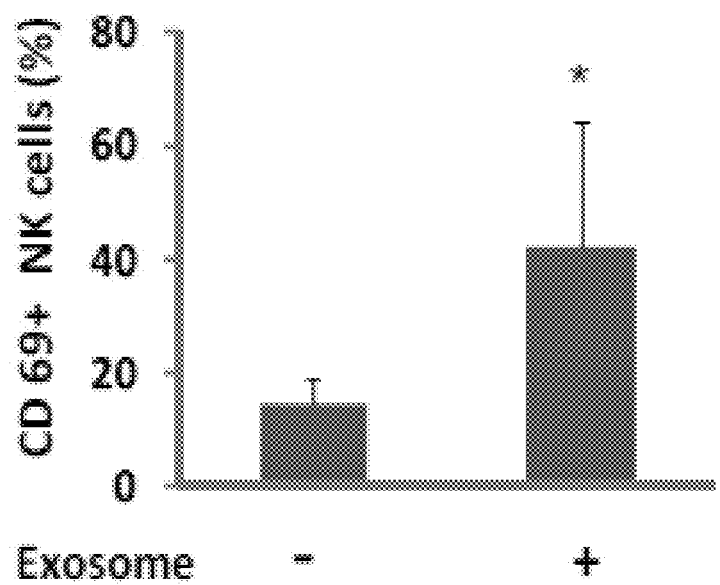

As seen from FIG. 1, the results showed that miRNAs enhance surface expression of the activation marker, CD69, on human NK cells. Several miRNAs previously demonstrated to be present in the circulation were synthesized, including miR-122, miR-15b, miR-21 and miR-155. These synthesized miRNAs were placed in culture with highly purified human NK cells (FIG. 8). Alone, each miRNA was unable to activate NK cells. However, when placed in culture for 36 hours in the presence of a low concentration of IL-12 (2.5 ng/mL), a twofold to threefold increase in the surface expression of CD69 was observed for each miRNA (FIGS. 1A-B). In contrast, a non-specific, single-stranded control RNA terms RNA41, which is of similar size to miRNAs, prepared in an identical fashion, and incubated for an equal amount of time at an identical concentration with human NK cells, did not significantly induce CD69 surface expression (FIGS. 1A-B). Similar results were also obtained with either a longer (72 hours) or shorter (24 hours) exposure. To further verify whether this effect was sequence-specific, miR-122 and miR-15b sequences were mutated by substituting uridine (U) with guanosine (G) in the miRNA sequence. These two mutated miRNAs were found to have completely lost their capability to activate NK cells (FIG. 9).

Consistent with these results, CD-9-expressing exosomes isolated from healthy donor serum and containing relatively high concentrations of miRNAs, such as miR-122 and miR-21, were found to be able to significantly activate NK cells purified from the corresponding (autologous) donors (FIG. 10).

Figure 11:
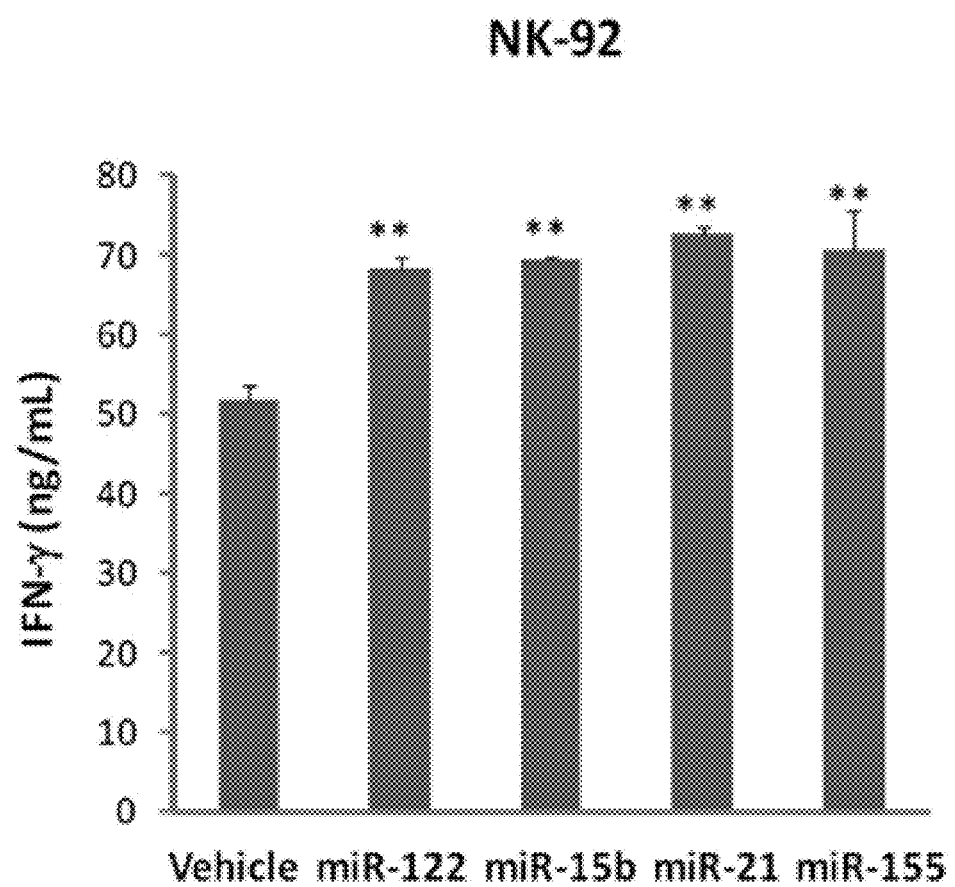
FIG. 11: MiRNAs enhance IFN-γ production by NK-92 cells. NK-92 cells were starved of IL-2 overnight, and were subsequently treated with miRNAs or DOTAP vehicle control for 36 h in the presence of a low dose of IL-12. Supernatants were harvested to measure IFN-γ production via ELISA. Data shown represent 1 of 3 experiments with similar data. ** indicates p <0.01 and error bars represent S.D.
Figure 12A:
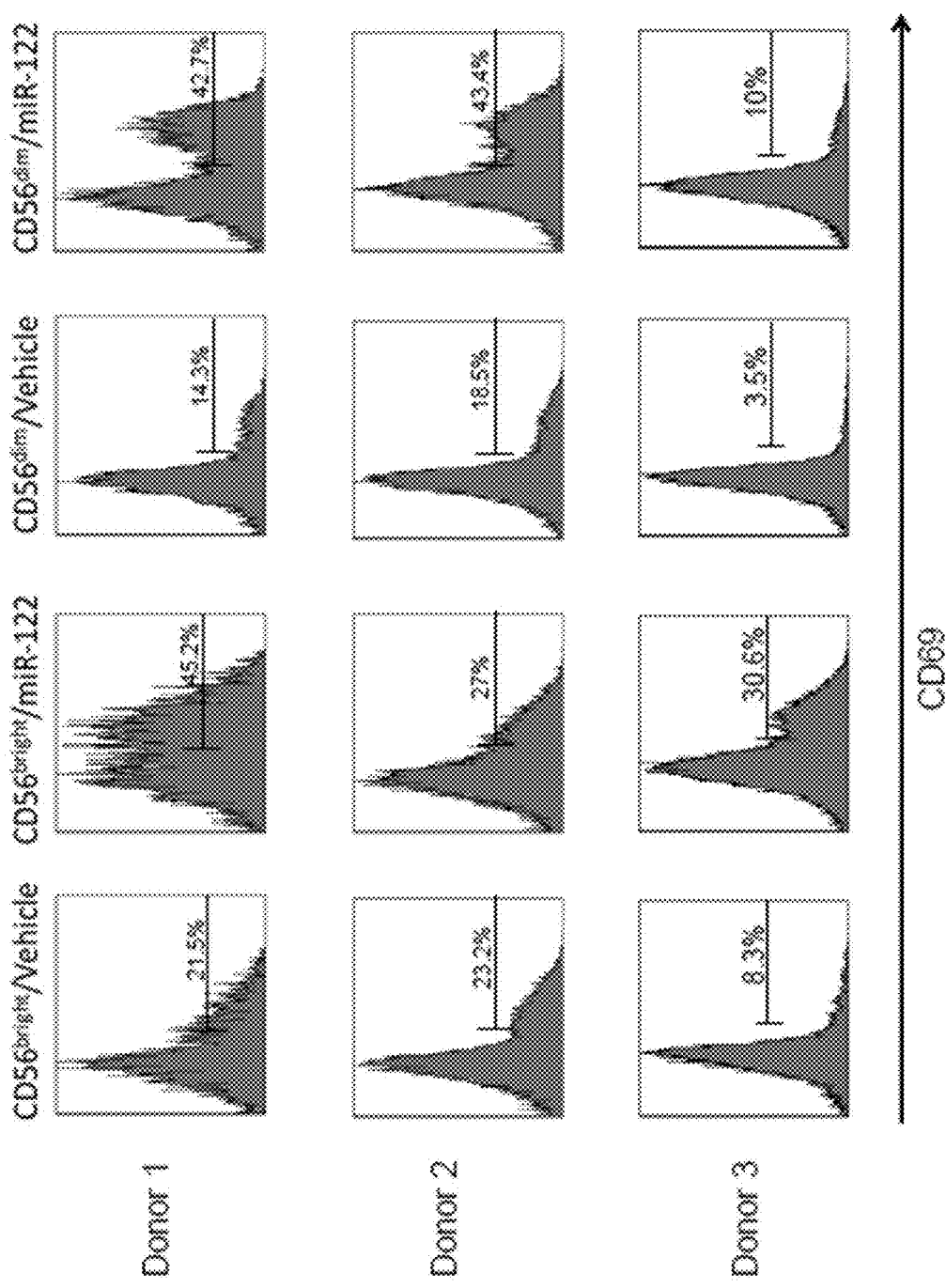
FIGS. 12A-12E: MiRNAs induce activation of both $CD56^{bright}$ and $CD56^{dim}$ NK cells. Highly purified human $CD56^{bright}$ and $CD56^{dim}$ NK cells from different donors were sorted. NK cells were gated as CD3-CD56+. The sorted $CD56^{bright}$ and $CD56^{dim}$ NK cells were then stimulated with vehicle control or miR-122 in the presence of low-dose of IL-12 for 36 hr. The stimulated cells were harvested and subjected to flow cytometric analysis to detect CD69 expression (FIGS. 12A-12C). Cell-free supernatants were also collected to determine the levels of IFN-γ secretion via ELISA (FIGS. 12D-12E).
Figure 12B:
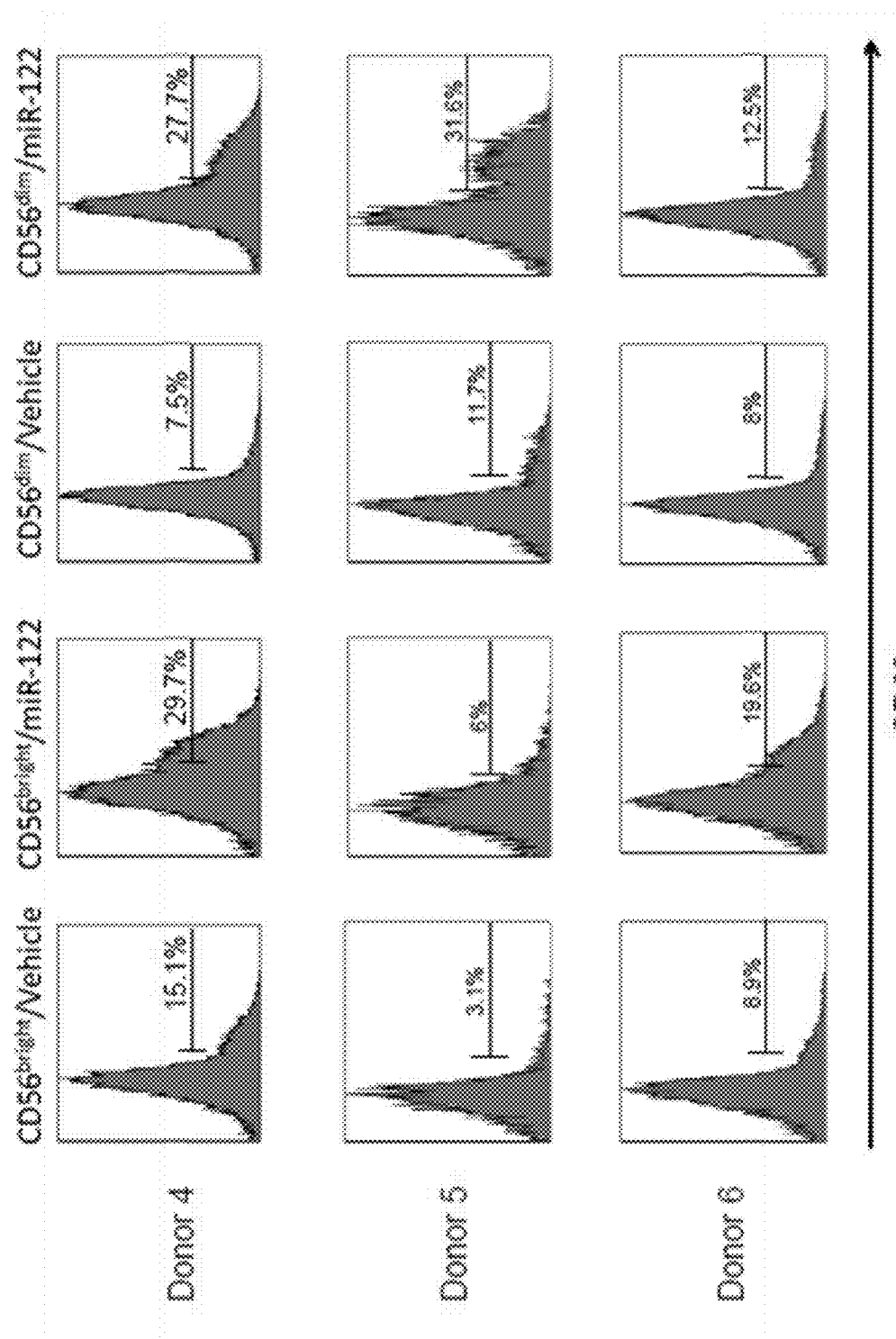
Figure 12C:
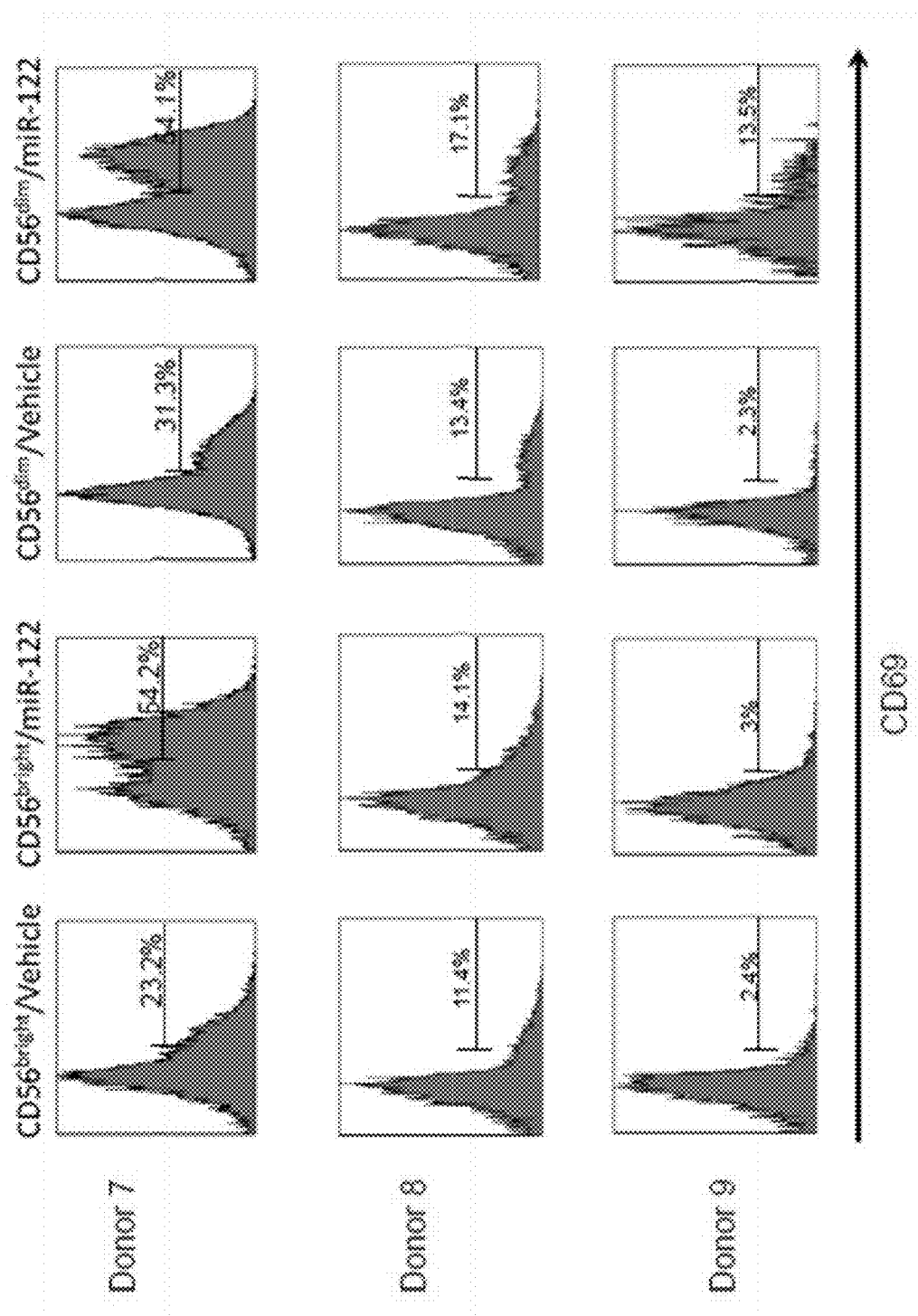
Figure 12D:
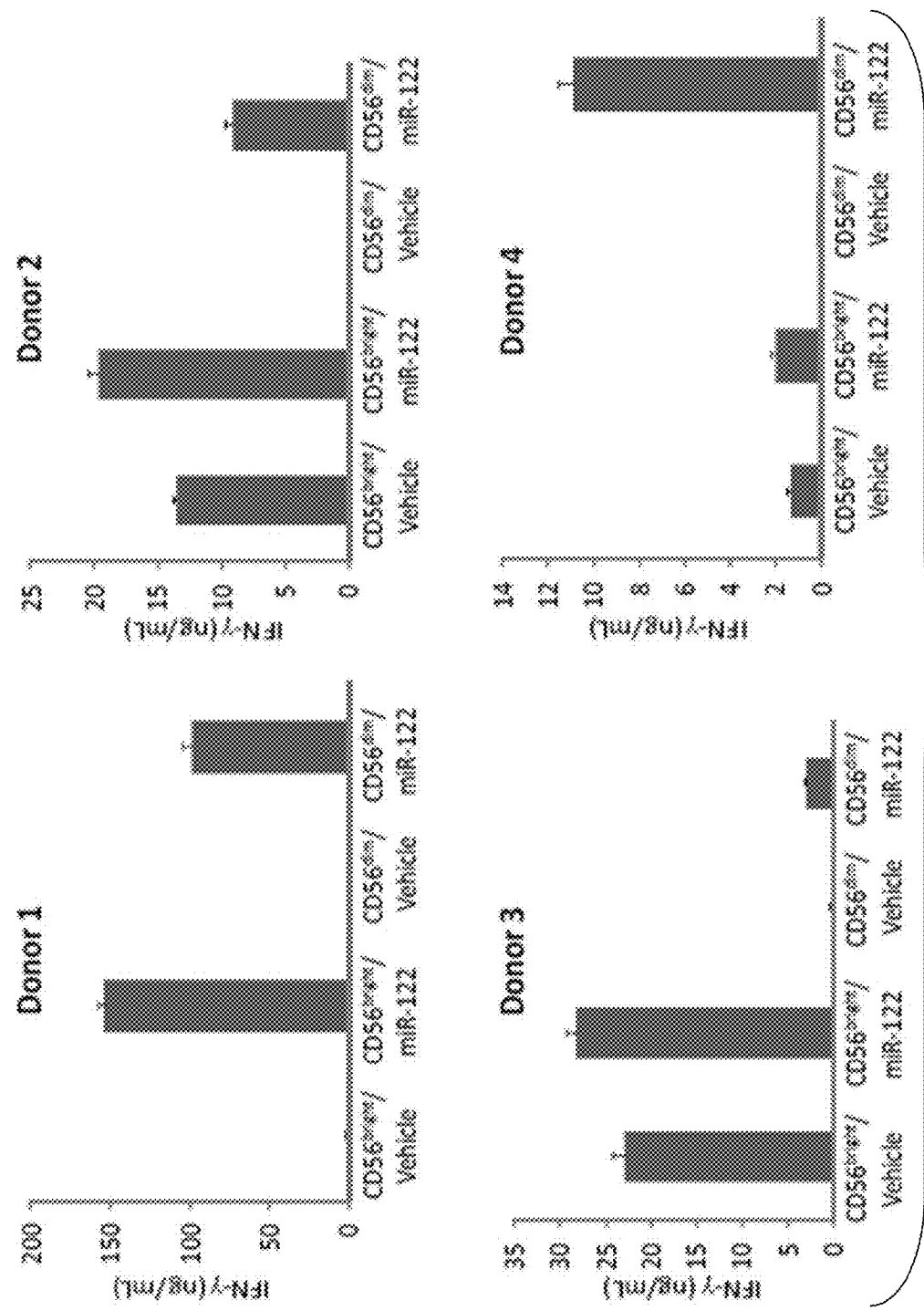
Figure 12E:
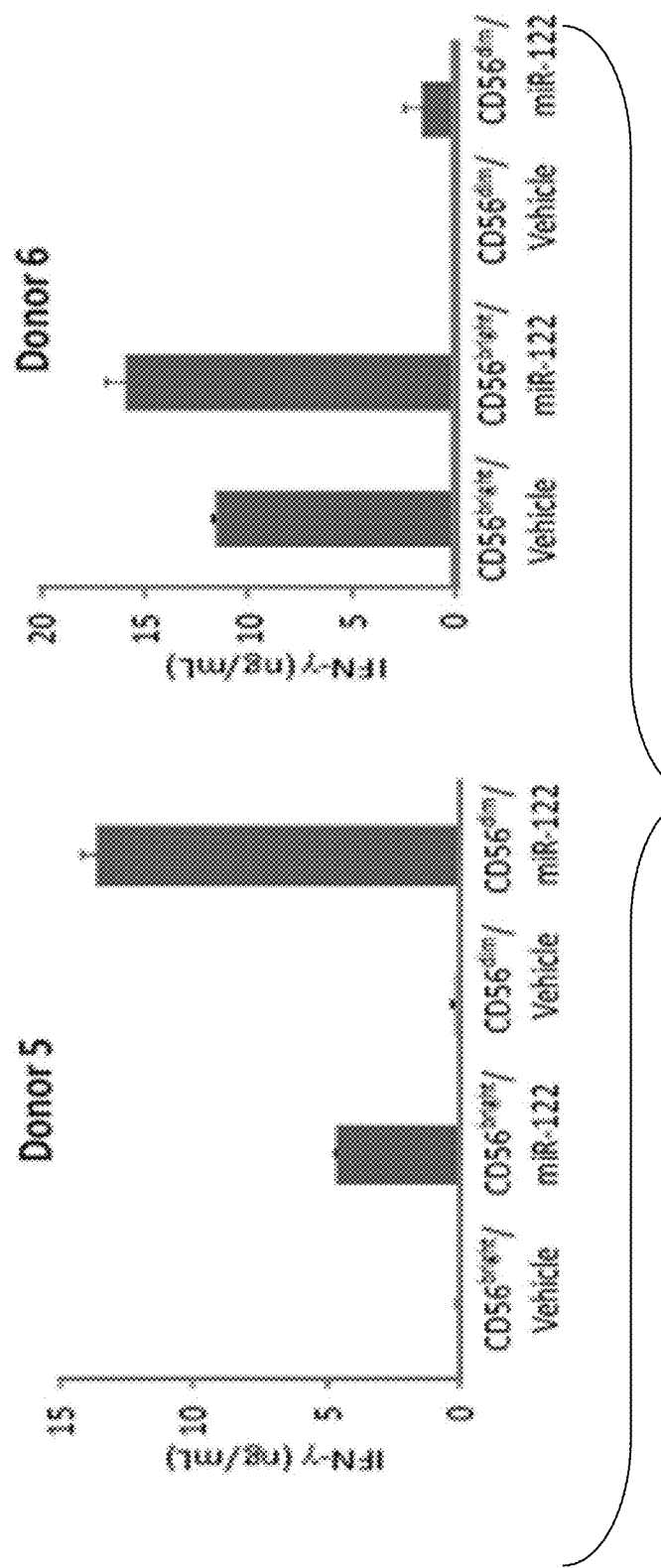

As shown in FIG. 2, treatment with miRNAs augments human NK-cell IFN-γ production and degranulation. Since high expression of activation marker CD69 on NK cells is usually coupled with functional activation, primary human NK cells were assessed for secretion of IFN-γ following miRNA stimulation. Variable but consistently significant increases of IFN-γ protein secretion were observed in each instance (FIG. 2A, upper panel). The data were confirmed by real-time RT-PCR (FIG. 2A, lower panel) and were also found to be dependent of the concentration of miRNAs (FIG. 2D). Similar results were observed in the NK cell line NK-92 (FIG. 11). Although the extent of NK-92 activation was less, most likely due to IL-2 prestimulation of this IL-2-dependent cell line, these data exclude the possibility that the activation of NK cells by miRNAs was caused by contamination of other immune cell subsets. Consistent with the results of CD69 surface expression, the control RNA41 did not induce IFN-γ expression in NK cells (FIG. 2A). Thereafter, only miR-122 and miR-15b were included for experimental conditions in assessing NK-cell activation because of their stronger stimulation of IFN-γ expression when compared with the other 2 miRNAs (miR-21 and miR-155; FIG. 2A).

Upon activation with cytokines, human $CD56^{bright}$ NK cells secrete abundant IFN-γ; in contrast, $CD56^{dim}$ NK cells produce negligible amounts of IFN-γ in response to cytokine stimulation. Notably, upon miRNA stimulation, both $CD56^{bright}$ and $CD56^{dim}$ NK cells became activated, resulting in higher expression of CD69 and IFN-γ secretion when compared with parallel cultures treated with vehicle alone (FIGS. 12A-E).

Figure 2A:
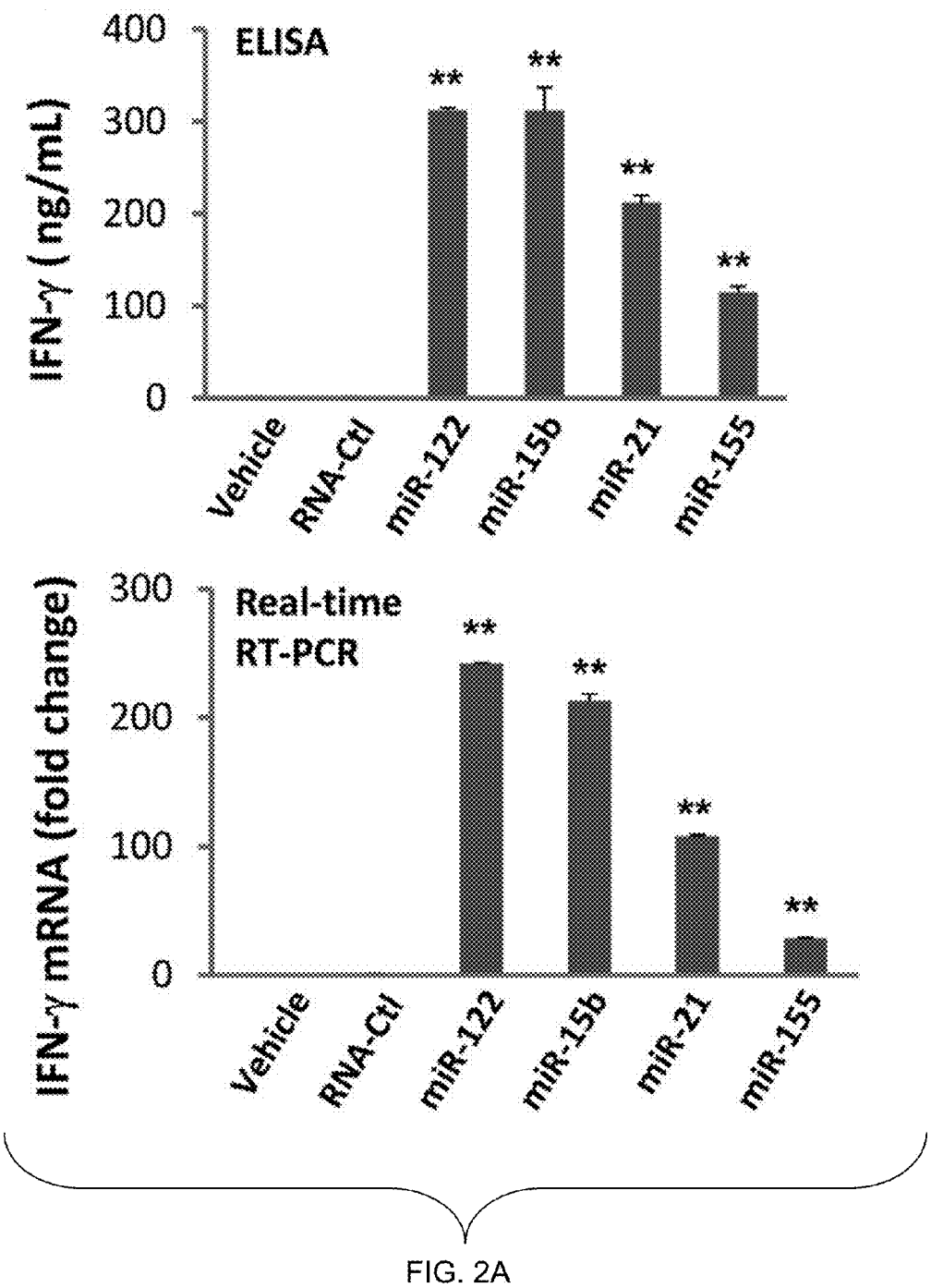
FIGS. 2A-2D: MiRNAs increase IFN-γ production by NK cells.
Figure 2B:
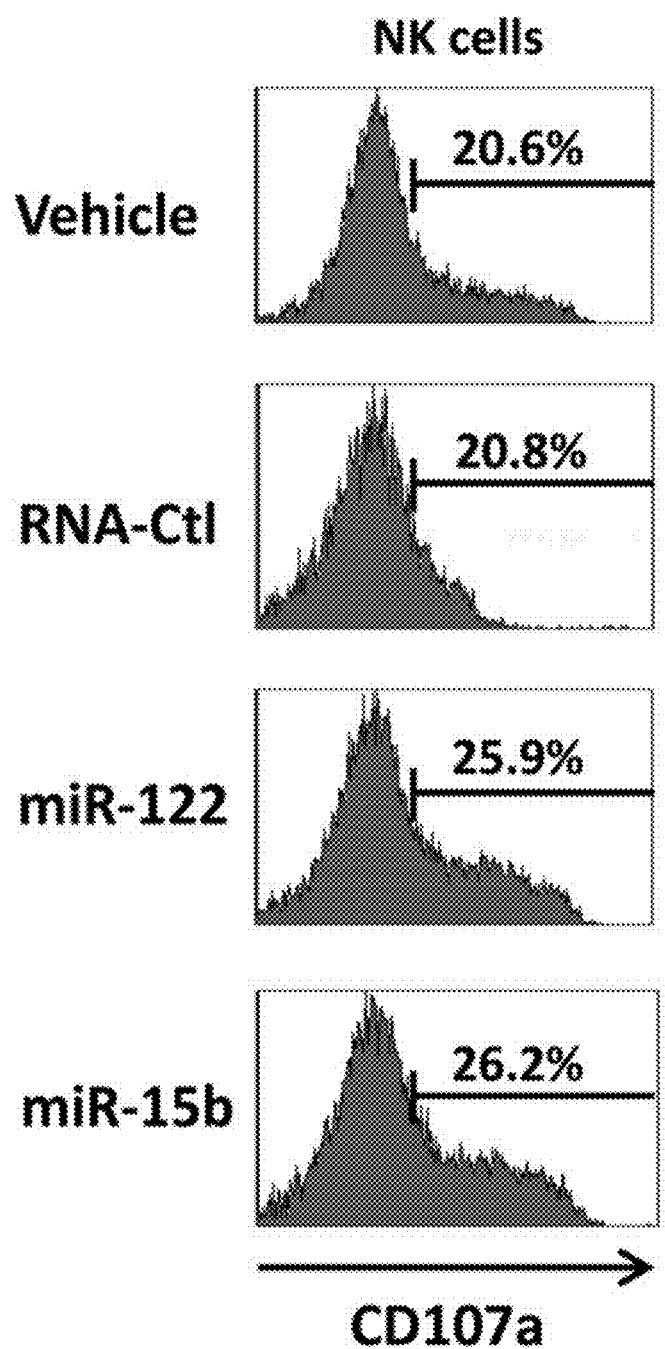
Figure 2C:
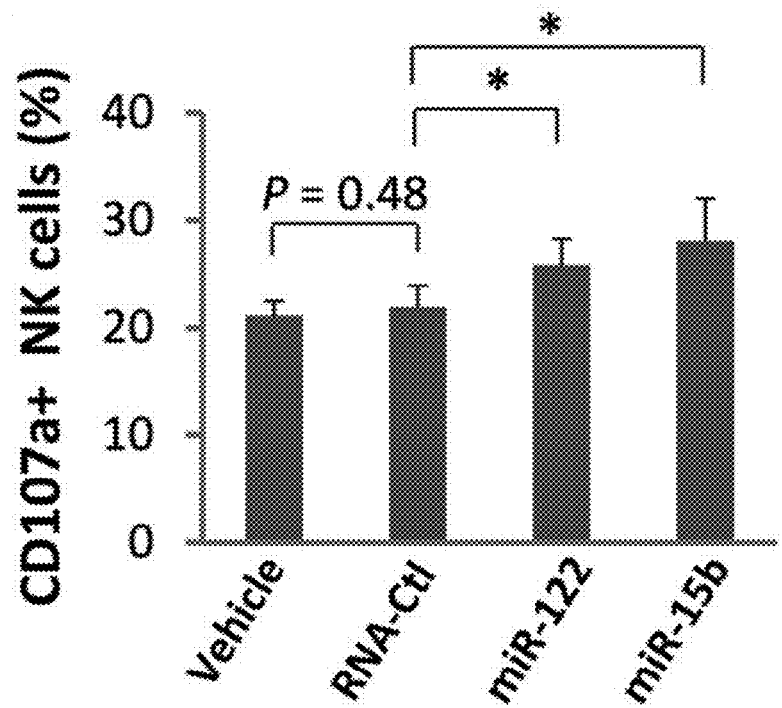
Figure 2D:
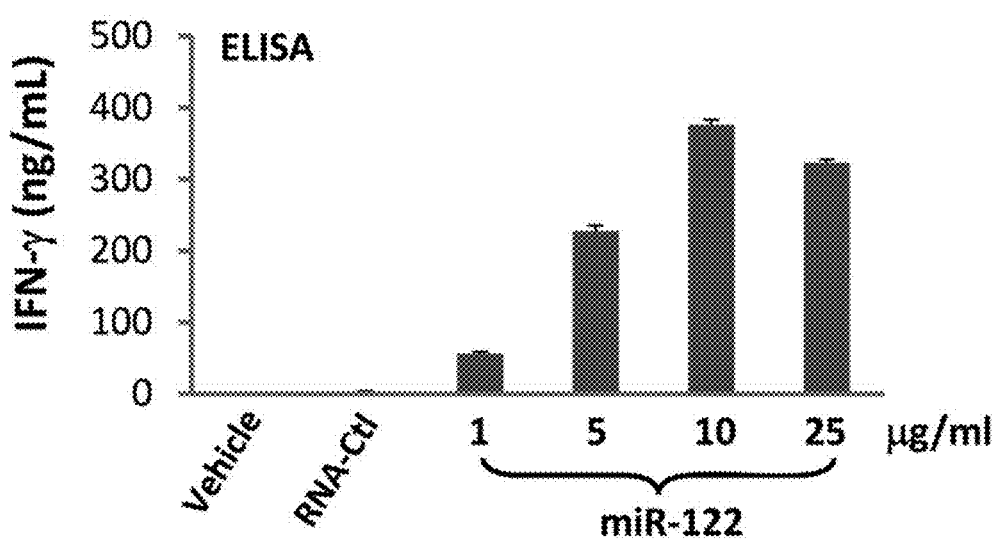

To determine whether miRNAs also stimulate NK-cell cytotoxic effector functions, CD107a expression was measured by a flow cytometric assay to quantify degranulation of primary human NK cells upon contact with K562 tumor cell targets in the presence of IL-12. Compared with the controls, CD107a expression underwent a moderate but statistically significant increase following stimulation with miR-122 and miR-15b (FIGS. 2B-C). A $^{51}$Cr-release cytotoxicity assay with K562 targets was also performed; however, it did not reach statistical significance because of interdonor variation in cytotoxic activity.

Figure 3A:
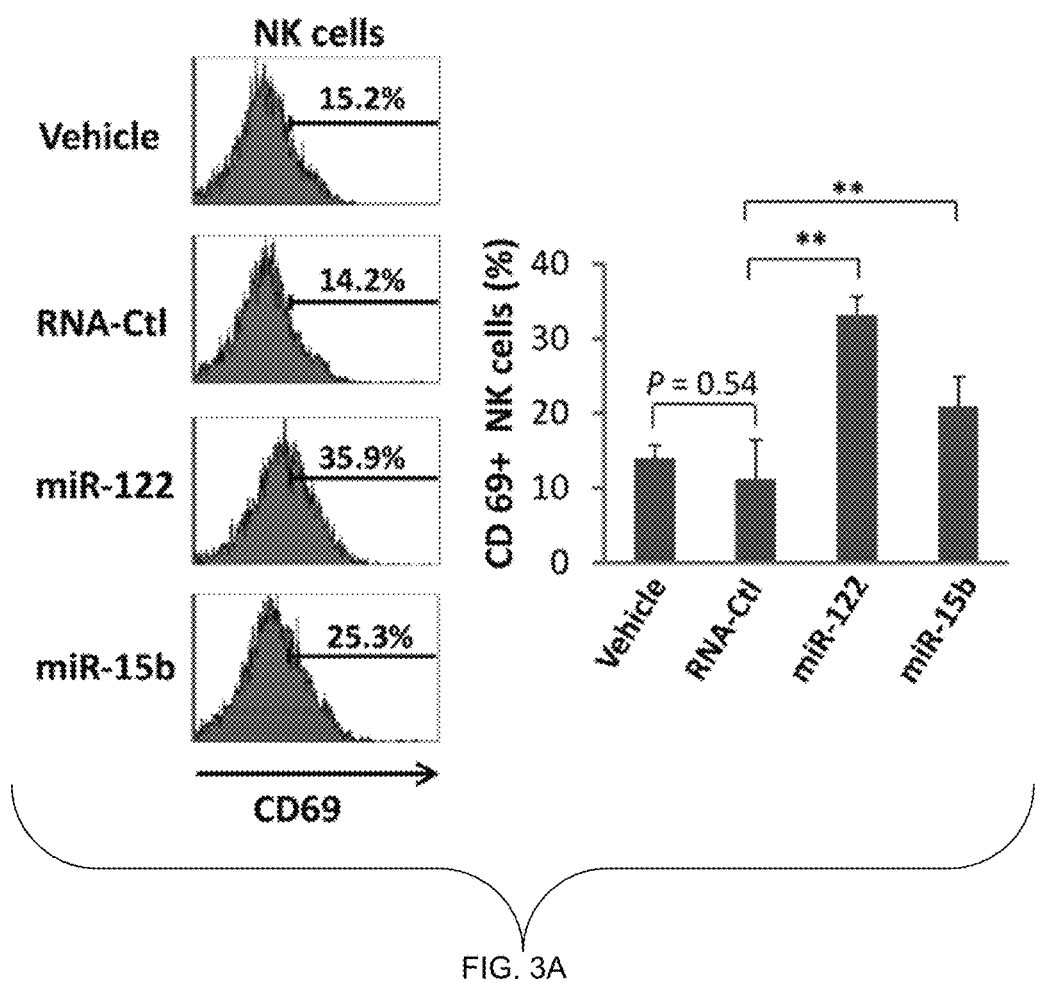
FIGS. 3A-3B: MiRNAs activate NK cells in vivo.
Figure 3B:
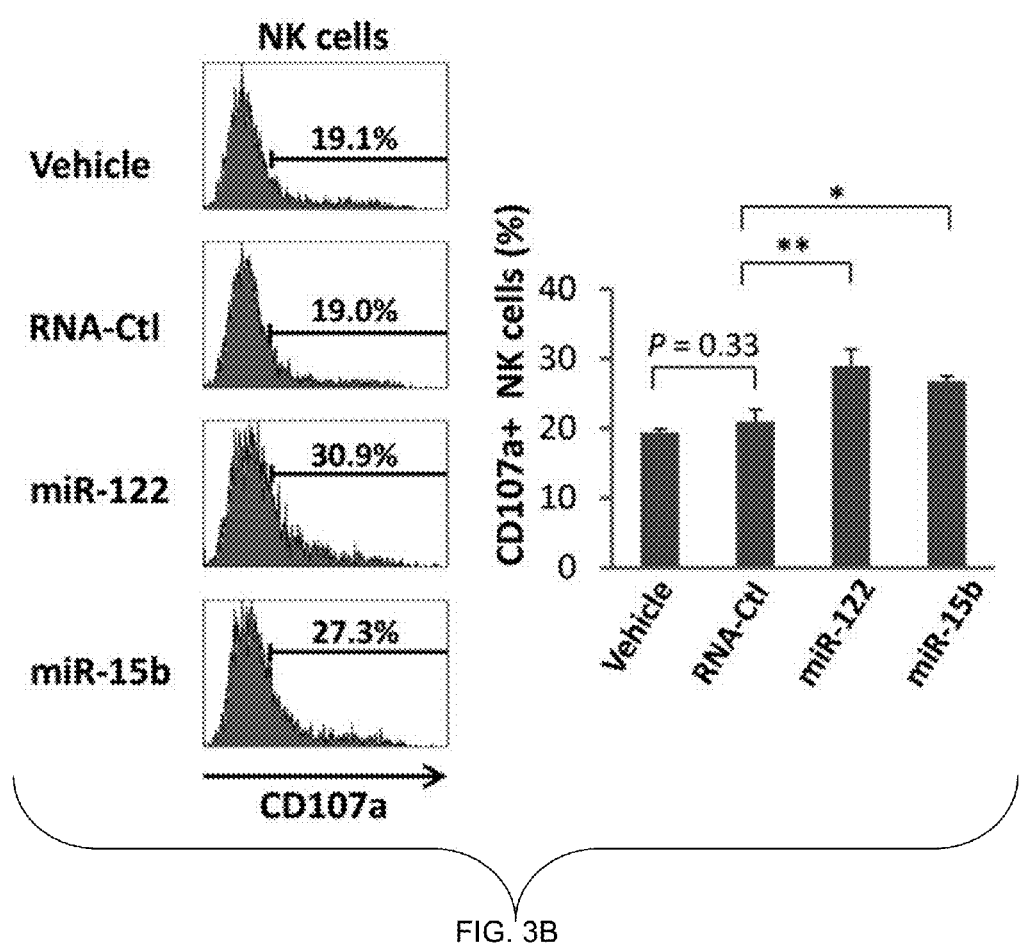

As seen from FIG. 3, miRNAs activate NK cells in vivo. Normal wild-type mice were treated with miR-122 and miR-15b by injecting 1 dose of miRNAs, without administration of exogenous IL-12. The mice were sacrificed 4 days later. Flow cytometric analysis indicates that NK cells from miRNA-treated mice have twofold to threefold higher surface expression of the activation marker CD69 in comparison with that from either vehicle- or RNA-Ctl sequence-treated mice (FIG. 3A). In vivo NK-cell activation by miRNAs was also evidenced by ex vivo coculture with YAC tumor cells in the absence of any exogenous IL-12, which resulted in a statistically significant increase in CD107a expression (FIG. 3B).

Figure 4A:
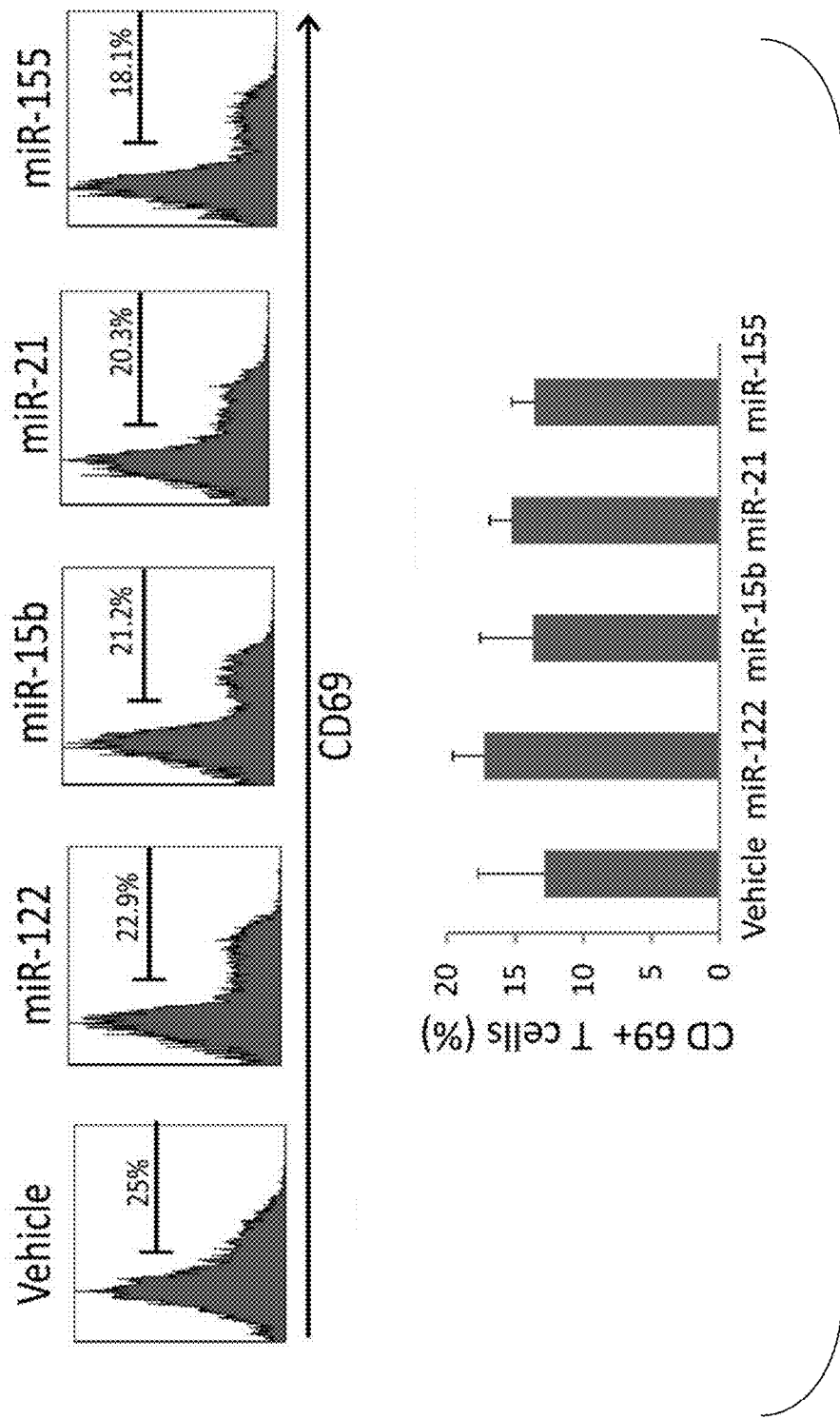
FIGS. 4A-4B: MiRNAs do not activate T cells in vivo.
Figure 4B:
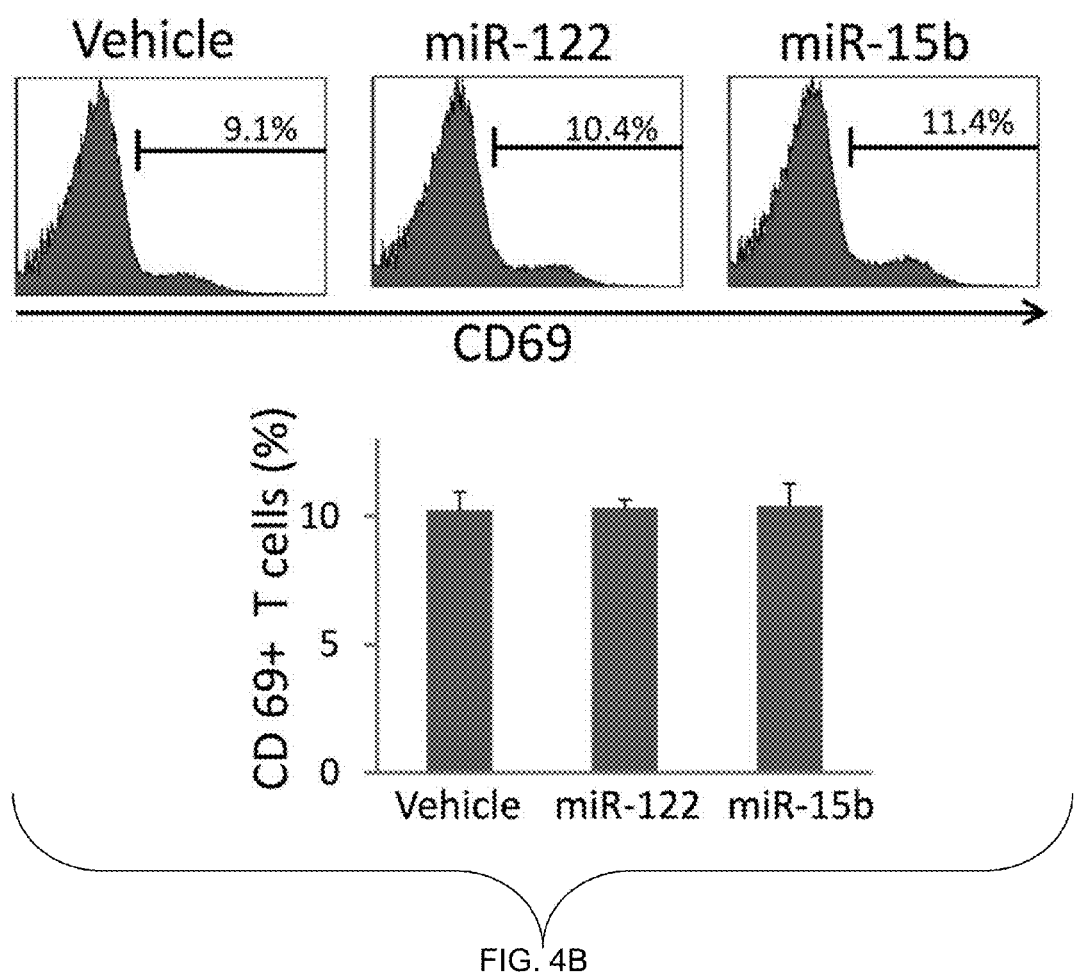

As seen in FIGS. 4A-B, miRNAs do not activate T cells in vivo or in vitro. In contrast to NK cells, human T cells were not activated by miRNAs when assessed in culture of whole PBMCs (FIG. 4A). Moreover, mouse T cells were not found to be activated following the in vivo infusion of miRNA (FIG. 4B). These data show that miRNAs selectively activate the innate immune response without activating adaptive (T-cell) immune response.

Figure 13:
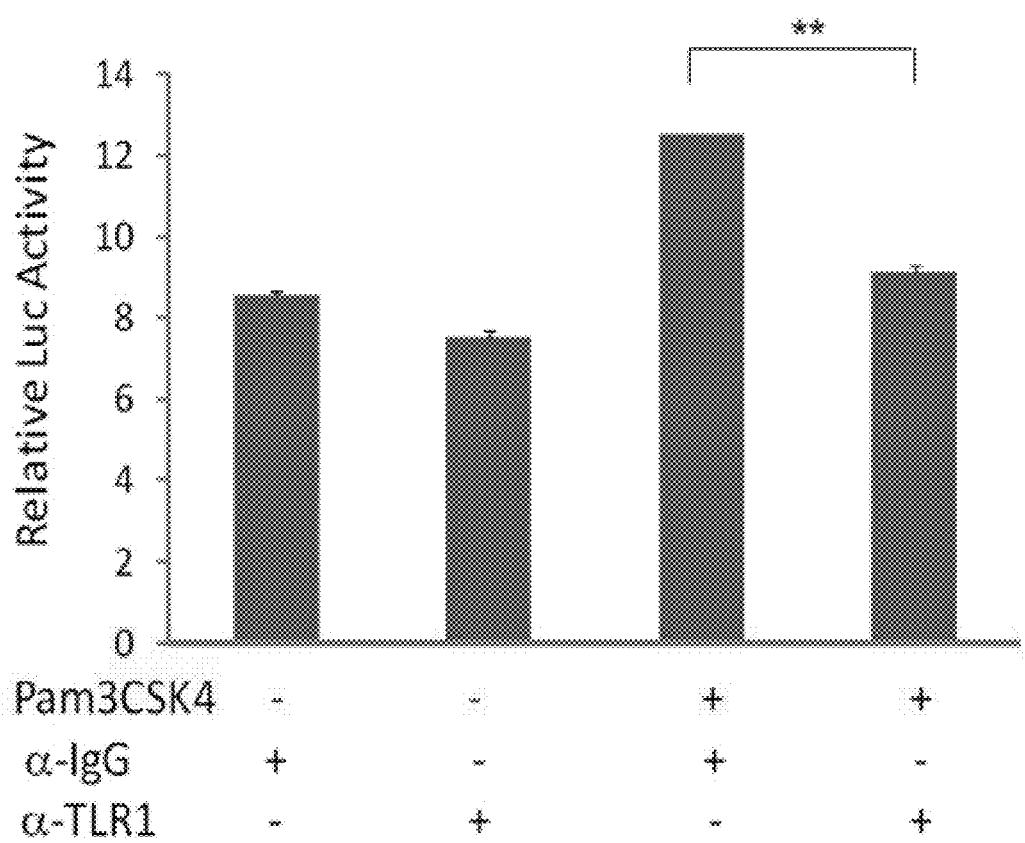
FIG. 13: Anti-TLR1 antibody effectively blocks the TLR1-NF-κB signaling activation by Pam3CSK4 ligand. 293T cells were transfected in 24-well plates for 24 hr with TLR1 and TLR2 expression plasmids (0.5 µg for each) along with pGL-3XIκB-luc (1 µg), containing three consensus IkB-binding sites, and pRL-TK renilla-luciferase control plasmid (5 ng, Promega). The cells were then incubated with either TLR1 blocking antibody or IgG control (10 µg/ml for each) for 2 h, followed by treatment with the TLR1 ligand Pam3CSK4 (2 ng/ml) for an additional 24 h. Firefly and renilla luciferase activities were measured using Dual-Luciferase® Reporter Assay System (Promega), and the relative activity was determined by the ratio of these two luciferase activities. ** indicates p<0.01 and error bars represent S.D.

As seen in FIG. 5, activation of NK cells occurs via the TLR signaling pathway. TLR9 has been shown to recognize and respond to bacterial and viral or synthetic deoxyoligonucleotides that contain unmethylated CpG dinucleotide motifs. Murine TLR7 and human TLR8 also recognize viral RNA. Therefore, whether miRNAs are activating NK cells through the TLR8 or TLR9 pathway was investigated. It was first determined that mRNA expression levels of TLR8 and TLR9, as well as other TLRs, in resting human NK cells as well as cells, costimulated with IL-12 and miRNAs. Surprisingly, TLR8 and TLR9 were found to be negligibly expressed in both resting and activated human NK cells, indicating that activation of NK cells by miRNAs is unlikely to occur through these receptors. In contrast, resting human NK cells were found to express relatively higher transcript levels of TLR1, TLR3, and TLR6 (FIG. 5A). Accordingly, TLR signaling was disrupted by blocking each of these 3 TLRs with their respective blocking Abs. For TLR1, an antibody with a capability to block signaling activated by its ligand, Pam3CSK4, was used (FIG. 13). Blockade of TLR1 in primary NK cells significantly reduced miRNA-mediated induction of IFN-γ production by ~50%, while blockade of TLR3 and TLR6 had no significant effect on NK-cell activation (FIG. 5B).

Figure 5A:
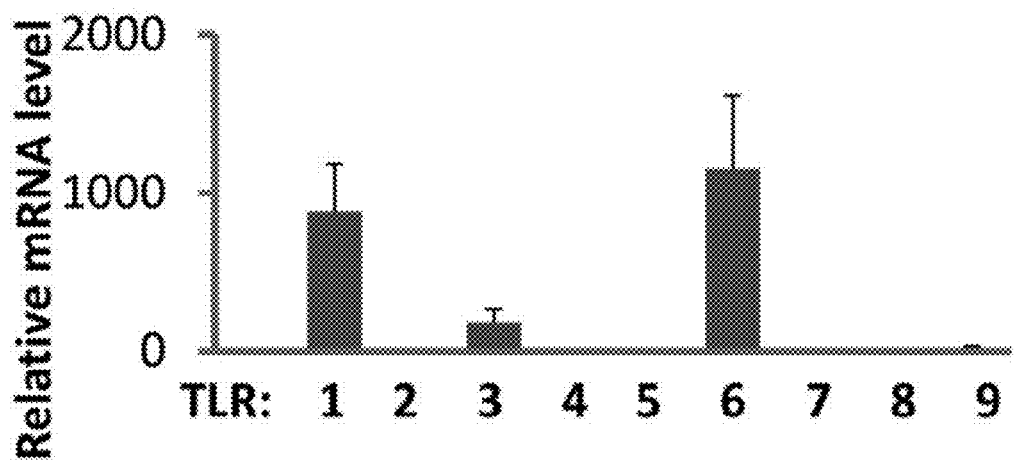
FIGS. 5A-5E: Interaction of TLRs and miRNAs.
Figure 5B:
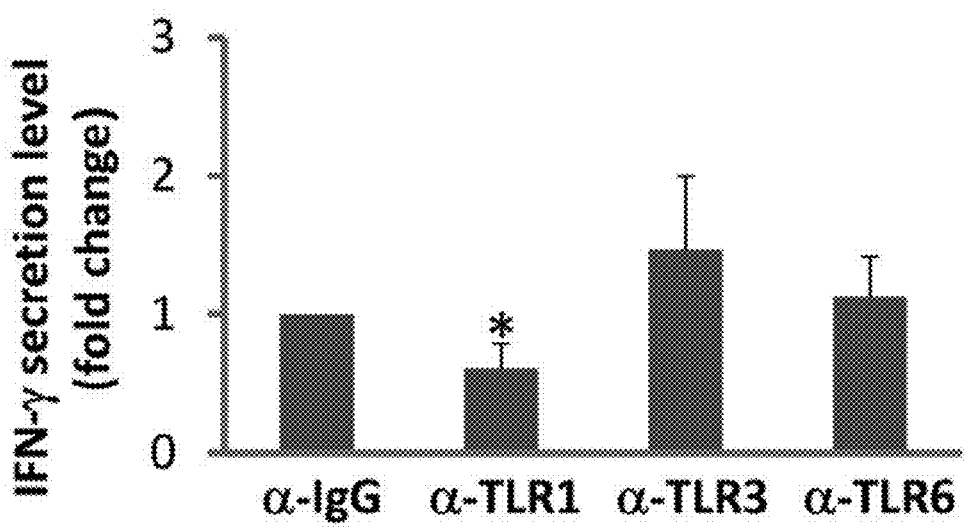
Figure 5C:
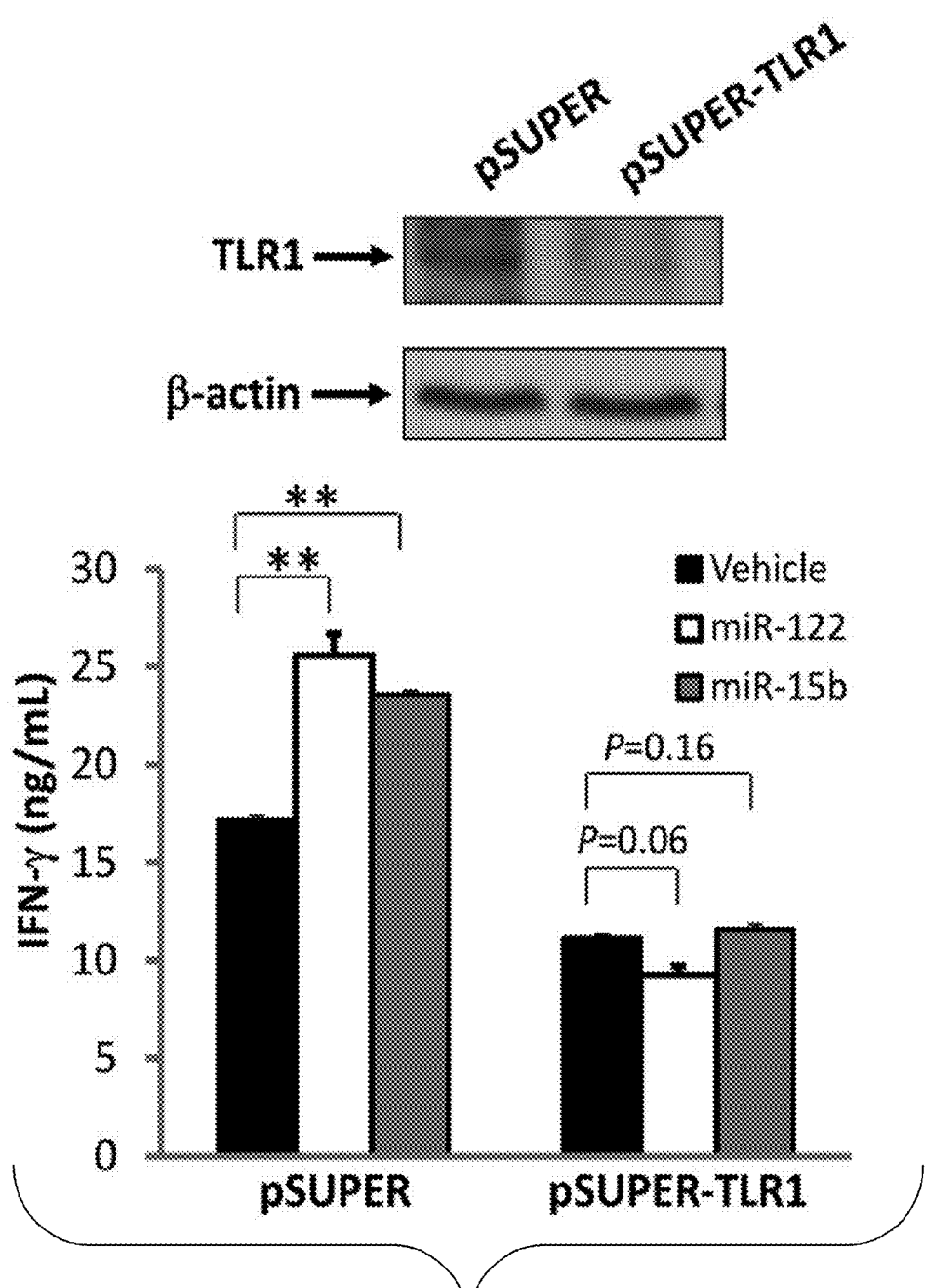
Figure 14:
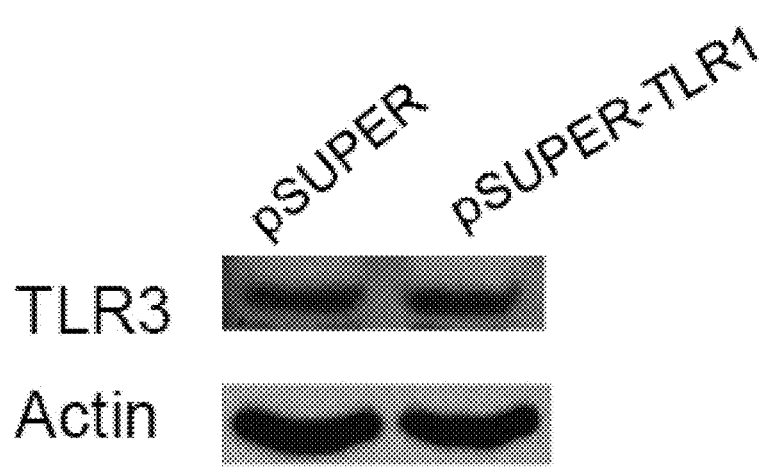
FIG. 14: TLR1 knockdown cells do not have a decreased TLR3 expression. NK-92 cells were infected with pSUPER-TLR1-GFP or the control retroviruses, and stably transduced cells were sorted based on GFP expression. Both vector-transduced cells (pSUPER) and TLR1 knockdown cells (pSUPER-TLR1) were lysed for Western blotting using a TLR3 antibody (Thermal Scientific Inc.). The same membrane was blotted with β-actin to demonstrate equivalent loading of the samples. Data show that TLR3 is not knocked down by TLR1 shRNA in a pSUPER vector.
Figure 15:
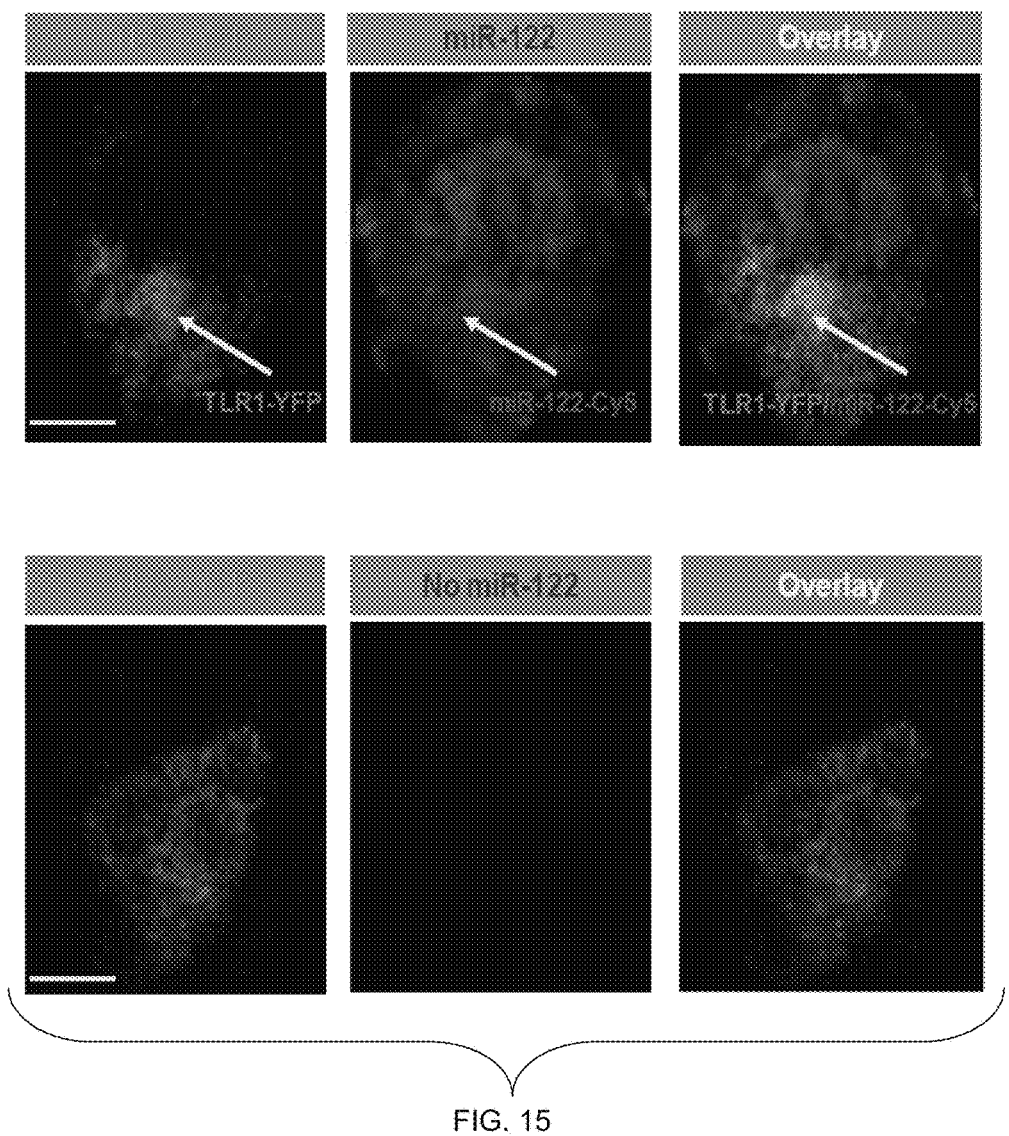
FIG. 15: Co-localization of TLR1 and miRNAs. HEK293T cells were grown on glass cover slips in 6-well plates and transfected with 4 µg TLR1-YFP plasmids (Addgene). 24 hours later, the transfected cells were stimulated with or without 10 µg/ml Cy5-labeled miR-122 in complexes of DOTAP for 12 h. The coverslips were then washed and mounted on the glass slides using the Prolong Gold Antifade Reagent (Invitrogen). Confocal images were acquired using a Zeiss 510 META laser-scanning confocal microscope. Scale bar (the horizontal and yellow line at the left, bottom corner): 5 µm.

To further demonstrate that TLR1 participates in miRNA-induced NK-cell activation, an shRNA approach was taken. First it was confirmed that TLR1, but not TLR3, was successfully knocked down in NK-92 cells (FIGS. 5C, 14). Then, it was found that TLR1 knockdown caused NK-92 cells to lose their capability for miRNA-mediated activation as no increase in IFN-γ production was observed, while the empty vector (pSUPER)-transduced control cells remained responsive to miRNAs (FIG. 5C). A confocal microscopy study of HEK293T cells cotransfected with miRNAs and TLR1-YFP fusion plasmid indicated that miRNAs and TLR1 protein colocalize with each other within these cells (FIG. 15). Collectively, these data demonstrate that NK-cell activation by miRNAs occurs, at least in part, via the TLR1 signaling pathway.

Figure 5D:
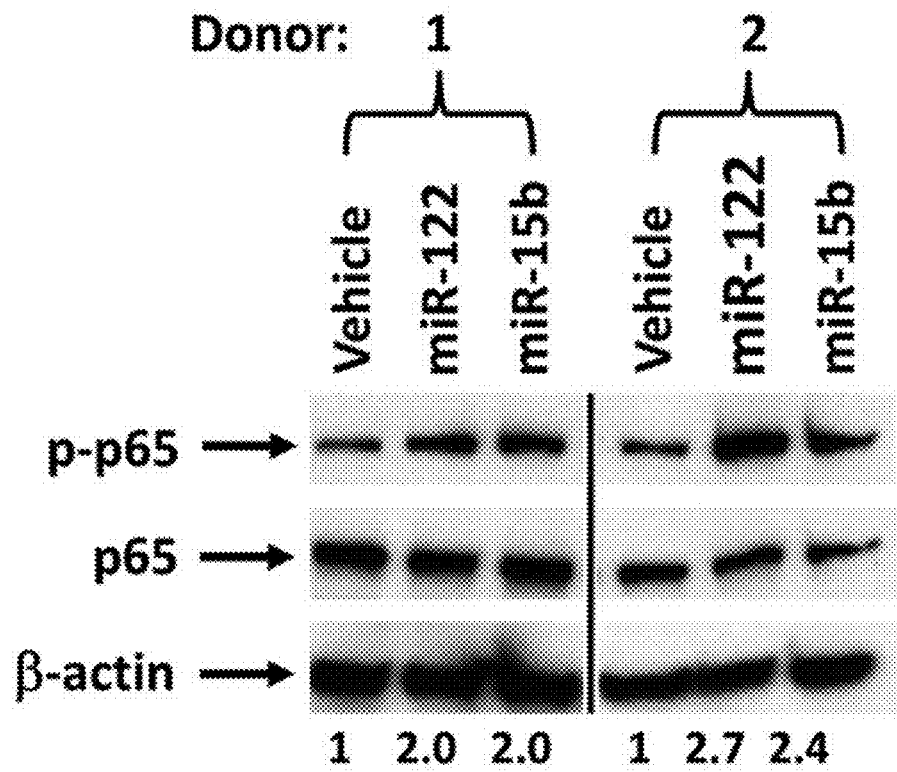
Figure 5E:
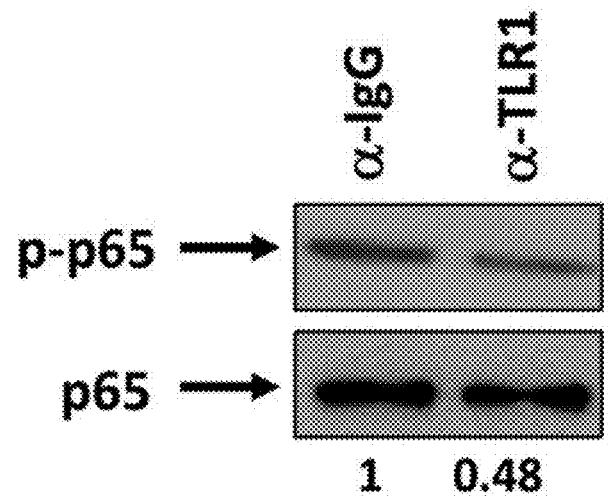
Figure 19:
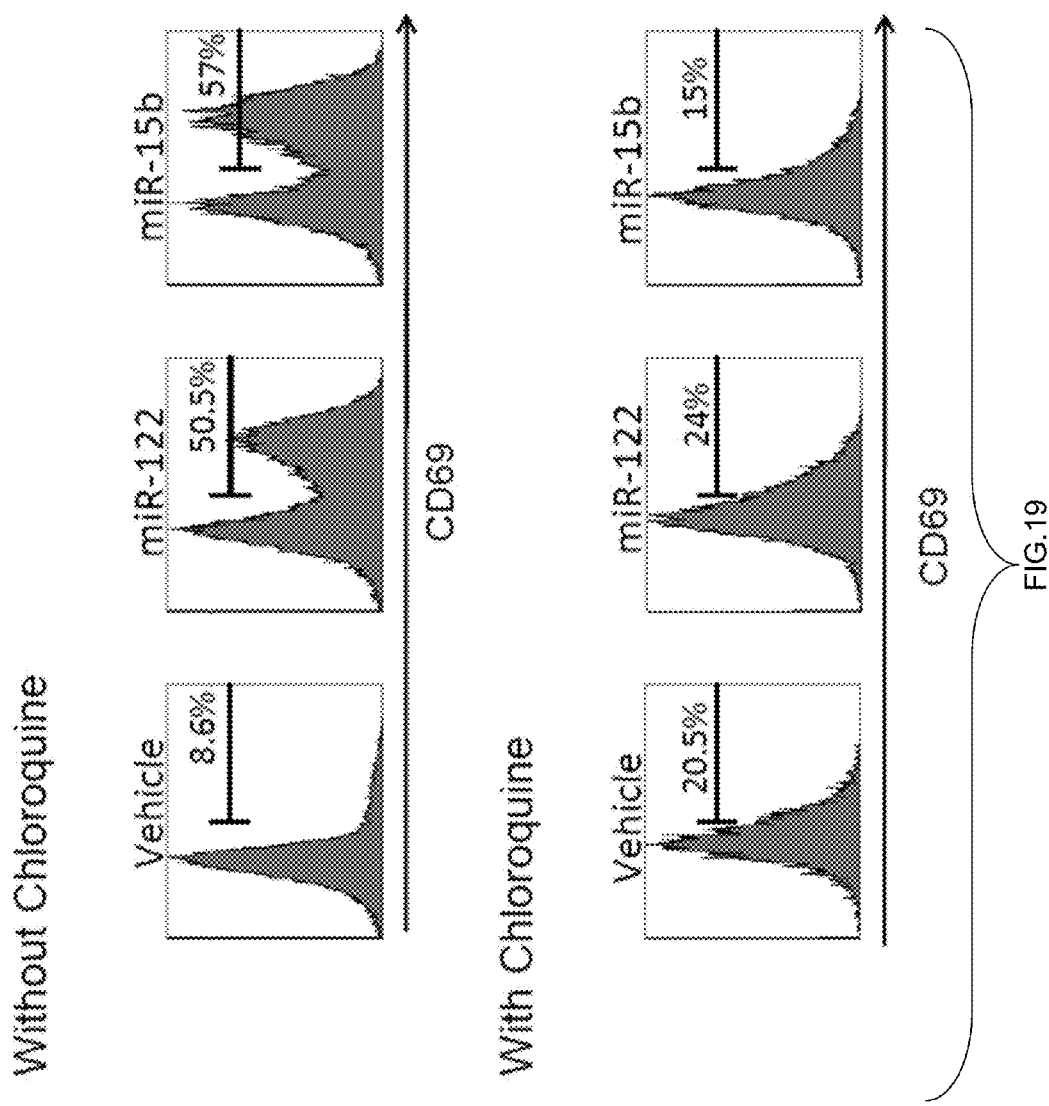
FIG. 19: The effects of chloroquine on NK cell activation by miRNAs. The introduction of chloroquine into the culture system blocked NK cell activation by miRNA, demonstrating that internalization of miRNAs interacting with TLR1 is likely necessary during miRNA-mediated NK cell activation.

Nuclear factor (NF)-κB represents a signaling pathway downstream of several TLRs, including TLR1. To further evaluate whether miRNAs activate NK cells via TLR signaling, NF-κB activation in NK cells after treatment with miRNAs was assessed. Although the total level of p65 protein, a transactivation component of NF-κB signaling, was unchanged, treatment with miRNAs induced an increase in the phosphorylation of p65 in primary NK cells primed with IL-12 (FIG. 5D). To further confirm that miRNA-induced activation of NK cells requires TLR1-mediated NF-κB signaling, TLR1 was blocked with its blocking antibody. The signaling blockade inhibited phosphorylation of p65 (FIG. 5E). Purified primary human NK cells were treated with miR-122 and miR-15b in the same way as done to determine p65 activation, but no phosphorylation of IRF3, an activation event specifically mediated via TLR3, was observed. The effects of chloroquine, an inhibitor of cellular internalization, were also evaluated. The introduction of chloroquine into the culture system blocked NK cell activation by miRNAs, indicating that internalization of miRNAs interacting with TLR1 is important during miRNA-mediated NK cell activation (FIG. 19).

Figure 6A:
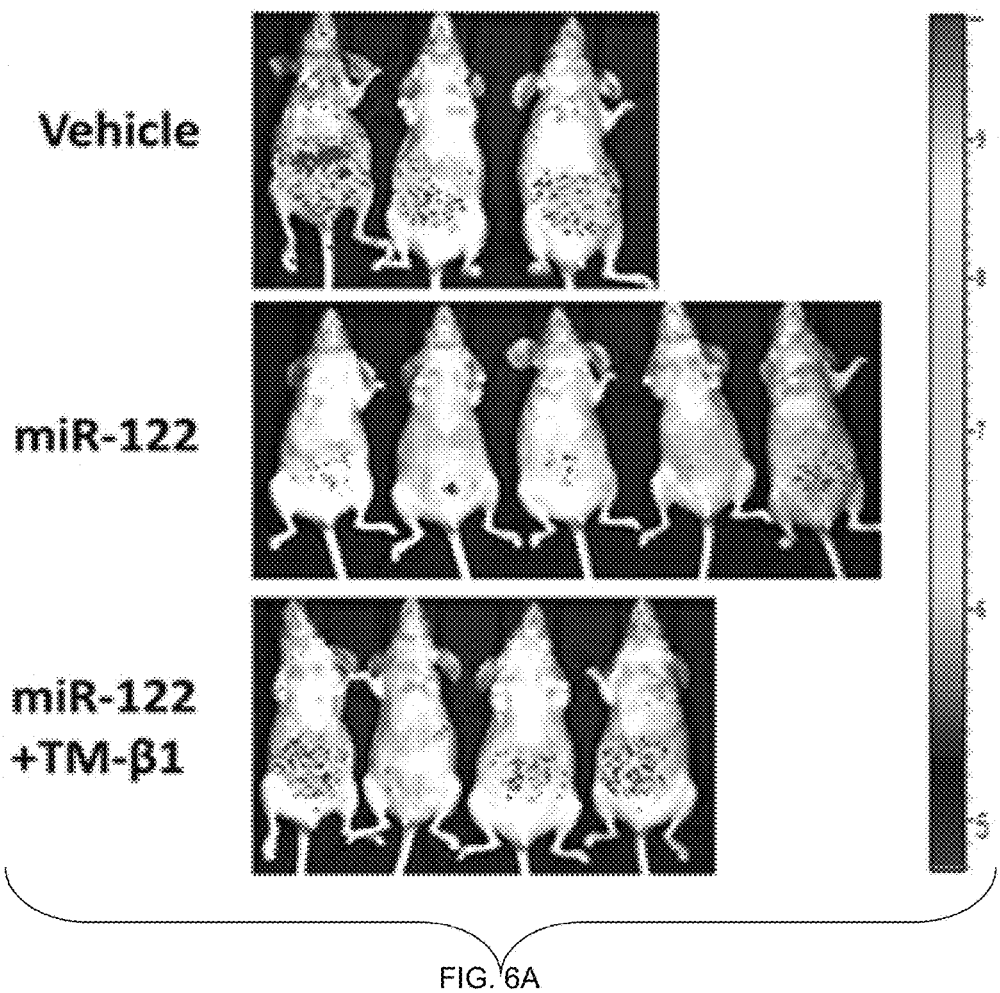
FIGS. 6A-6B: MiRNA stimulation enhances antitumor activity of NK cells in vivo.
Figure 6B:
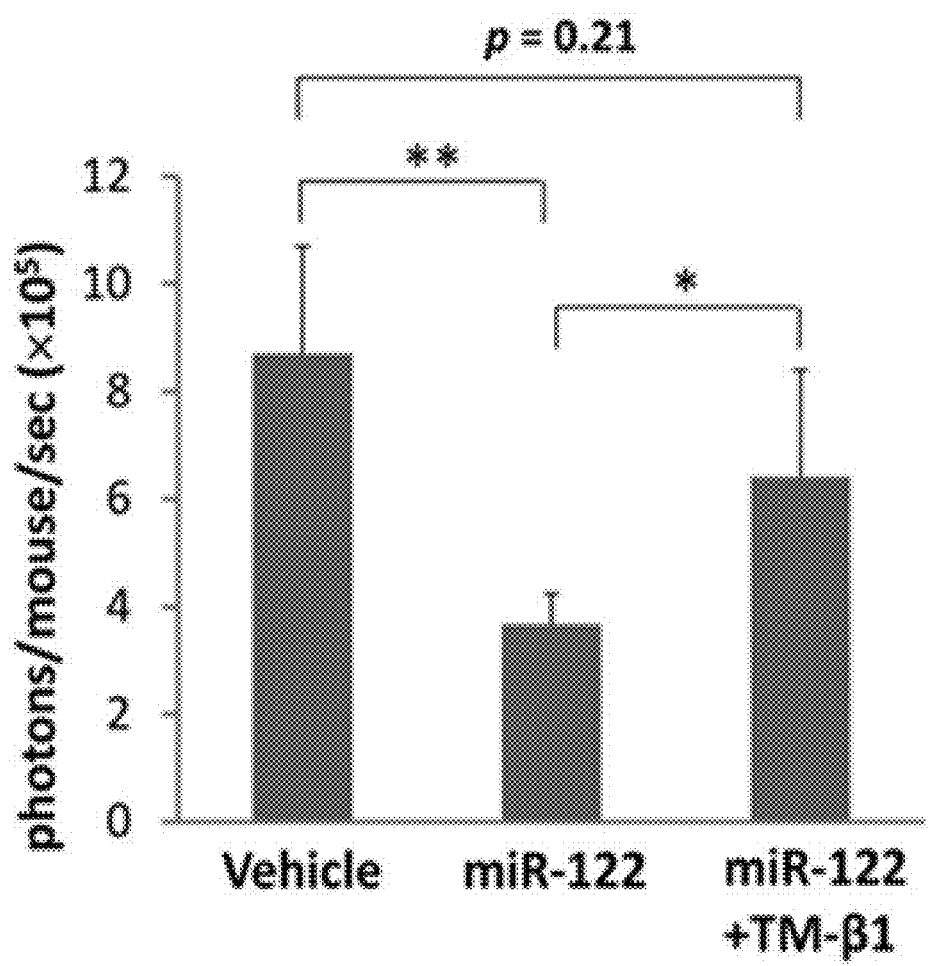
Figure 16:
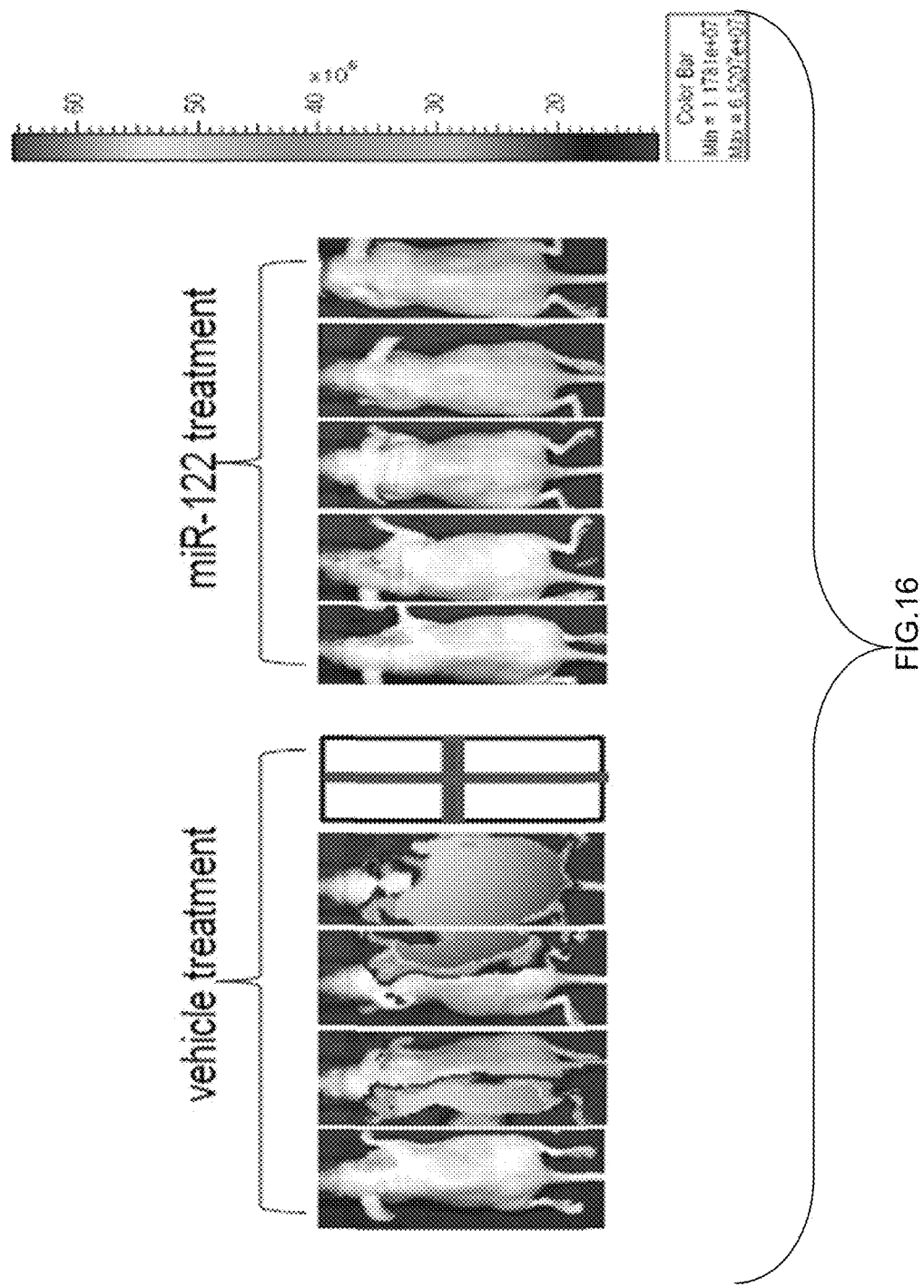
FIG. 16: MiRNA treatment significantly suppresses tumor growth in vivo. Ventral bioluminescence imaging of mice bearing A20 lymphoma. Athymic nude mice (5 mice per group) were injected with $1\times10^5$ luciferase-expressing A20 cells via tail veins and subjected to miRNA or vehicle cells stimulation three times per week for 4 consecutive weeks. One of the mice in the vehicle group died of tumor before its images were taken, and is represented as a red cross.

As seen from FIG. 6, miRNAs enhance antitumor activity of NK cells in vivo to control tumor development. A hallmark of NK-cell function is to kill tumor cells or virally infected cells. To further validate the physiological relevance of NK activation by miRNAs, mice were treated with miR-122 prior to and post implantation of A20 lymphoma cells in the presence or absence of NK-cell depletion. To exclude the possible T-cell effect, athymic nude mice were used. As shown in FIG. 6, after 3 doses of miR-122, the growth of A20 tumor cells in mice was significantly suppressed when compared with vehicle-administered mice. However, this effect was largely abrogated when the NK cells were depleted by TM-β1 mAb treatment, demonstrating that miRNA suppressed tumor growth, at least in part, through NK-cell activation. More robust inhibition of tumor growth was observed when the experiment was repeated with more frequent miRNA injections and a longer duration of treatment (3 times per week for 4 consecutive weeks instead of 3 injections during 18 days; FIG. 16).

Figure 7A:
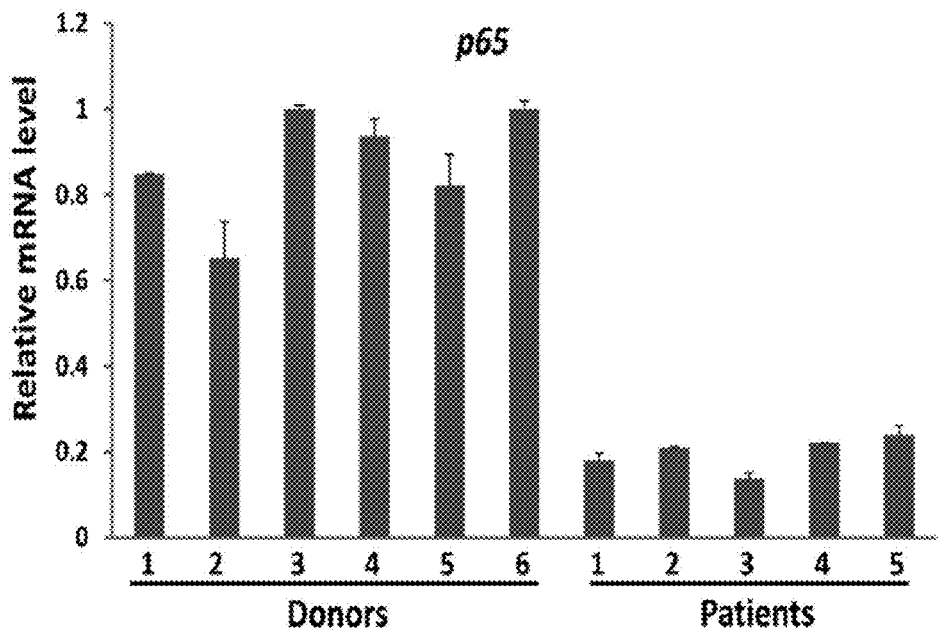
FIGS. 7A-7B: Downregulation of the NF-κB signaling pathway components in NK cells from lymphoma patients. NK cells were isolated from PBMCs of both healthy donors and lymphoma patients as described in Example I. The purified NK cells were then immediately subjected to RNA extraction and cDNA synthesis. The expression levels of p65 (FIG. 7A) and IRAK1 (FIG. 7B) were determined by SYBR Green real-time RT-PCR assay.
Figure 7B:
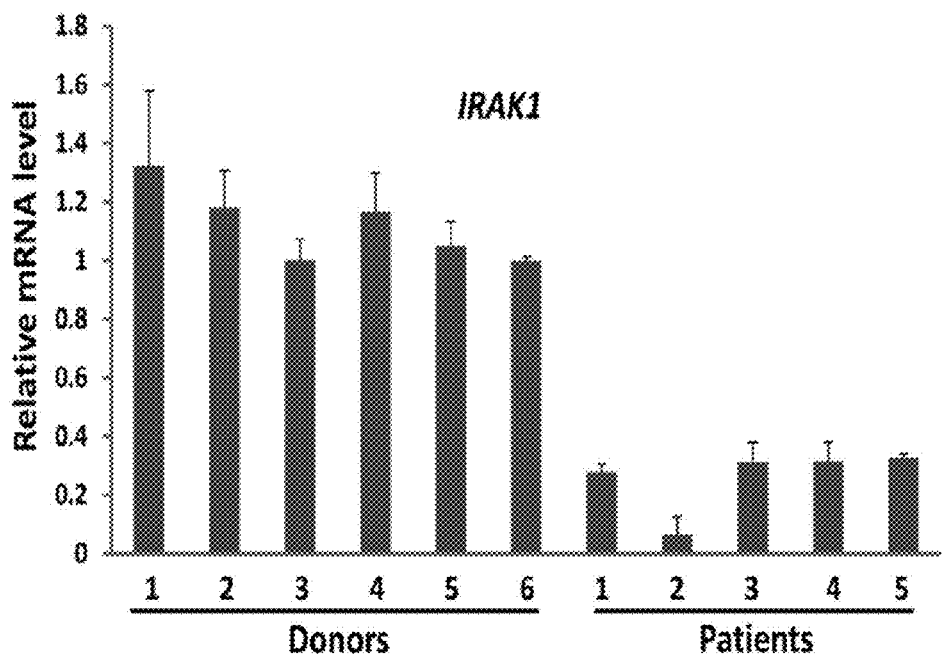
Figure 17:
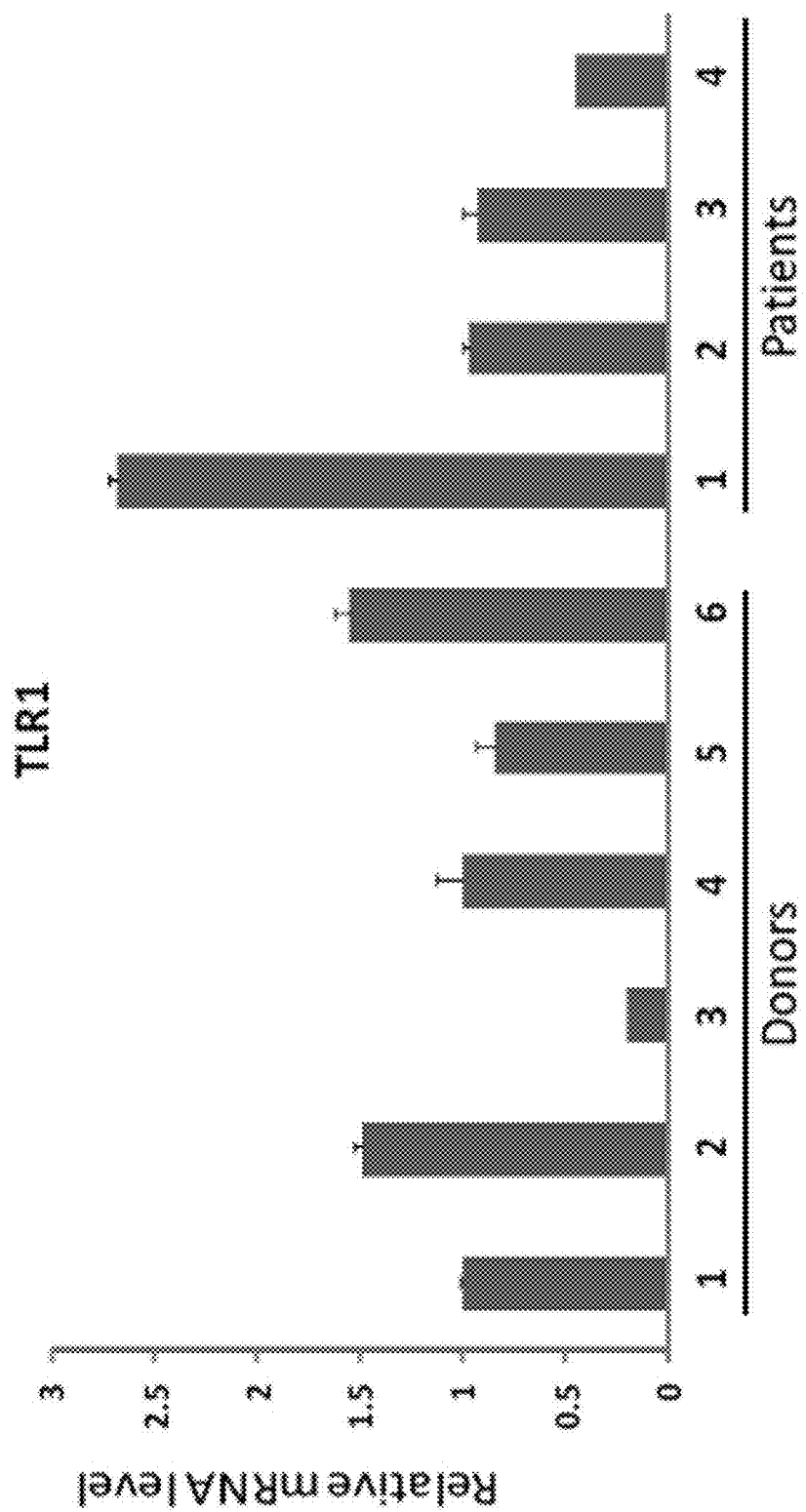
FIG. 17: Expression of TLR1 in lymphoma patient NK cells. NK cells were isolated from PBMCs of both healthy donors and lymphoma patients as described in Example I. The purified NK cells were then subjected to RNA extraction and cDNA synthesis. The expression level of TLR1 was determined by SYBR Green Real-time PCR assay.

As seen in FIGS. 7A-B, components of the TLR signaling pathway are downregulated in NK cells from cancer patients. The data presented provide strong evidence that miRNAs have a role in combating tumors by directly activating NK cells. Yet, some cancer patients with disease progression have high levels of circulating miRNAs, which indicates that there may be a mechanism(s) by which tumors escape surveillance by miRNA-activated NK cells. To investigate this, NK cells were purified from PBMCs of lymphoma patients. These patients were reported to have elevated expression of miRNAs such as miR-155. Although there was no significant difference of TLR1 expression between healthy donors and cancer patients (FIG. 17), p65 and IRAK1, the 2 main components in the TLR1NF-κB signaling pathway, were consistently and significantly downregulated in NK cells from lymphoma patients (FIGS. 7A-B). Thus, higher miRNAs in cancer patients may therefore be unable to activate NK cells in order to control tumor progression.

Example II

MiR-155

Material and Methods
Mice

Generation of the lck-miR-155 C57BL/6 (B6) tg mouse model was conducted. Littermates between 8.5 and 14 weeks of age were used for all experiments. B6 CD45.1$^+$ mice were obtained from Jackson Laboratories. Generation of the IL-15 B6 transgenic mice was then conducted. Double transgenic mice for miR-155 and IL-15 were generated by crossing single miR-155 and IL-15 B6 tg mice. Rag2/Il2rg double knockout (Rag2$^{-/-}$xIl2rg$^{-/-}$) mice were purchased from Taconic.

Mice were bred and maintained in an animal care facility at The Ohio State University (OSU). All animal work was approved by the Ohio State University Animal Care and Use Committee, and mice were treated within the institutional guidelines for animal care.

NK Cell Preparations and Cytokines

All experiments were performed with highly purified NK cells. To achieve this, mouse NK cells were first isolated from spleens using an NK cell isolation kit and/or microbeads from Miltenyi Biotech Inc. Enriched preparations contained at least 70% to 80% NK cells which were then sorted for NK1.1$^+$CD3 cells using FACSAria II cytometer (BD Bioscience). Purity at the time of all experiments was >99.5%. Purified mouse NK cells were either used fresh or cultured in RPMI-1640 medium containing 450 or 900 human IU/ml of IL-2 (Hoffman-LaRoche Inc.), and 55 μM β-mercapethanol (Gibco), or in 100 ng/ml of human IL-15 (Amgen) and 55 μM β mercaptoethanol, or with 20 ng/ml mouse IL-12 (Genetics Institute Inc.) and 10 ng/ml mouse IL-18 (R&D Systems).

Cell Lines

The YAC-1 mouse lymphoma cell line, RMA T-cell lymphoma tumor cells and Rae1β-transduced RMA tumor cells were maintained in RPMI-1640 medium (Invitrogen), and the murine mastocytoma P815 cells were maintained in DMEM medium, both supplemented with 10% heat-inactivated FBS (Invitrogen) and 2 mM L-glutamine (Gibco).

Flow Cytometry Analysis

Single-cell suspensions of spleens were prepared and red blood cells were removed using ammonium chloride (Stem Cell Technology Inc.). Anti-CD 16/32 (2.4G2) Ab (BD Biosciences) was used to block Fc receptors (1 μg/million cells). Splenocytes were stained with the Abs (clones in parenthesis) reactive against the following antigens: NK1.1 (PK136), CD3ε (145-2C11), CD117 (ACK45), CD27 (LG.3A10), CD11b (M1/70), CD49b (DX5), CD122 (TM-beta1), Ly-49C/I (5E6), Ly-49I (YLI-90), Ly-49A (A1), CD16/32 (2.4G2), Ly-49D (4E5), Ly-49G2 (4D11). These and isotype control Abs were purchased from BD Biosciences. Rat Abs to mouse CD94 (18d3), CD69 (H1.2F3), NKG2D (CX5), NKG2ACE (20d5), 2B4 (eBio244F4), NKp46 (29A1.4), and Ly-49C/I/F/H (14B11) were purchased from eBioscience. NK cells were gated on NK1.1$^+$CD3$^-$ for FACS analysis of these antigens. Samples were acquired using FACSCalibur or LSRII (BD Biosciences), and analyzed with FlowJo v7.6.1 (TreeStar).

Survival Assay

For the NK cell survival assay, $2\times10^6$ freshly isolated splenocytes were cultured in 24 well plates in 2 mL of RPMI medium containing 10% FBS and 55 μM β-mercaptoethanol (Gibco) for 24 hours. After staining with Abs for NK1.1 and CD3, cells were labeled with Annexin-V and 7-AAD (BD Bioscience) following the manufacturer's protocol. Samples were analyzed by FACS within one hour of staining.

In Vivo BrdU Incorporation Assay

BrdU was administered at a concentration of 0.8 mg/mL in drinking water containing 1% glucose. Water containing BrdU was prepared daily. In order to label simultaneously, all mice were injected intraperitoneally once with 1.5 mg of BrdU in PBS on day 1. As a negative control, one mouse was administered drinking water without BrdU. Ten days later, mice were sacrificed and splenocytes were stained for FITC-CD3, PE-NK1.1, 7-AAD, and APC-BrdU following the manufacturer's protocol (BD Biosciences). For staining control, one mouse was injected intraperitoneally with 1.5 mg of BrdU 12 hours before sacrifice and bone marrow was stained with the same antibodies.

Assessment of In Vivo NK Cell Expansion

NK1.1$^+$CD3$^-$ NK cells were cultured ($2\times10^4$) in triplicate wells of 96 well plates in 200 μl of RPMI medium containing 10% FBS and human IL-15 (100 ng/ml) and 55 μM β-mercaptoethanol. Viable cells were enumerated 2-7 days after plating using the tripan blue (Invitrogen) exclusion assay and a standard hemacytometer.

Transfer Experiment

CD11b$^{low}$CD27$^{high}$ splenic NK cell subset from CD45.2$^+$ and miR-155 tg mice were FACS sorted to >98% purity and injected intravenously into sublethally irradiated or non-irradiated CD45.1$^+$ wt littermate recipient mice. Transferred splenic NK cells were analyzed by flow cytometry of NK cell-enriched splenocytes after 16 days. Expression of CD27 and CD11b was analyzed after gating on NK1.1$^+$CD3$^-$CD45.2$^+$ cells.

Cell Stimulation

Ex vivo purified NK cells from wt and miR-155 tg mice were stimulated with human IL-2 (90 ng/mL), human IL-15 (100 ng/mL), or the combination of IL-12 (20 ng/mL) plus IL-18 (10 ng/mL), for the indicated times. For stimulation with YAC-1 tumor cells, NK cells were expanded in IL-2 for at least 8 days. YAC-1 cells were placed on ice for two hours, fixed with paraformaldehyde ($2\times10^6$/mL, 1% paraformaldehyde in PBS, 15 min on ice) and washed before using. NK cells were starved from IL-2 for 2 hours on ice. NK cells and fixed YAC-1 targets were mixed at 5:1 ratio and stimulated for the indicated times.

NK Cell IFN-γ Production

Wt and miR-155 tg NK1.1$^+$CD3$^-$ NK cells or CD11b$^{low}$CD27$^{high}$, CD11b$^{high}$CD27$^{high}$ and CD11b$^{high}$CD27$^{low}$ wt and miR-155 tg NK subsets were left untreated or stimulated with the combination of IL-12 (20 ng/mL) plus IL-18 (10 ng/mL) for 18 h at 37° C. Cell supernatants were collected and analyzed by ELISA for IFN-γ (R&D Systems). Results are shown in FIGS. 23D-E, as the means of triplicate wells±SEM.

Cytotoxicity Assays

Cytotoxicity against tumor target cells was performed by standard 4-hour $^{51}$Cr release assay. YAC-1, RMA, RMA-Rae-1β cells, or P815 cells coated with an anti-mouse lymphocytes rabbit Ab (Accurate Chemical and Scientific Corporation) were used as targets. Ex vivo purified NK cells or NK cells cultured in IL-2 90 ng/mL for 8 days were used as effectors. A constant number of target cells ($3\times10^3$ to $1\times10^4$/well) and serial dilution of wt and miR-155 tg effector NK cells were used in triplicate. Spontaneous release was always <10%.

Conjugate Formation

Immune complex formation among purified wt and miR-155 tg NK cells and YAC-1 tumor cells were examined by flow cytometry. YAC-1 tumor cells were infected using the GFP encoding lentivirus vector pCDH (System Biosciences), and selected for GFP expression by FACS sorting. NK1.1$^+$CD3$^-$ NK cells were labeled with PE-conjugate anti-NK1.1 Ab. For the conjugate assay, $2\times10^5$ PE-labeled NK cells were mixed with 2×105 GFP YAC-1 cells in 200 μL of cold medium and centrifuged at 600 rpm for 1 min. To induce the formation of immune-complexes, cells were incubated at 37° C. for 0 min and 10 min. Reactions were stopped by adding ice cold PBS. 1.1$^+$GFP$^+$ conjugates were detected by FACS analysis.

Immunoblot Analysis

Purified NK cells were harvested, washed once with ice-cold PBS and lysed ($10^8$ cells/ml RIPA buffer: 0.15 M NaCl, 1% NP-40, 0.1% SDS, 50 mM Tris, [pH 8.0], supplemented with protease and phosphatase inhibitors, 1 mM phenylmethyl-sulfonylfluoride (PMSF), 1 mM Na$_3$VO$_4$, 50 mM NaF, 10 mM β-glycerol-phosphate, 1 mM EDTA, and a protease inhibitor cocktail tablet from Roche Applied Science). Alternatively, cells were directly lysed in Laemmli buffer ($2\times10^5$ cells/20 μL). Immunoblots were performed and Ab-reactive proteins were detected with horseradish peroxidase-labeled sheep anti-rabbit, mouse and/or goat IgG and enhanced chemiluminescence (ECL; Amersham Corp.). Proteins were analyzed in 4-15% SDS-PAGE (BIO-RAD Laboratories). Abs used were: the anti-SHIP1, anti-Actin, and anti-Granzyme M Abs from Santa Cruz Biotechnology; anti-Granzyme B, anti-Perforin, anti-phospho-AKT$^{Ser473}$, and anti-phospho-ERK$^{Thr202/Tyr204}$ Abs were purchased from Cell Signaling Technology Inc.; anti-GRB2 Ab was purchased from Transduction Laboratories.

Real Time RT-PCR

Total RNA was extracted using Trizol (Invitrogen). Reverse transcription was performed with Taqman MicroRNA Reverse Transcription Kit and RT primers specific for miR-155 and U6 or 292 as control (Applied Biosystems). Real-time RT-PCR reactions were performed in triplicate as a reaction with a primer/probe set specific for miR-155, and U6 or 292 as controls. Water (no template) was used as a negative control. Reactions were performed using an ABI prism 7700 sequence detector (Applied Biosystems). Data were analyzed according to the comparative CT method using the internal control U6 or 292 RNA levels to normalize differences in sample loading and preparation. Results represent the n-fold difference of transcript levels in a particular sample compared to samples of wt NK cells. Results are expressed as the mean±SEM of triplicate reaction wells.

Tumor Growth Assay

To determine the direct effect of wt and miR-155 tg NK cells on the growth of RMA-Rae-1β tumor cells in vivo, $2 \times 10^5$ wt or miR-155 tg NK cells were mixed with $1 \times 10^5$ tumor cells and injected subcutaneously into the shaved flank of Rag2$^{-/-}$xIl2rg/– recipient mice. As a negative control, $1 \times 10^5$ RMA-Rae-1β tumor cells were injected as above but in the absence of any mixing with NK cells. Tumors were then measured every two days using a caliper, and tumor volume was calculated as follow: tumor volume=0.5×(length)×(width). Animals were considered tumor free when no tumor was found 40 days after inoculation. Mice were sacrificed when tumor burden became excessive.

Statistics

Data were compared using Student's 2-tailed t-test. A p value less than 0.05 was considered significant. Survival data were analyzed using Kaplan-Meier and long-rank test methods (GraphPad Prism Version 5.0).

MiR-155 Causes Expansion, Arrest in Terminal Differentiation and Functional Activation of Natural Killer Cells As detailed in Example II below, NK cells in mice were genetically modified to overexpress miR-155 driven off the lck promoter. The results show that miR-155 is important for NK cell development, homeostasis, and the regulation of several intrinsic NK cellular functions.

Effect of miR-155 Overexpression on NK Cell Number

Figure 20A:
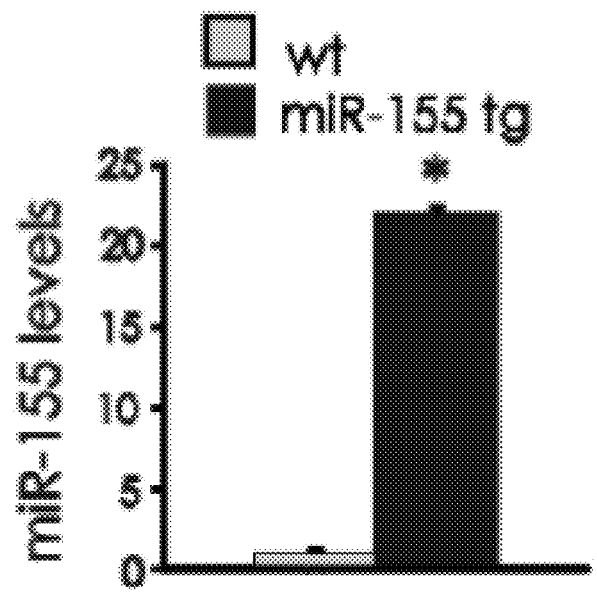
FIGS. 20A-20C: NK cell expansion in miR-155 tg mice.
Figure 20B:
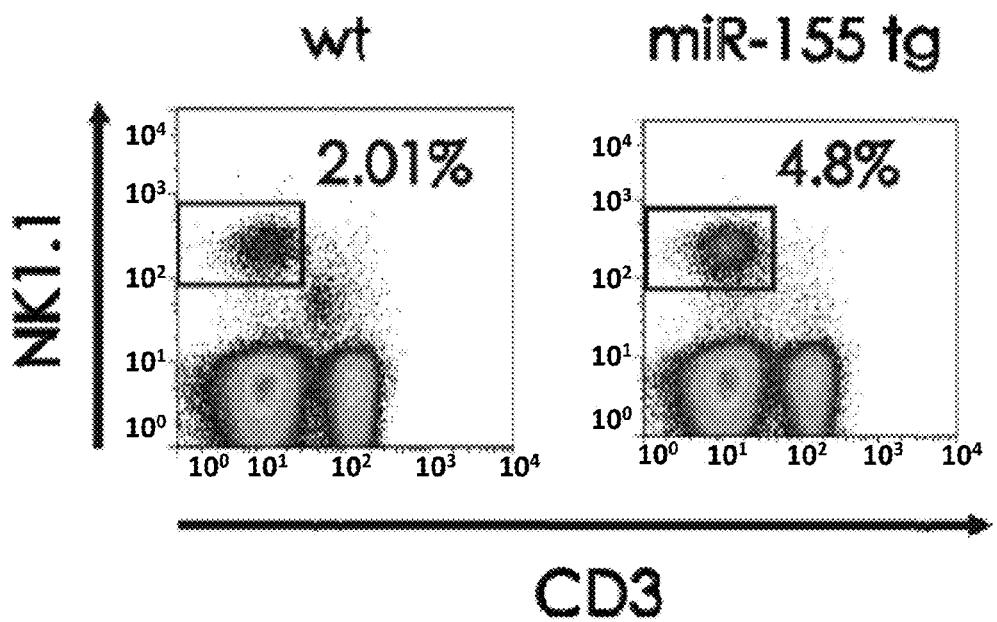
Figure 20C:
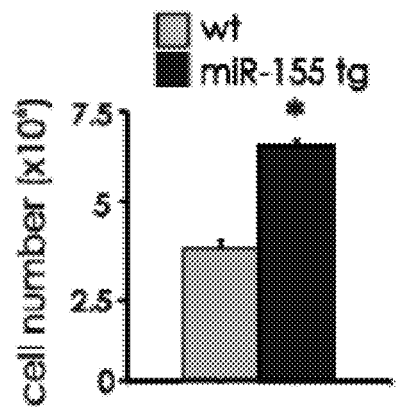

To determine the effects of miR-155 overexpression in NK cells, lck-miR-155 transgenic (tg) C57BL/6 (B6) mice previously generated were used. Real-time RT-PCR was used on RNA obtained from NK1.1$^+$CD3$^-$ FACS sorted wt and miR-155 tg NK cells to quantify miR-155 expression which was significantly higher in NK cells from miR-155 tg versus wt NK cells (average induction of 26.6+/−5.3 fold; FIG. 20A; p<0.0001, n=6). Similarly, miR-155 RNA was overexpressed in NK1.1$^-$CD3$^+$ T cells from miR-155 tg mice when compared to wt mice (Ranganathan et al., 2012). MiR-155 tg mice also had a statistically higher percentage of NK1.1$^+$CD3$^-$ NK cells compared to wt mice (FIG. 20B, p<0.0001; n=16), as well as a higher absolute number of NK cells (FIG. 20C; p<0.0001; n=13). On the other hand, a clear reduction in the percent of NK1.1$^+$CD3$^-$ NKT (p<00001; n=12) in the spleen of miR-155 tg mice when compared to wt mice (FIG. 20B) was observed.

Survival and Proliferative Capacities of miR-155 tg versus wt NK Cells

Figure 21A:
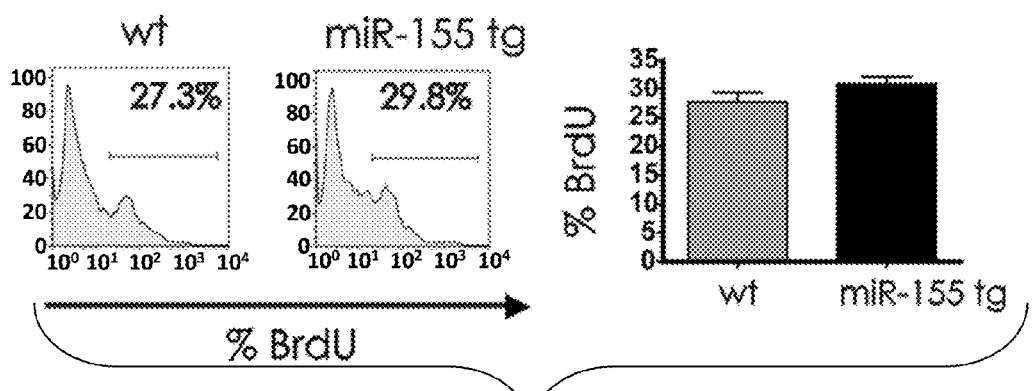
FIGS. 21A-21D: Proliferation and survival of miR-155 tg vs wt NK cells.

The evaluate the higher percentage and absolute number of NK cells in miR-155 tg mice compared to wt mice, the NK cell proliferative and survival capacities were determined For in vivo proliferation studies, mice received BrdU-containing drinking water for 10 days, and then splenic NK cells were analyzed for BrdU incorporation by flow cytometry. These results were unable to demonstrate a significant difference in the rate of BrdU incorporation between miR-155 tg NK1.1$^+$CD3$^-$ NK cells and wt NK cells (FIG. 21A; p=0.17; n=10).

Figure 21B:
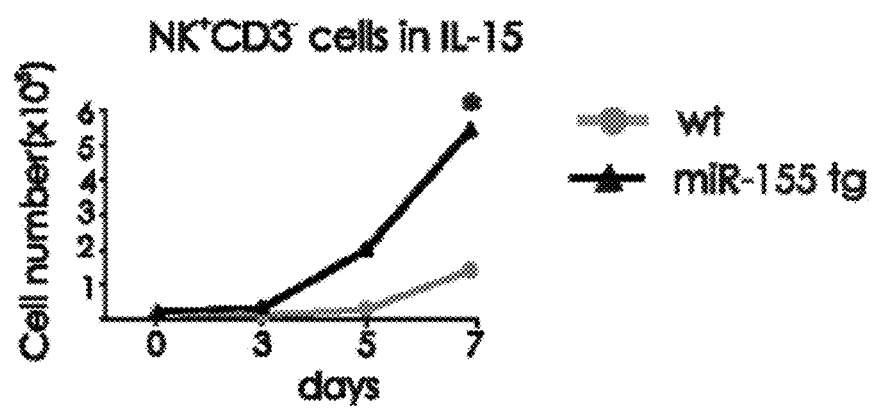

To determine if these miR-155 tg NK cells had the capacity for enhanced proliferation, parallel tests were conducted with FACS sorted NK1.1$^+$CD3$^-$ NK cells cultured ex vivo in the presence of interleukin-15 (IL-15), the endogenous survival and growth factor for NK cells. In vitro, miR-155 tg NK cells showed significantly greater expansion of their cell numbers when compared to wt cells in the presence of IL-15 (FIG. 21B, p<0.001, n=6).

Figure 21C:
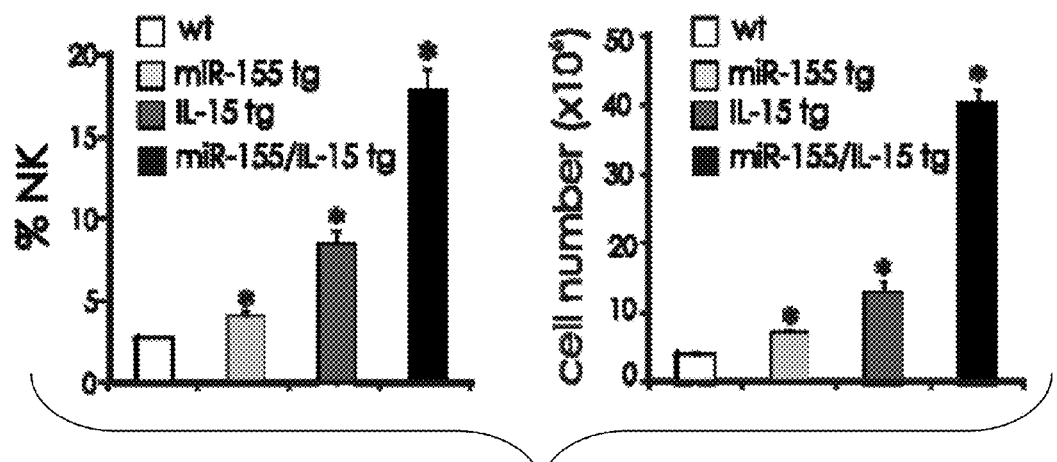

To determine if endogenous IL-15 cooperates with miR-155 in regulating NK cell number in vivo, miR-155 tg B6 mice were crossed with IL-15 tg B6 mice. In support of the in vitro data, it was observed that miR-155/IL-15 double tg mice had a significantly higher percentage of NK1.1$^+$CD3$^-$ splenic NK cells (FIG. 21C left; p<0.01, n=4), as well as a higher absolute number of splenic NK cells (FIG. 21C right; p<0.01; n=4) compared to either miR-155 tg or IL-15 tg mice alone.

For survival studies, splenic NK cells were harvested and cultured in vitro for 24 hours in medium without cytokines. At that time, NK cells were stained with Annexin V and 7-amino-actinomycin D (7-AAD) to assess for evidence of cell death.

Figure 21D:
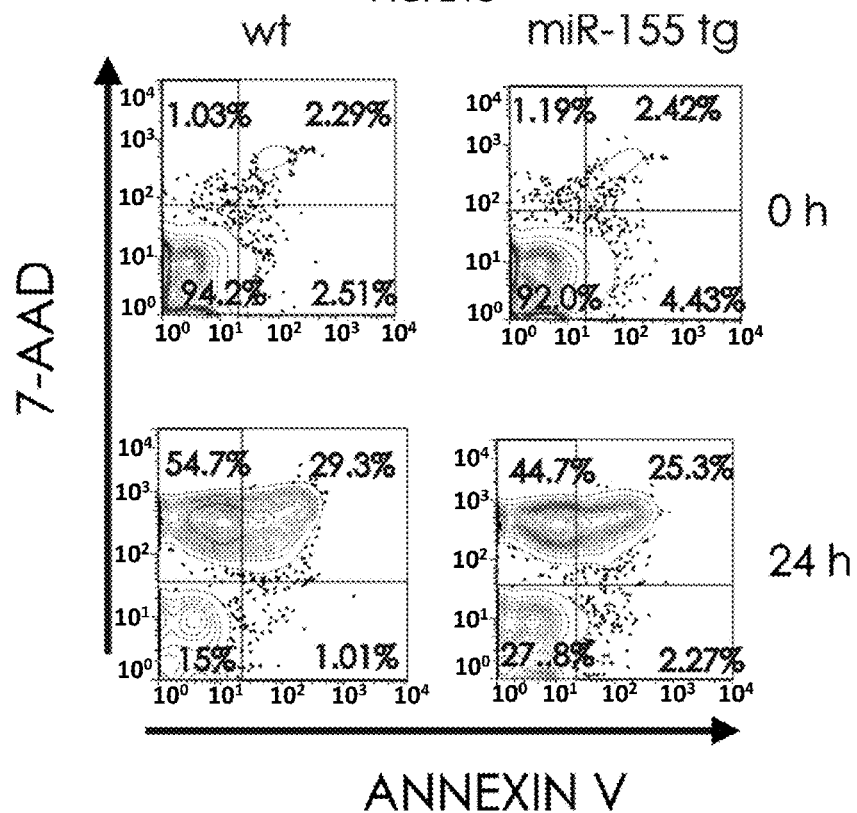

As shown in FIG. 21D, which is representative of five experiments, miR-155 tg NK cells showed a significantly greater fraction of viable cells as noted by: 1) a higher percentage of cells lacking an increase in Annexin V and 7-AAD when compared to wt NK cells (p<0.001), and 2) a greater fraction of Annexin V+ NK cells still lacking 7-AAD when compared to wt NK cells, consistent with early apoptosis (p<0.001). In contrast, wt NK cells had a greater fraction of 7-AAD+ and Annexin V-cells, consistent with necrosis at 24 hours when compared to miR-155 tg NK cells (p<0.001). No significant differences were observed between wt and miR-155 tg NK cells expressing both Annexin V and 7-AAD, indicative of cells in the late stage of apoptosis (p=0.18).

Collectively, these data show that NK cells from miR-155 tg mice have an enhanced intrinsic ability for survival in the absence of cytokines, and this contributes to their in vivo increase in absolute cell number when compared to wt NK cells. In addition, their growth can be further enhanced over that seen with wt NK cells in the presence of abundant exogenous or endogenous IL-15.

NK Cell Surface Antigen Expression in miR-155 tg Mice

Figure 22A:
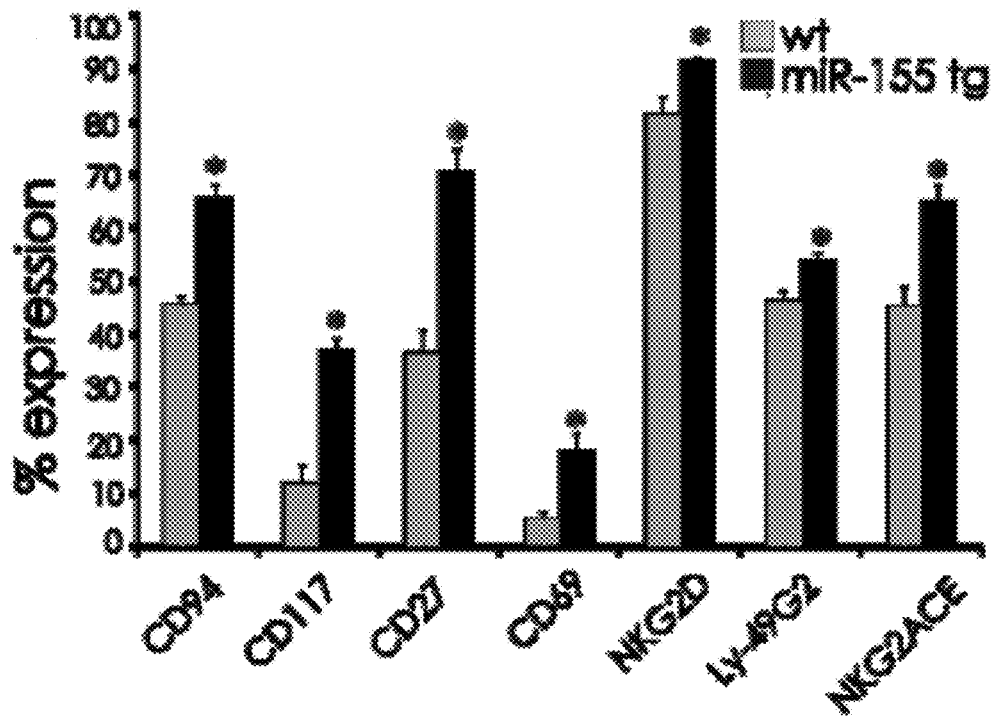
FIGS. 22A-22C: Comparative analysis of surface antigen expression on NK cells from miR-155 tg vs wt mice. Antigen expression was performed on gated $NK1.1^+CD3^-$ NK cells harvested from spleens of miR-155 tg and wt mice. The antigen of interest is labeled along the X axis.

To determine whether overexpression of miR-155 could have an effect on NK cell development and/or NK cell activation, a variety of well-characterized cell surface antigens in miR-155 tg NK cells were analyzed, and their expressions were compared to those of NK cells in wt mice. NK1.1$^+$CD3$^-$ splenocytes were gated on, and it was found that miR-155 tg mice had a significantly higher percentage of NK cells expressing CD94, CD117, CD27, CD69, NKG2D, Ly49G2, NKG2ACE (FIG. 22A; p<0.01).

Figure 22B:
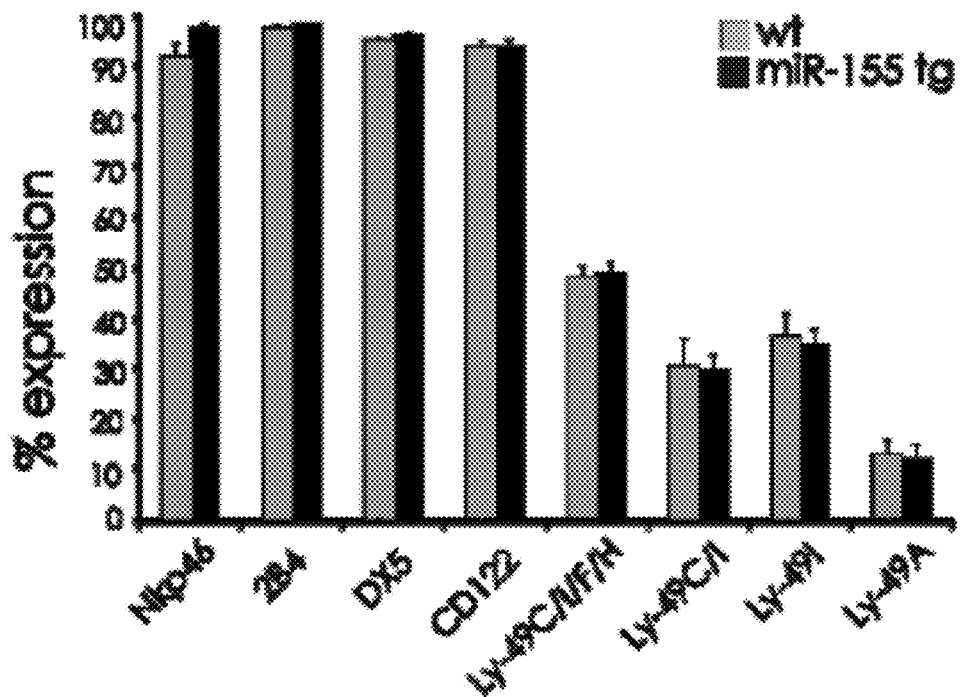
Figure 22C:
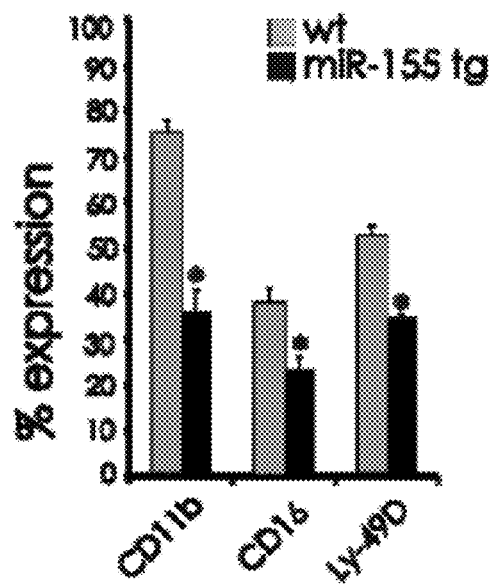

There were no significant differences in the expression of NKp46, 2B4, DX5, CD122, Ly49CIFH, Ly49C/I, Ly9I, and Ly49A (FIG. 22B; p>0.06), while NK cells from miR-155 tg mice had a significantly lower percent expression of CD11b, CD16 and Ly49D when compared to wt NK cells (FIG. 22C; p<0.01).

These differences in surface antigen expression were then used to explore developmental and functional differences between miR-155 tg NK cells and their wt counterparts.

Effect of miR-155 Overexpression on NK Cell Development

The noted decrease in the percentage of miR-155 tg NK cells expressing the late maturation markers CD11b and CD16, in addition to their increased expression of early maturation markers CD27 and CD117, denotes a block of terminal NK cell differentiation. To extend this analysis, NK1.1$^+$CD3$^-$ NK cells were gated on, and each subset was quantified, representing the three sequential stages of terminal NK mouse maturation: CD11b$^{low}$CD27$^{high}$, CD11b$^{high}$CD27$^{high}$ and CD11b$^{high}$CD27$^{low}$. MiR-155 tg splenocytes showed a clear and significant increase in the CD11b$^{low}$CD27$^{high}$ NK subset (p<0.001, n=7) and a significant decrease in the CD11b$^{high}$CD27$^{low}$ NK subset (p<0.001, n=7) when compared to wt NK subsets (FIG. 23A and FIG. 23B).

Figure 23A:
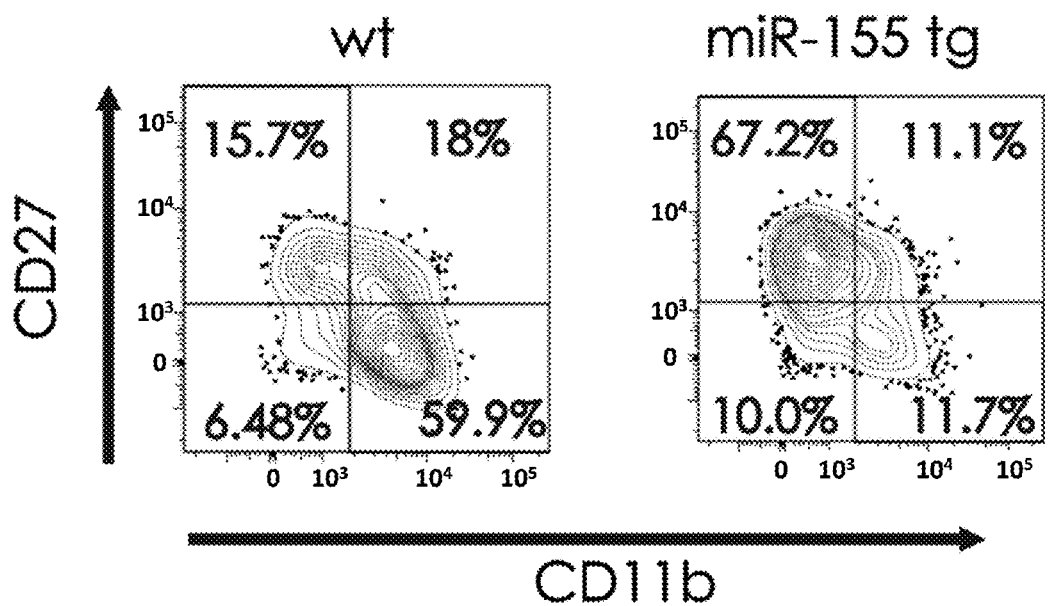
FIG. 23A-23E: The effect of miR-155 overexpression on terminal differentiation of NK cells.
Figure 23B:
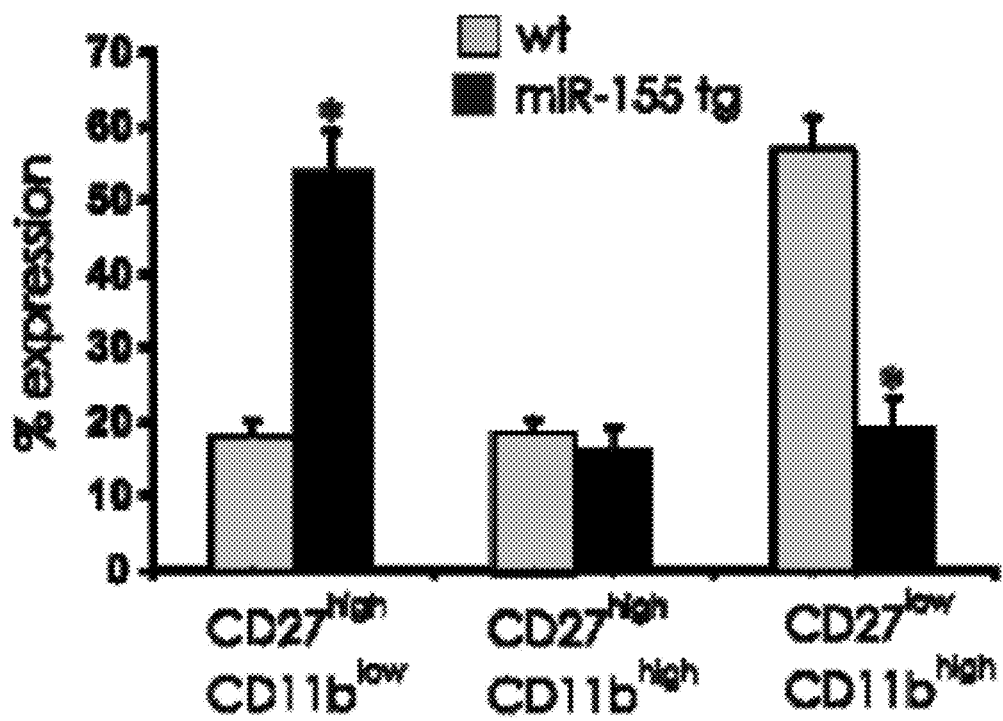

No significant difference was observed in CD11b$^{high}$CD27$^{high}$ subset in miR-155 tg versus wt NK cells (FIG. 23A and FIG. 23B; p=0.6, n=7). These data are consistent with a block in NK cell development at the earlier CD11b$^{low}$CD27$^{high}$ stage of differentiation.

To determine whether the block of NK terminal differentiation in miR-155 mice was due to an intrinsic defect, the CD11b$^{low}$CD27$^{high}$ CD45.2 NK subset from wt mice and from miR-155 tg mice was purified and adoptively transferred into CD45.1 wt recipient mice. After 16 days, the percentage of CD11b$^{low}$CD27$^{high}$, CD11b$^{high}$CD27$^{high}$ and CD11b$^{high}$CD27$^{low}$ CD45.2$^+$ NK subsets in spleen was analyzed by FACS.

Figure 23C:
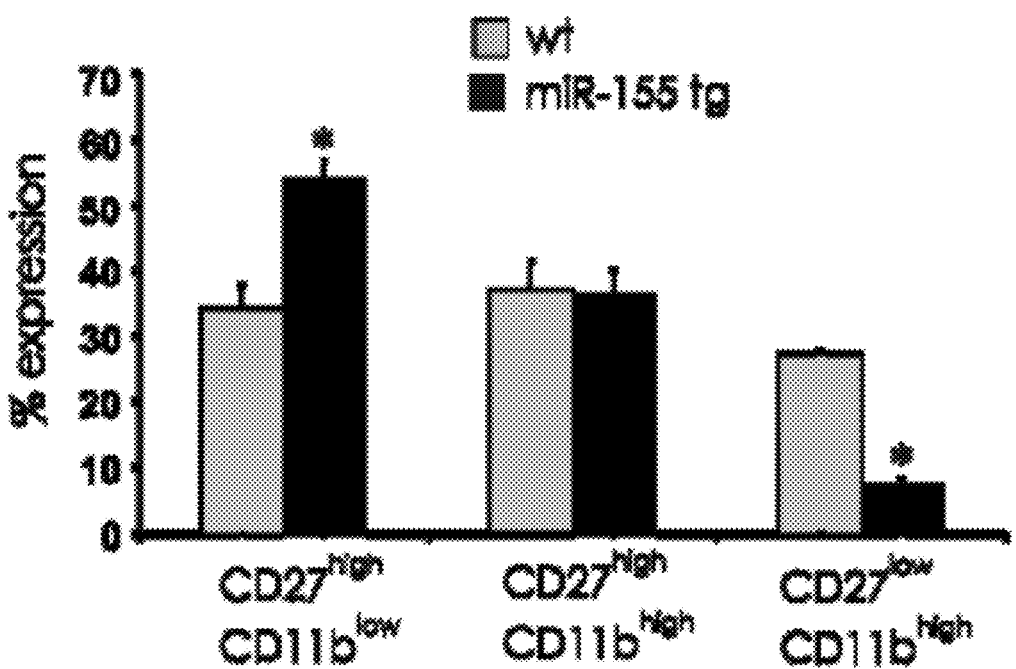
Figure 23D:
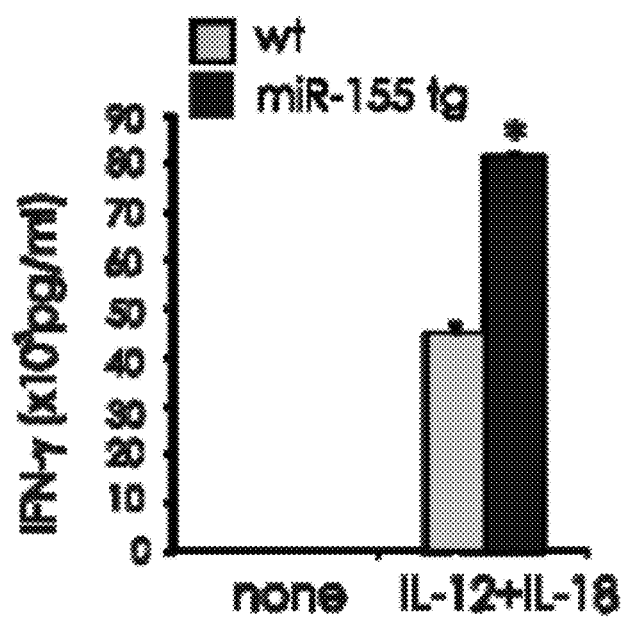
Figure 23E:
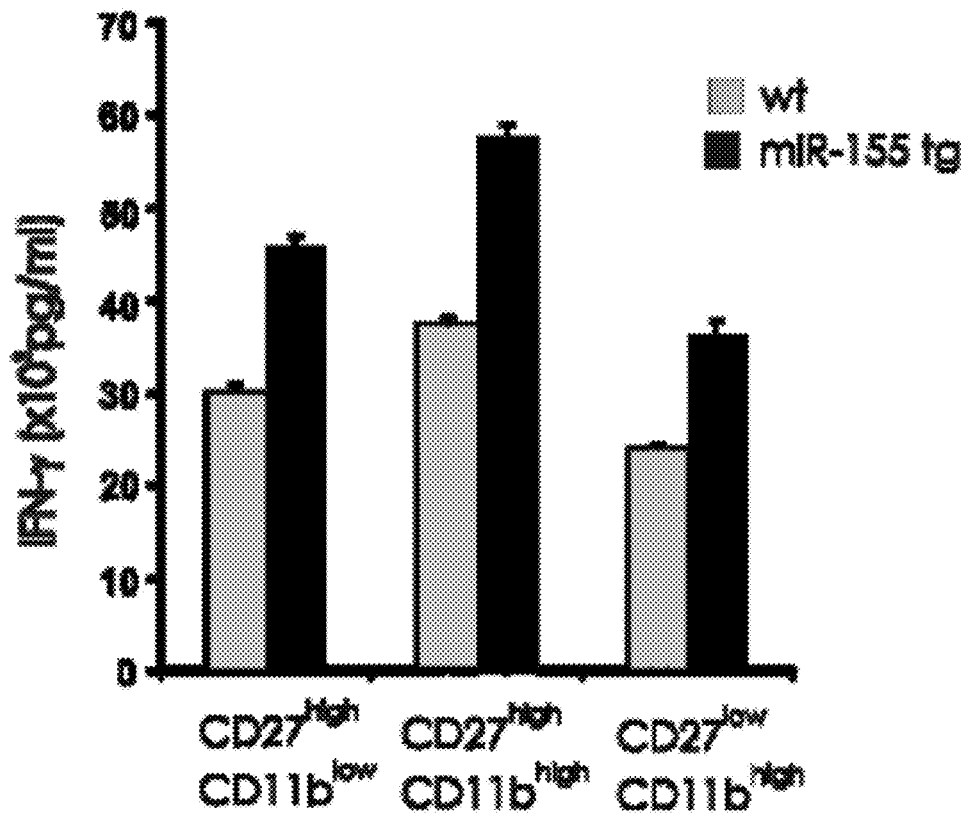

FIG. 23C shows a higher percentage of miR-155 tg CD11b$^{low}$CD27$^{high}$ immature NK cells in vivo relative to the percentage of wt CD11b$^{low}$CD27$^{high}$ immature NK cells (P<0.02; n=8), and a clear decrease in the percentage of miR-155 tg CD11b$^{high}$CD27$^{low}$ mature NK cells relative to the percentage of wt CD11b$^{high}$CD27$^{low}$ mature NK cells found in vivo (P<0.001; n=8). Thus, the accumulation of the relatively immature CD11b$^{low}$CD27$^{high}$ NK cells in miR-155 tg mice is now shown herein to be secondary to an intrinsic arrest in NK cell maturation.

Effect of miR-155 Overexpression on NK Cell IFN-γ Production

The increase in the percent of miR-155 tg NK cells expressing the activation marker CD69 was associated with high levels of CD94 and shows that a majority of these cells were in a heightened state of activation.

To further assess this, total NK1.1$^+$CD3$^-$ NK cells were taken from miR-155 tg and wt mice and analyzed for their ability to produce IFN-γ. MiR-155 tg NK cells produced significantly higher amounts of IFN-γ when compared to an equivalent number of wt NK cells following in vitro stimulation with IL-12 plus IL-18 (FIG. 23D; p<0.001; n=6).

To determine the relationship between this NK function and the three CD27/CD11b stages of NK cell differentiation, the CD11b$^{low}$CD27$^{high}$, CD11b$^{high}$CD27$^{high}$ and CD11b$^{high}$CD27$^{low}$ NK subsets from miR-155 tg and wt mice were FACS-sorted and assessed for their ability to produce IFN-γ. Using pooled NK cell subsets from several mice for each of two experiments, it was observed that each of the three miR-155 tg NK cell subsets produced significantly higher IFN-γ than their comparable wt NK cell subset (FIG. 23E).

It was also observed that the miR-155 tg CD11b$^{low}$CD27$^{high}$ immature NK cell subset produced significantly more IFN-γ than the more mature miR-155 tg or wt CD11b$^{high}$CD27$^{low}$ NK subset (FIG. 23E). This also confirmed that CD11b$^{high}$CD27$^{high}$ NK cells secrete a higher level of IFN-γ compared to the more terminally mature CD11b$^{high}$CD27$^{low}$ NK subset.

Effect of miR-155 Overexpression on NK Cell Lytic Function

Figure 24A:
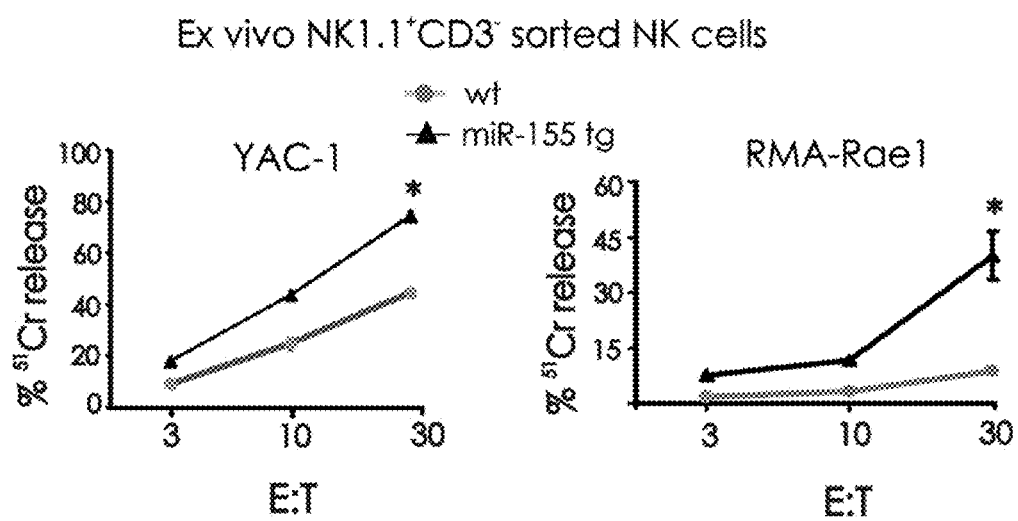
FIG. 24A-24E: Effect of miR-155 overexpression on NK cell cytotoxic effector functions.

To determine whether the overexpression of miR-155 in NK cells could influence NK cell mediated cytotoxicity, NK1.1$^+$CD3$^-$ NK cells from miR-155 tg and wt mice were tested ex vivo for their ability to kill the prototypic tumor cell target YAC-1, as well as the RMA tumor cell line that has high surface density expression of the NKG2D ligand Rae1β (RMA-Raeiβ). Freshly isolated NK cells overexpressing miR-155 lysed both YAC-1 (p<0.01, n=9) and RMA-Rae1β (p=0.02, n=5) tumor targets with significantly higher efficiency compared to wt NK cells (FIG. 24A).

Figure 24B:
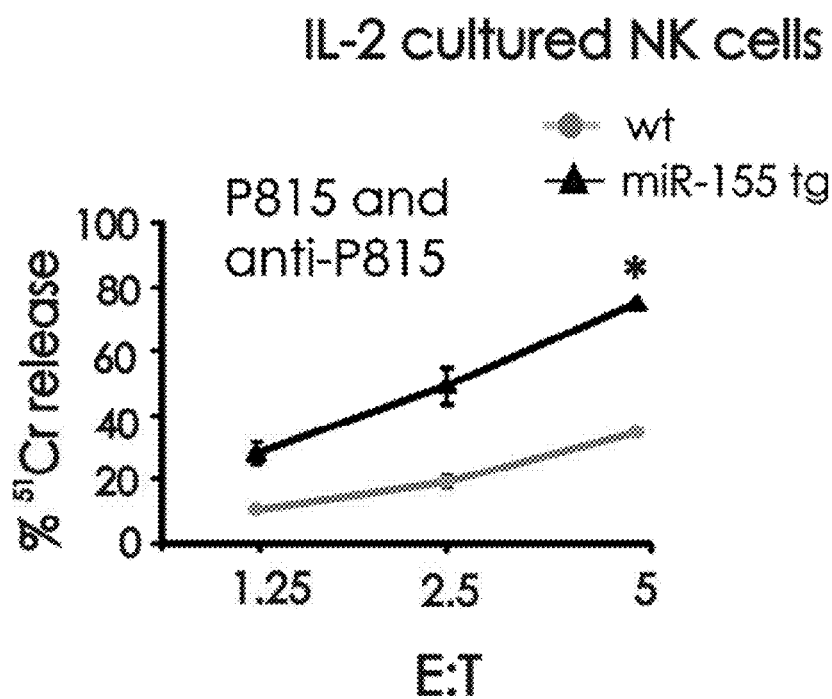

A very low level of cytotoxicity was observed using control RMA target cells not expressing Rae1β. Following eight days of culture in IL-2, these differences in spontaneous cytotoxic function between miR-155 tg NK cells and wt NK cells disappeared, yet miR-155 tg NK cells had significantly higher antibody-dependent cellular cytotoxicity (ADCC) against P815 antibody coated target cells when compared to wt NK cells incubated with IL-2 (FIG. 24B; p<0.001, n=5). In the absence of such activation, NK cell ADCC was low, yet significantly higher in freshly isolated miR-155 tg NK cells compared to wt NK cells.

Having shown that miR-155 NK cells have enhanced ability to kill RMA-Rae1β cells in vitro, it was then determined whether they maintained an enhanced ability to suppress RMA-Rae1β tumor growth compared to their wt counterpart in vivo. FACS sorted wt and miR-155 NK cells were co-injected with RMA-Rae1β cells subcutaneously to Rag2$^{-/-}$xIl2rg$^{-/-}$ mice. These mice do not express T cells or NK cells. MiR-155 tg NK cells significantly inhibited the growth of RMA-Rae1β tumor when compared to wt NK cells in vivo (FIG. 24C).

Figure 24C:
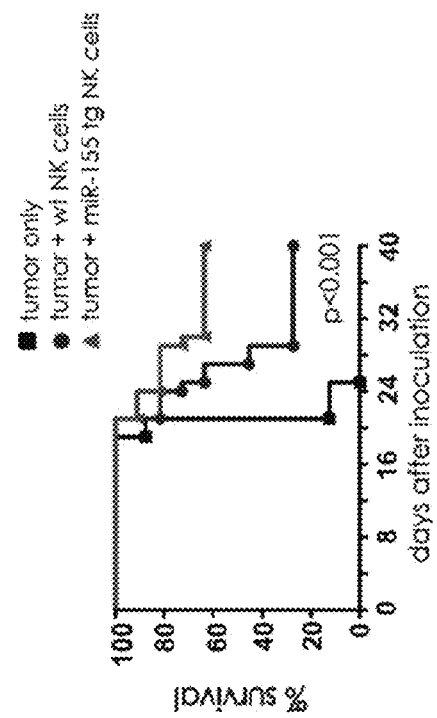
Figure 24C:
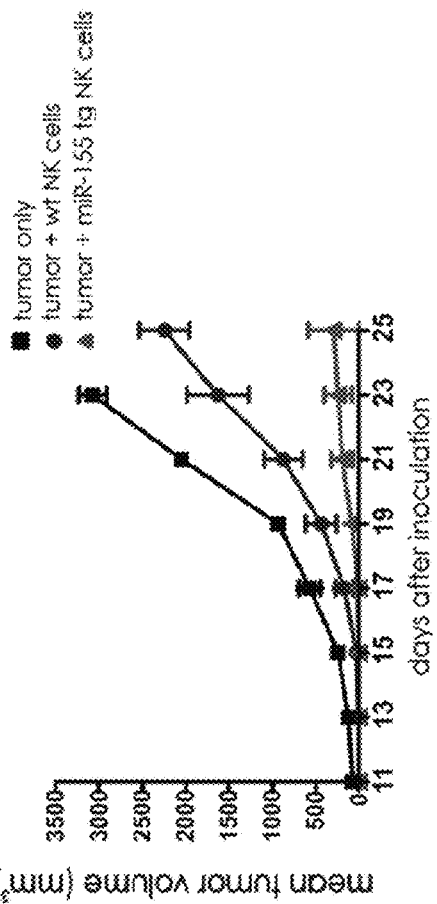

Further, in two independent experiments 63.6% of mice receiving RMA-Rae1β tumor cells co-injected with miR-155 tg NK cells survived, while only 27.2% survived after receiving RMA-Rae1β tumor cells co-injected with wt NK cells 40 days after initiation of the experiment (FIG. 24C; p<0.001, n=11). These data show that miR-155 overexpressing cells have an enhanced ability to kill the RMA-Rae1β tumor in vitro and in vivo, and this translates into a survival advantage in vivo.

Figure 24D:
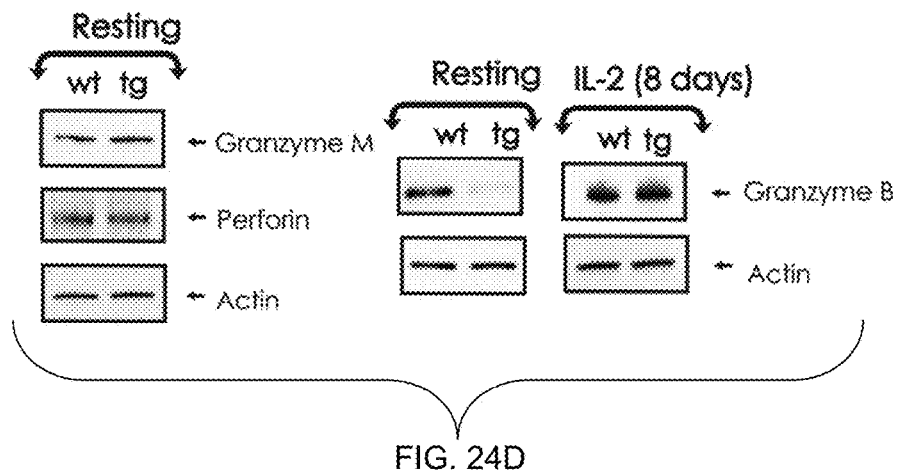

To determine cellular mechanisms responsible for the significantly enhanced NK cell cytolysis in miR-155 tg NK cells compared to wt NK cells, the protein levels of Granzyme B, Granzyme M, and Perforin were analyzed by immunoblot analysis. Granzyme B protein levels were significantly decreased in miR-155 tg NK cells compared to wt NK cells, yet this down-modulation was completely reversed after activation in the presence of IL-2 (FIG. 24D). No significant differences were otherwise observed in levels of Granzyme M and Perforin in miR-155 tg vs wt NK cells.

Figure 24E:
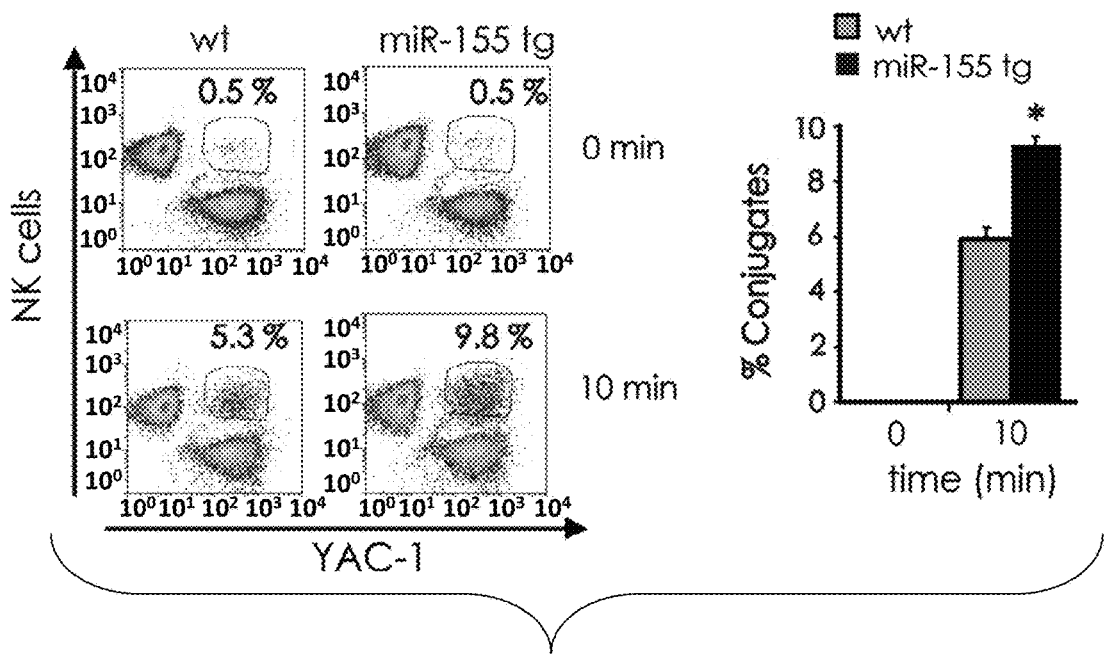

Since the formation of stable conjugates between NK cells and target cells is critical for activation of NK cell cytotoxicity, the ability of miR-155 tg vs wt NK cells to form conjugates with YAC-1 tumor cells was analyzed. As shown in FIG. 24E, miR-155 tg NK cells have a significantly enhanced ability to form conjugates with YAC-1 cells when compared to wt NK cells (FIG. 24E; p<0.01, n=3). This shows the enhanced ability of miR-155 NK cells to kill tumor cell targets over wt NK cells.

Ship1 Expression and Phosphorylation of Akt and Erk in miR-155 tg NK Cells

Figure 25A:
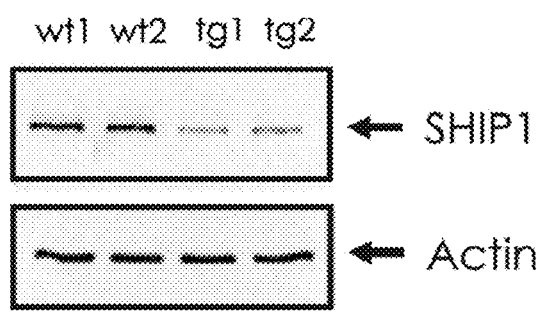
FIGS. 25A-25C: Effect of miR-155 overexpression on Ship1 protein expression and Akt and Erk activation in NK cells.
Figure 25B:
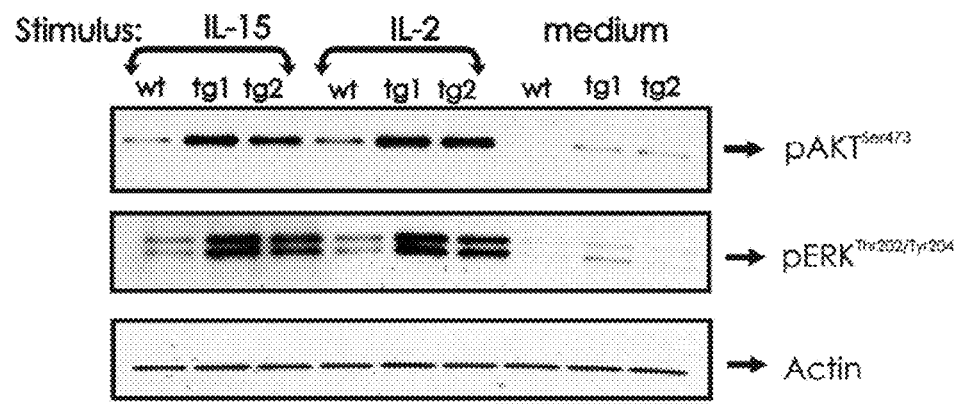
Figure 25C:
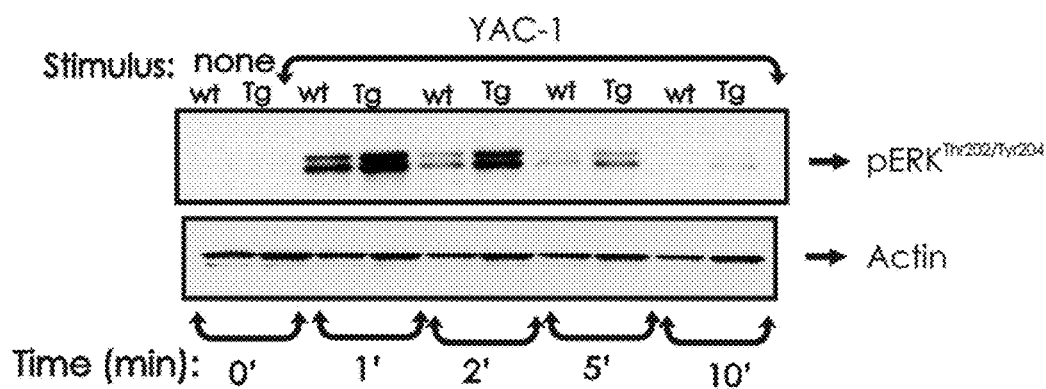

SHIP1 5' inositol phosphatase is a target of miR-155 in human NK cells, such that forced overexpression of miR-155 resulted in downregulation of SHIP1. Immunoblot analysis for Ship1 was performed on NK1.1$^+$CD3NK cells. Ship1 was down-modulated in miR-155 tg NK cells (FIG. 25A). Ship1 is a negative regulator of the PI-3K pathway of which Akt is a downstream target. Following activation by either IL-2 or IL-15 (and occasionally even in the absence of cytokine stimulation), Akt was observed to be visibly more phosphorylated in miR-155 tg NK cells compared to wt NK cells (FIG. 25B). Since ERK is also a downstream target of PI-3K in NK cells, whether overexpression of miR-155 enhances activation of Erk was next evaluated. Similar to Akt, Erk phosphorylation was visibly higher in miR-155 tg NK cells when compared to wt NK cells following culture in IL-2 or IL-15, and occasionally in the absence of cytokines. Since ERK signaling regulates cytotoxicity in NK cells, we also quantified Erk phosphorylation after binding YAC-1 tumor target cells. MiR-155 tg NK cells have higher levels of phospho-active Erk compared to wt NK cells after conjugation with YAC-1 tumor target cells (FIG. 25C).

These examples show that, at least following stimulation with cytokines or following interaction with tumor target cells, NK cells from miR-155 tg mice possess intrinsically enhanced activation of Akt and Erk when compared to wt NK cells.

The examples further reflect in vivo observations showing that overexpression of miR-155 increases the number of NK cells. This is indicative of altered homeostasis, a process that depends on a balance of the rates of NK cell production, proliferation, survival, and cell death.

In accordance with the present disclosure, miR-155 tg NK cells have improved survival compared to wt NK cells in the absence of cytokines, and show improved expansion compared to wt NK cells in the presence of IL-15. These data show that miR-155 has an intrinsic effect on NK cell survival as well as a role in promoting the extrinsic effect of its growth and survival factor, IL-15. Also shown is the enhanced expression of phospho-Akt and phospho-Erk in IL-15-activated miR-155 tg NK cells compared to wt NK cells. Both of these phosphorylated proteins are important components of NK cell survival and growth pathways, likely in response to endogenous IL-15.

When endogenous IL-15 is increased, the in vivo expansion of NK cells in the double tg mice was significantly greater than the significant increase seen in either single tg model. Without wishing to be bound by theory, if IL-15 does not directly control miR-155, then in vivo NK homeostasis may also be regulated by the intrinsic expression of miR-155 in NK cells.

Enhanced survival of miR-155 tg NK cells in the absence of IL-15 may be mediated in part by other pathways regulated by miR-155. For example, the absence of PI-3K isoforms (p110δ or p110γ) leads to a reduction of NK cells. On the other hand, an absence of Ship1 leads to an increase in NK cells due to enhanced survival. Here it is shown that miR-155 tg NK cells have reduced Ship1 expression and as a result likely have increased PI-3K which in turn promotes NK cell survival.

Overexpression of miR-155 positively influences the NK cell survival and proliferation pathways mediated by the receptor tyrosine kinase c-kit and its ligand in NK cells. The excess CD11b$^{low}$CD27$^{high}$ NK subset has a relatively high expression of c-kit. Thus, without wishing to be bound by theory, this receptor, tyrosine kinase, and its ligand, are now believed to contribute to the disproportionally high fraction of immature NK cells seen in the miR-155 tg mice, and may do so via a pathway that is positively regulated by miR-155.

Alterations in expression of two cell surface antigens that characterize the terminal differentiation stages of mouse NK cells, CD27 and CD11b, were observed. A clear and significant enrichment in the earliest stage of terminal NK cell maturation, CD11b$^{low}$CD27$^{high}$, was discovered in miR-155 tg mice when compared with wt mice. Moreover, the excess of this immature fraction persisted upon adoptive transfer into wt mice, consistent with a potential intrinsic block in the process of NK cell differentiation being mediated by miR-155.

Despite a partial block in terminal differentiation, miR-155 tg NK cells appear fully functional in terms of cytokine production and cytotoxicity. The latter is in part mediated by NKG2D, one of the activating NK cell receptors involved in eliminating tumor- and virus-infected cells. The enhanced killing at rest in miR-155 tg NK cells clearly does not depend on enhanced Granzyme B expression that is surprisingly low in these cells at rest.

Granzyme B levels can be rescued by IL-2 activation in miR-155 tg NK cells. Thus, low expression of Granzyme B may not depend on a direct effect of miR-155. The 3'UTR of Granzyme B mRNA does not have binding sites for miR-155.

Successful control of tumor growth and improved survival in vivo by adoptively transferring miR-155 tg NK cells into immune deficient hosts (which were not as well protected by wt NK cells) shows that such adoptive therapy with NK cells engineered to overexpress miR-155 is useful in treating diseases where NK cell therapy has efficacy, such as acute myeloid leukemia.

Further shown by Example II below is the usefulness of a transgenic mouse with overexpression of miR-155 driven off of the lck promoter, whose selective expression enables assessment of the relevance of particular miRs on the development, homeostasis, and function of NK cells. Such an animal, having a disruption in endogenous miR-155, is useful for many purposes. In certain embodiments, the transgenic mouse further comprises a disruption in endogenous IL-15.

It is now shown herein that miR-155, when over-expressed in NK cells, positively regulates NK cell expansion and NK effector functions despite an intrinsic block in terminal differentiation.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

Certain embodiments of the methods and compositions disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of treating a subject that has an infection or cancer disease comprising:
    delivering miR-155 into NK cells to create miR-155 tg NK cells, wherein the miR-155 tg NK cells overexpress miR-155;
    stimulating the miR-155 tg NK cells with an interleukin; and
    transferring the stimulated miR-155 tg NK cells into the subject having the disease to treat the disease.

2. The method of claim 1, wherein the interleukin is selected from the group consisting of IL-2, IL-12, IL-15, IL-18, IL-20 and a combination thereof.

3. The method of claim 1, wherein the cancer disease is acute myeloid leukemia.

4. The method of claim 1, wherein the cancer disease is lymphoma.

5. The method of claim 1, wherein the infection disease comprises inflammation.

6. The method of claim 1, wherein the miR-155 is delivered into the NK cells through a nanoparticle.

7. The method of claim 6, wherein the nanoparticle comprises chitosan.

8. The method of claim 1, wherein the miR-155 is delivered into the NK cells through a liposomal formulation.

9. The method of claim 2, wherein the interleukin comprises IL-20 and is present at a concentration of about 20 ng/mL.

10. The method of claim 1, wherein the interleukin comprises IL-18 and is present at a concentration of about 10 ng/mL.

* * * * *

UNITED STATES PATENT AND TRADEMARK OFFICE
CERTIFICATE OF CORRECTION

PATENT NO. : 9,603,873 B2
APPLICATION NO. : 14/649054
DATED : March 28, 2017
INVENTOR(S) : Michael A. Caligiuri et al.

Page 1 of 1

It is certified that error appears in the above-identified patent and that said Letters Patent is hereby corrected as shown below:

On the Title Page

(72) Inventors: please correct "Rossana Trott, Columbus, OH (US)" to -- Rossana Trotta, Columbus, OH (US) --.

In the Claims

Column 36, Claim 10, Line 17, after claim delete "1" and insert -- 2 --.

Signed and Sealed this
Ninth Day of May, 2017

Michelle K. Lee
*Director of the United States Patent and Trademark Office*